United States Patent [19]

Albright et al.

[11] Patent Number: 5,610,156
[45] Date of Patent: *Mar. 11, 1997

[54] TRICYCLIC BENZAZEPINE VASOPRESSIN ANTAGONISTS

[75] Inventors: Jay D. Albright, Nanuet; Aranapakam M. Venkatesan, Elmhurst, both of N.Y.

[73] Assignee: American Cyanamid Company, Madison, N.J.

[ * ] Notice: The term of this patent shall not extend beyond the expiration date of Pat. No. 5,536,718.

[21] Appl. No.: 458,210

[22] Filed: Jun. 2, 1995

Related U.S. Application Data

[62] Division of Ser. No. 373,132, Jan. 17, 1995, Pat. No. 5,536,718.

[51] Int. Cl.$^6$ ............ C07D 487/04; A61K 31/55
[52] U.S. Cl. ............ 514/220; 540/561
[58] Field of Search ............ 540/561; 514/220

[56] References Cited

U.S. PATENT DOCUMENTS

| | | | |
|---|---|---|---|
| 4,766,108 | 8/1988 | Ali | 514/16 |
| 5,055,448 | 10/1991 | Manning et al. | 514/16 |
| 5,070,187 | 12/1991 | Gavras et al. | 530/315 |
| 5,258,510 | 11/1993 | Ogawa et al. | 540/476 |

FOREIGN PATENT DOCUMENTS

| | | |
|---|---|---|
| 0382185 | 2/1990 | European Pat. Off. . |
| 0470514 | 8/1991 | European Pat. Off. . |
| 0514667 | 4/1992 | European Pat. Off. . |
| 0533242 | 9/1992 | European Pat. Off. . |
| 0533240 | 9/1992 | European Pat. Off. . |
| 0533243 | 9/1992 | European Pat. Off. . |
| 0533244 | 9/1992 | European Pat. Off. . |
| 0620216 | 4/1994 | European Pat. Off. . |
| 9105549 | 5/1991 | WIPO . |
| 9404525 | 3/1994 | WIPO . |
| 9414796 | 7/1994 | WIPO . |
| 9420473 | 9/1994 | WIPO . |
| 9412476 | 9/1994 | WIPO . |

OTHER PUBLICATIONS

J. Med. Chem., 1992, 35, 3905–3918, Williams et al.
J. Med. Chem., 1992, 35, 382–388, 3895–3904—Manning et al.
From Vasopressin Antagonist to Agonist, DN+P 4(4), May 1991, Ruffolo et al. pp. 217–221.
Br. J. Pharmacol. (1992), 105, 787–791, Yamamura et al.
Science, vol. 252, pp. 572–574, Yamamura et al. (1991).
J. Med. Chem., 1992, 35, 3919–3927, Evans et al.
J. Med. Chem., 1993, 36, 3993–4005, Evans et al.

Primary Examiner—Philip I. Datlow
Attorney, Agent, or Firm—Steven R. Eck

[57] ABSTRACT

Tricyclic compound of the general Formula I:

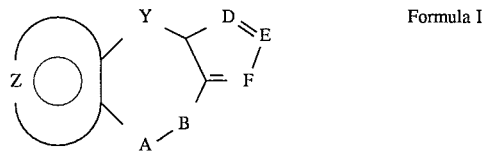

Formula I as defined herein which exhibit antagonist activity at $V_1$ and/or $V_2$ receptors and exhibit in vivo vasopressin antagonist activity, methods for using such compounds in treating diseases characterized by excess renal reabsorption of water, and process for preparing such compounds.

6 Claims, No Drawings

TRICYCLIC BENZAZEPINE VASOPRESSIN ANTAGONISTS

This application is a divisional application of U.S. Ser. No. 08/373,132, filed Jan. 17, 1995, now U.S. Pat. No. 5,536,718.

FIELD OF THE INVENTION

This invention relates to new tricyclic non-peptide vasopressin antagonists which are useful in treating conditions where decreased vasopressin levels are desired, such as in congestive heart failure, in disease conditions with excess renal water reabsorption and in conditions with increased vascular resistance and coronary vasoconstriction.

BACKGROUND OF THE INVENTION

Vasopressin is released from the posterior pituitary either in response to increased plasma osmolarity detected by brain osmoreceptors or decreased blood volume and blood pressure sensed by low-pressure volume receptors and arterial baroreceptors. The hormone exerts its action through two well defined receptor subtypes: vascular $V_1$ and renal epithelial $V_2$ receptors. Vasopressin-induced antidiuresis, mediated by renal epithelial $V_2$ receptors, helps to maintain normal plasma osmolarity, blood volume and blood pressure.

Vasopressin is involved in some cases of congestive heart failure where peripheral resistance is increased. $V_1$ antagonists may decrease systemic vascular resistance, increase cardiac output and prevent vasopressin induced coronary vasoconstriction. Thus, in conditions with vasopressin induce increases in total peripheral resistance and altered local blood flow, $V_1$-antagonists may be therapeutic agents. $V_1$ antagonists may decrease blood pressure, induced hypotensive effects and thus be therapeutically useful in treatment of some types of hypertension.

The blockage of $V_2$ receptors is useful in treating diseases characterized by excess renal reabsorption of free water. Antidiuresis is regulated by the hypothalamic release of vasopressin (antidiuretic hormone) which binds to specific receptors on renal collecting tubule cells. This binding stimulates adenylyl cyclase and promotes the cAMP-mediated incorporation of water pores into the luminal surface of these cells. $V_2$ antagonists may correct the fluid retention in congestive heart failure, liver cirrhosis, nephritic syndrome, central nervous system injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of antidiuretic hormone, On the basis of biochemical and pharmacological effects of the hormone, antagonists of vasopressin are expected to be therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, thrombosis-bleeding and abnormal states of water retention.

The following prior art references describe peptide vasopressin antagonists: M. Manning et al., *J. Med. Chem.*, 35, 382(1992); M. Manning et al., *J. Med. Chem.*, 35, 3895(1992); H. Gavras and B. Lammek, U.S. Pat. No. 5,070,187 (1991); M. Manning and W. H. Sawyer, U.S. Pat. No. 5,055,448(1991) F. E. Ali, U.S. Pat. No. 4,766,108(1988); R. R. Ruffolo et al., *Drug News and Perspective*, 4(4), 217, (May)(1991). P. D. Williams et al., have reported on potent hexapeptide oxytocin antagonists [*J. Med. Chem.*, 35, 3905(1992)] which also exhibit weak vasopressin antagonist activity in binding to $V_1$ and $V_2$ receptors. Peptide vasopressin antagonists suffer from a lack of oral activity and many of these peptides are not selective antagonists since they also exhibit partial agonist activity.

Non-peptide vasopressin antagonists have recently been disclosed, Y. Yamamura et al., *Science,* 252, 579(1991); Y. Yamamura et al., *Br. J. Pharmacol,* 105, 787(1992); Ogawa et al., (Otsuka Pharm Co., LTD.) EP 0514667-A1; EPO 382185-A2; WO9105549 and U.S. Pat. No. 5,258,510; WO 9404525 Yamanouchi Pharm. Co., Ltd., WO 9420473; WO 9412476; WO 9414796; Fujisawa Co. Ltd., EP 620216-A1 Ogawa et al, (Otsuka Pharm. Co.) EP 470514A disclose carbostyril derivatives and pharmaceutical compositions containing the same. Non-peptide oxytocin and vasopressin antagonist have been disclosed by Merck and Co.; M. G. Bock and P. D. Williams, EP 0533242A; M. G. Bock et al., EP 0533244A; J. M. Erb, D. F. Verber, P. D. Williams, EP 0533240A; K. Gilbert et al., EP 0533243A.

Premature birth can cause infant health problems and mortality and a key mediator in the mechanism of labor is the peptide hormone oxytocin. On the basis of the pharmacological action of oxytocin, antagonists of this hormone are useful in the prevention of preterm labor, B. E. Evans et al., *J. Med. Chem.* 35, 3919(1992), *J. Med. Chem.*, 36, 3993(1993) and references therein. The compounds of this invention are antagonists of the peptide hormone oxytocin and are useful in the control of premature birth.

The present invention relates to novel tricyclic derivatives which exhibit antagonist activity at $V_1$ and/or $V_2$ receptors and exhibit in vivo vasopressin antagonist activity. The compounds also exhibit antagonist activity at oxytocin receptors.

SUMMARY OF THE INVENTION

This invention relates to new compounds selected from those of the general formula I:

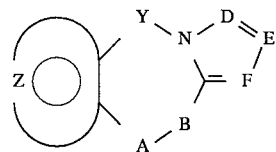

wherein Y is a moiety selected from; —$(CH_2)_n$— wherein n is an integer from 0 to 2,

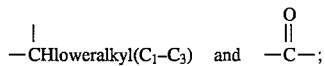

A–B is a moiety selected from

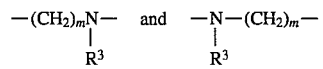

wherein m is an integer from 1 to 2 provided that when Y is —$(CH_2)_n$— and n is 2, m may also be zero and when n is zero, m may also be three, provided also that when Y is —$(CH_2)_n$— and n is 2, m may not be two;

and the moiety:

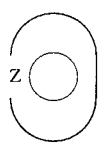

represents: (1) phenyl or substituted phenyl optionally substituted by one or two substituents selected from (C$_1$–C$_3$) lower alkyl, halogen, amino, (C$_1$–C$_3$) lower alkoxy or (C$_1$–C$_3$) lower alkylamino; (2) a 5-membered aromatic (unsaturated) heterocyclic ring having one heteroatom selected from O, N or S; (3) a 6-membered aromatic (unsaturated) heterocyclic ring having one nitrogen atom; (4) a 5 or 6-membered aromatic (unsaturated) heterocyclic ring having two nitrogen atoms; (5) a 5-membered aromatic (unsaturated) heterocyclic ring having one nitrogen atom together with either one oxygen or one sulfur atom; wherein the 5 or 6-membered heterocyclic rings are optionally substituted by (C$_1$–C$_3$) lower alkyl, halogen or (C$_1$–C$_3$) lower alkoxy; the moiety:

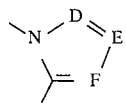

is a five membered aromatic (unsaturated) nitrogen containing heterocyclic ring wherein D, E and F are selected from carbon and nitrogen and wherein the carbon atoms may be optionally substituted by a substituent selected from halogen, (C$_1$–C$_3$) lower alkyl, hydroxy, —COCl$_3$, —COCF$_3$,

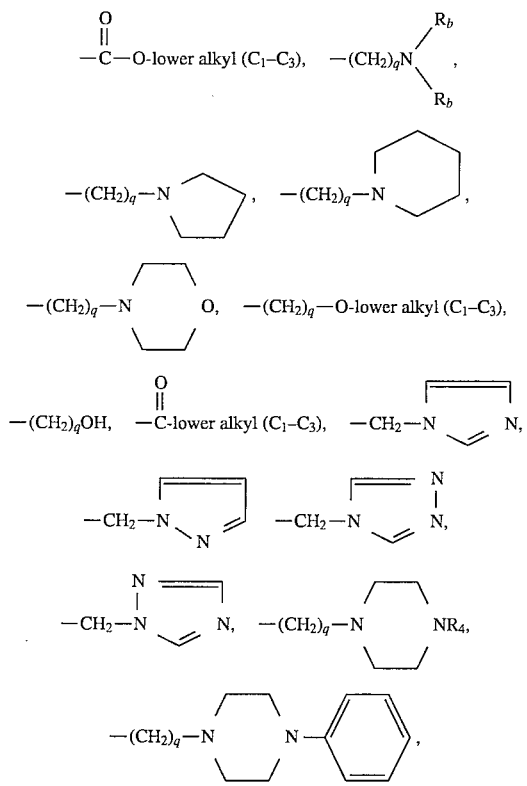

—CHO, amino, (C$_1$–C$_3$) lower alkoxy, (C$_1$–C$_3$) lower alkylamino, CONH-lower alkyl(C$_1$–C$_3$), and —CON[lower alkyl(C$_1$–C$_3$)]$_2$; q is one or two; R$_b$ is independently selected from hydrogen, —CH$_3$ or —C$_2$H$_5$;

R$^3$ is a moiety of the formula:

wherein Ar is a moiety selected from the group consisting of

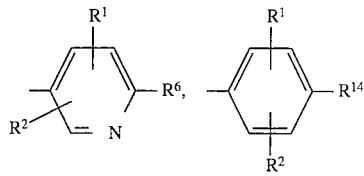

wherein R$^4$ is selected from hydrogen, lower alkyl(C$_1$–C$_3$), —CO lower alkyl(C$_1$–C$_3$);

R$^1$ and R$^2$ are selected from hydrogen, (C$_1$–C$_3$)lower alkyl, (C$_1$–C$_3$)lower alkoxy and halogen; R$^5$ is selected from hydrogen, (C$_1$–C$_3$)lower alkyl, (C$_1$–C$_3$)lower alkoxy and halogen; R$^6$ is selected from (a) moieties of the formulae:

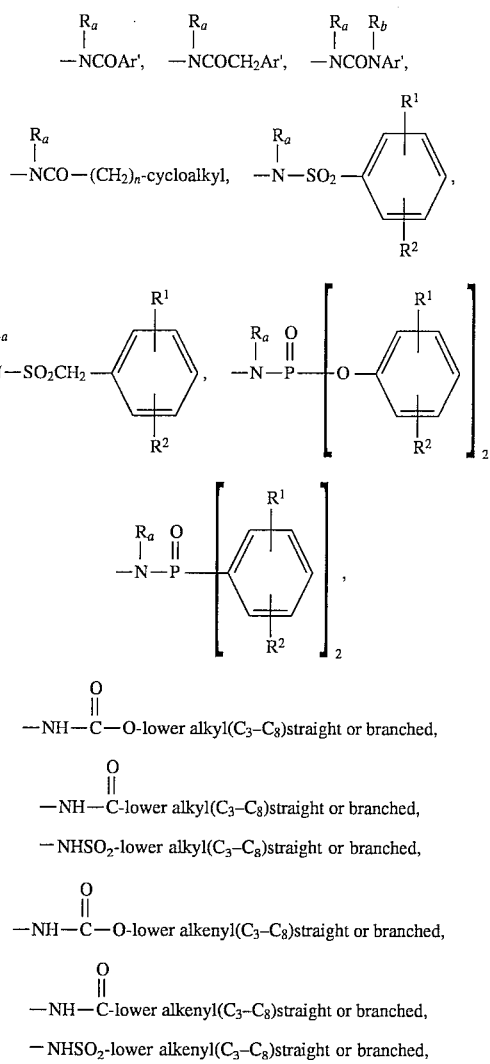

O
||
—NH—C—O-lower alkyl(C$_3$–C$_8$)straight or branched,

O
||
—NH—C-lower alkyl(C$_3$–C$_8$)straight or branched,

—NHSO$_2$-lower alkyl(C$_3$–C$_8$)straight or branched,

O
||
—NH—C—O-lower alkenyl(C$_3$–C$_8$)straight or branched,

O
||
—NH—C-lower alkenyl(C$_3$–C$_8$)straight or branched,

—NHSO$_2$-lower alkenyl(C$_3$–C$_8$)straight or branched, wherein cycloalkyl is defined as C$_3$–C$_6$ cycloalkyl, cyclohexenyl or cyclopentenyl; R$_a$ is independently selected from hydrogen, —CH$_3$, —C$_2$H$_5$,

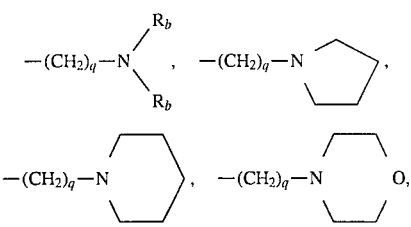

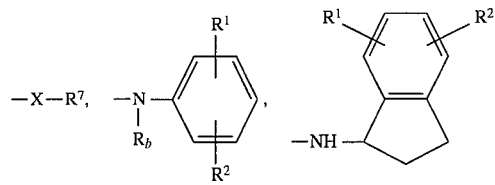

—(CH$_2$)$_q$—O-lower alkyl(C$_1$–C$_3$) and —CH$_2$CH$_2$OH, q is one or two, and R$_1$, R$_2$ and R$_b$ are as hereinbefore defined;

(b) moieties of the formula:

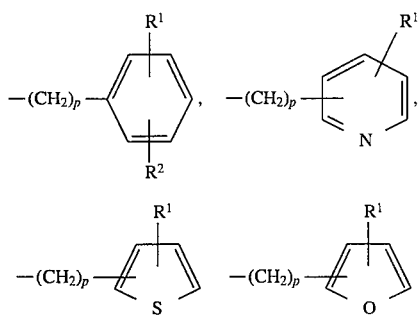

wherein R$^7$ is lower alkyl(C$_3$–C$_8$), lower alkenyl (C$_3$–C$_8$), —(CH$_2$)$_p$-cycloalkyl (C$_3$–C$_6$),

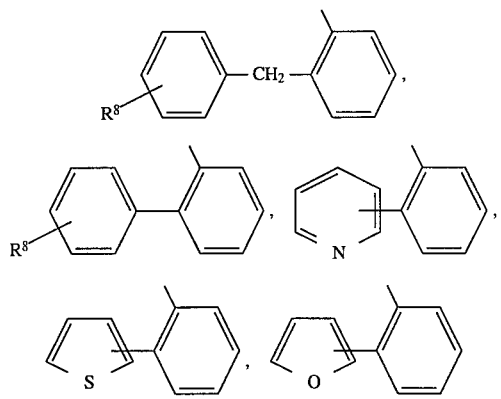

wherein p is one to five and X is selected from O, S, NH, NCH$_3$; wherein R$^1$ and R$^2$ are as hereinbefore defined;

(c) a moiety of the formula:

wherein J is R$_a$, lower alkyl(C$_3$–C$_8$) branched or unbranched, lower alkenyl(C$_3$–C$_8$) branched or unbranched, O-lower alkyl(C$_3$–C$_8$) branched or unbranched, —O-lower alkenyl(C$_3$–C$_8$) branched or unbranched, tetrahydrofuran, tetrahydrothiophene, the moieties:

or —CH$_2$—K' wherein K' is (C$_1$–C$_3$) lower alkoxy, halogen, tetrahydrofuran, tetrahydrothiophene or the heterocyclic ring moiety:

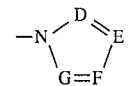

wherein D, E, F and G are selected from carbon or nitrogen and wherein the carbon atoms may be optionally substituted with halogen, (C$_1$–C$_3$) lower alkyl, hydroxy, —CO-lower alkyl (C$_1$–C$_3$), CHO, (C$_1$–C$_3$) lower alkoxy, —CO$_2$-lower alkyl(C$_1$–C$_3$), and R$_a$ and R$_b$ are as hereinbefore defined;

(d) a moiety of the formula:

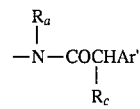

wherein R$_c$ is selected from halogen, (C$_1$–C$_3$) lower alkyl, —O-lower alkyl(C$_1$–C$_3$), OH,

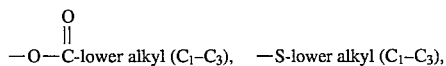

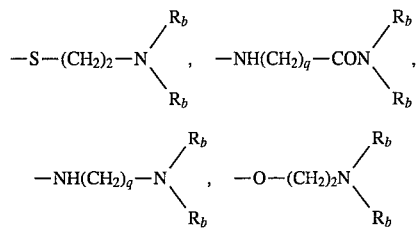

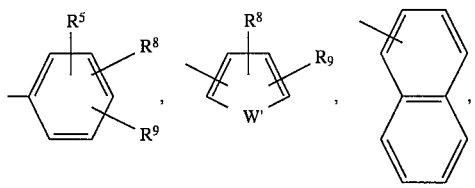

wherein R$_a$ and R$_b$ are as hereinbefore defined and Ar' is selected from moieties of the formula:

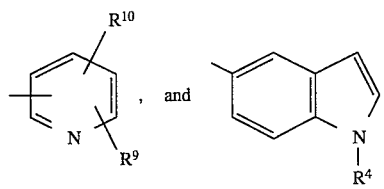

wherein W' is selected from O, S, NH, N-lower alkyl(C$_1$–C$_3$), NHCO-lower alkyl (C$_1$–C$_3$), and NSO$_2$lower alkyl (C$_1$C$_3$);

R$^8$ and R$^9$ are independently selected from hydrogen, lower alkyl (C$_1$–C$_3$), —S-lower alkyl (C$_1$–C$_3$), halogen, —NH-lower alkyl (C$_1$–C$_3$), —N-[lower alkyl (C$_1$–C$_3$)]$_2$, —OCF$_3$, —OH, —CN, —S—CF$_3$, —NO$_2$, —NH$_2$, O-lower alkyl (C$_1$–C$_3$),

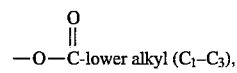

—N(R$_b$) (CH$_2$)$_v$N (R$_b$)$_2$, and CF$_3$ wherein v is one to three and;

$R^{10}$ is selected from hydrogen, halogen and lower alkyl $(C_1-C_3)$; $R^{14}$ is —O-lower alkyl$(C_3-C_8)$branched or unbranched,

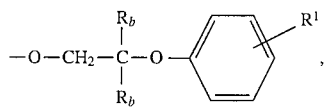

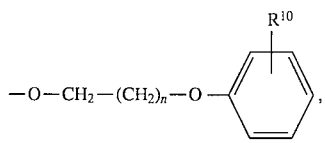

—NH lower alkyl$(C_3-C_8)$ branched or unbranched,

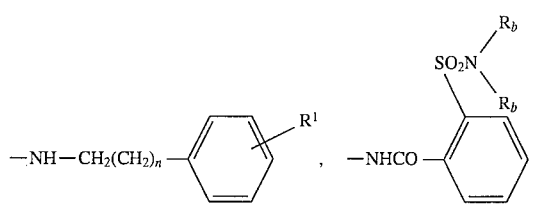

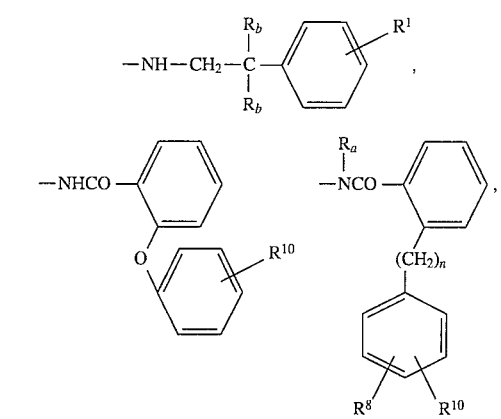

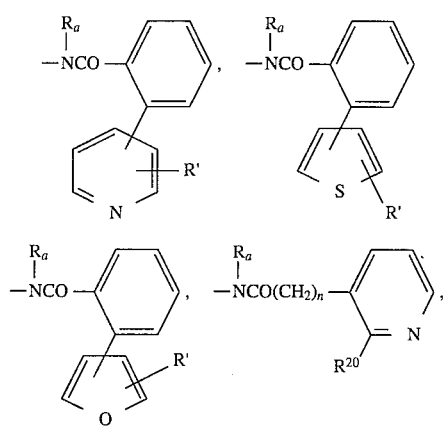

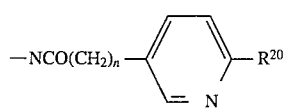

wherein n is 0 or 1; $R_a$ is hydrogen, —CH$_3$ or —C$_2$H$_5$; R' is hydrogen, $(C_1-C_3)$lower alkyl, $(C_1-C_3)$lower alkoxy and halogen; $R^{20}$ is hydrogen, halogen, $(C_1-C_3)$lower alkyl, $(C_1-C_3)$lower alkoxy, NH$_2$, —NH$(C_1-C_3)$lower alkyl, —N—[$(C_1-C_3)$lower alkyl]$_2$,

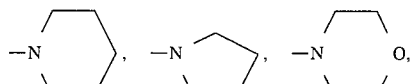

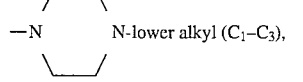

—NH—(CH$_2$)$_p$—NHlower alkyl $(C_1-C_3)$,

—NH—(CH$_2$)$_p$—N[lower alkyl $(C_1-C_3)$]$_2$

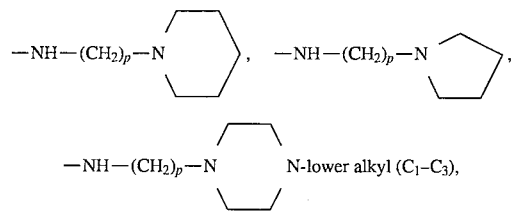

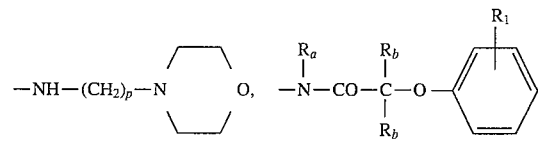

and the pharmaceutically acceptable salts thereof.

DETAILED DESCRIPTION OF THE INVENTION

Within the group of the compounds defined by Formula I, certain subgroups of compounds are broadly preferred. Broadly preferred are those compounds wherein $R_3$ is the moiety:

and Ar is selected from the moieties:

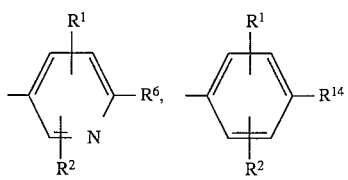

Y is (CH$_2$)$_n$ and n is one or zero;
wherein $R^1$, $R^2$, $R^4$, $R^5$, $R^6$ and $R^{14}$ are as hereinbefore defined.

Especially preferred are compounds wherein $R^3$ is the moiety:

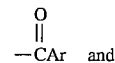

and

Ar is selected from the moieties:

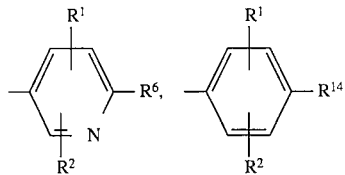

Y is —(CH$_2$)$_n$ and n is one and m is one;
wherein R$^1$, R$^2$, R$^4$, R$^6$ and R$^{14}$ are as hereinbefore defined.

Especially preferred are compounds wherein R$^3$ is the moiety:

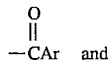

—CAr    and

Ar is selected from the moieties:

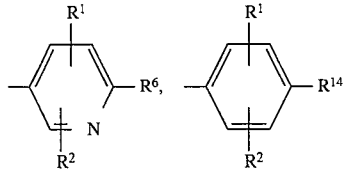

Y is —(CH$_2$)$_n$ and n is one or zero;
R$^6$ is

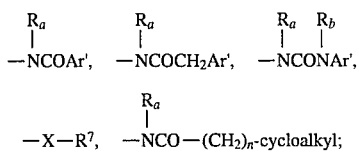

wherein cycloalkyl is defined as C$_3$–C$_6$ cycloalkyl, cyclohexenyl or cyclopentenyl; and wherein X, R$_a$, R$_b$ and R$^{14}$ are as hereinbefore defined; and Ar' is selected from the moieties:

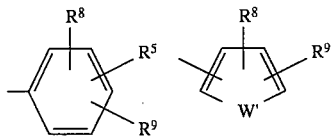

wherein R$^8$, R$^9$ and W' are as hereinbefore defined.

Also especially preferred are compounds wherein Y in Formula I is —(CH$_2$)$_n$— and n is zero or one; A–B is

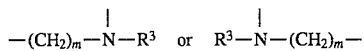

and R$^1$, R$^2$, R$^4$, R$^5$, R$^6$, R$^7$, R$^8$, R$^9$, R$^{10}$ and R$^{14}$ are as hereinbefore defined; and m is an integer from 1–2.

The most preferred of the compounds of Formula I are those wherein Y is —(CH$_2$)$_n$— and n is one; A–B is:

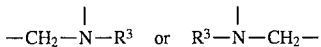

R$_3$ is the moiety:

Ar is selected from the moieties:

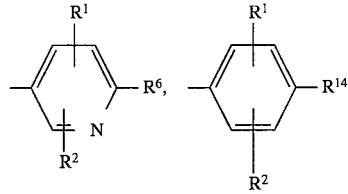

R$^6$ is

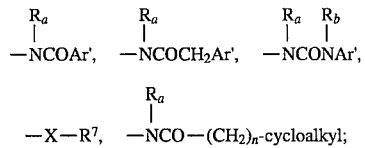

(CH$_2$)$_n$-cycloalkyl wherein cycloalkyl is defined as C$_3$–C$_6$ cycloalkyl, cyclohexenyl or cyclopentenyl; wherein X, R$_a$, R$_b$ and R$^{14}$ are as hereinbefore defined; and Ar' is:

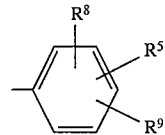

wherein R$^5$, R$^8$ and R$^9$ are as previously defined.

The most highly broadly preferred of the compounds of Formula I are those wherein Y is —(CH$_2$)$_n$— and n is zero or one; wherein the moiety:

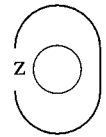

is a phenyl, substituted phenyl, thiophene, furan, pyrrole or pyridine ring;
A–B is:

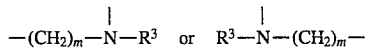

m is one when n is one and m is two when n is zero; D, E, F, R$^1$, R$^2$, R$^4$, R$^5$, R$^7$, R$^8$, R$^9$, R$^{10}$ are as previously defined;

$R_3$ is the moiety:

wherein Ar is selected from the moieties:

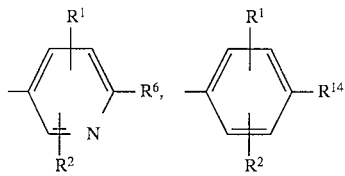

and $R_6$ is selected from the group:

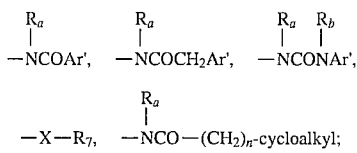

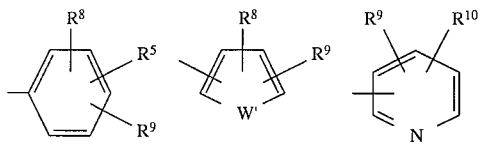

where Ar' is selected from the group:

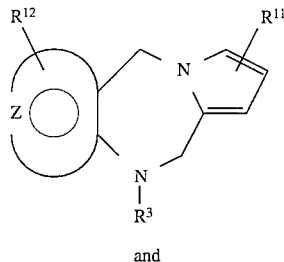

and $R^{14}$, X, W', $R_a$, $R_b$ and cycloalkyl are as previously described.

More particularly preferred are compounds of the formulae:

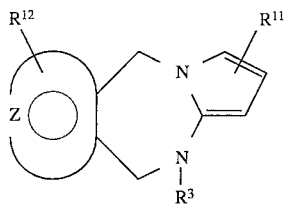

and

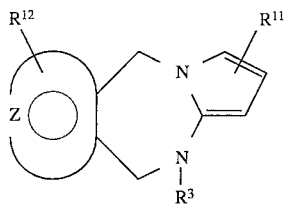

wherein the moiety:

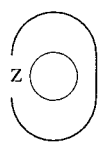

is selected from a phenyl, thiophene, furan, pyrrole, or pyridine ring;

$R^3$ is the moiety:

wherein Ar is selected from the moieties:

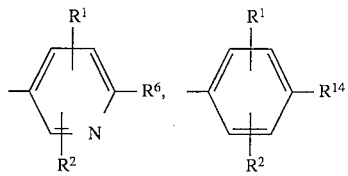

$R^6$ is

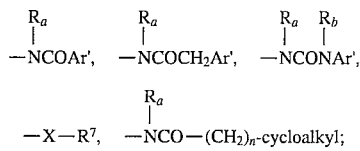

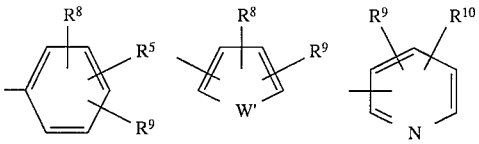

and Ar' is selected from the moieties:

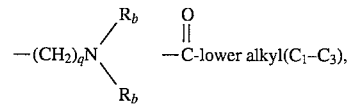

wherein X, $R_a$, $R_b$, $R^5$, $R^7$, $R^8$, $R^9$, $R^{14}$, cycloalkyl and W' are as hereinbefore described;

$R^{11}$ is selected from hydrogen, halogen, ($C_1$–$C_3$) lower alkyl, hydroxy,

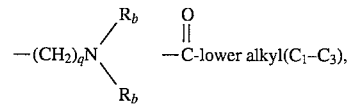

—CHO, and ($C_1$–$C_3$)lower alkoxy; and $R^{12}$ is selected from hydrogen, ($C_1$–$C_3$) lower alkyl, halogen and ($C_1$–$C_3$) lower alkoxy.

Also particularly preferred are compounds of the formulae:

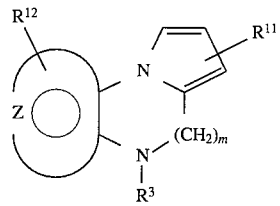

and

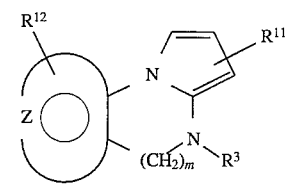

wherein m is one or two;

the moiety:

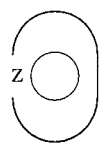

is selected from a phenyl, thiophene, furan, pyrrole or pyridine ring;

$R^3$ is the moiety:

wherein Ar is selected from the moieties:

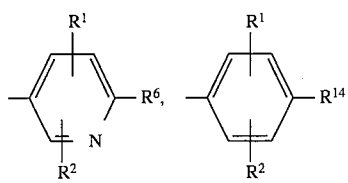

$R^6$ is

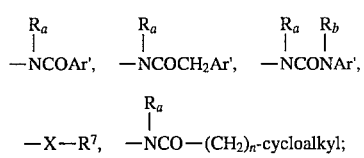

$(CH_2)_n$ cycloalkyl; Ar' is selected from the moieties:

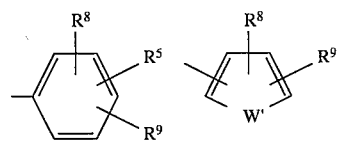

wherein X, $R_a$, $R_b$, $R^5$, $R^6$, $R^8$, $R^9$, $R^{14}$, cycloalkyl and W' are as hereinbefore defined;

$R^{11}$ is selected from hydrogen, halogen, $(C_1-C_3)$ lower alkyl, hydroxy,

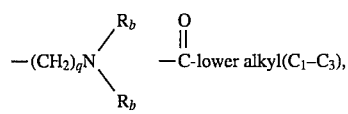

—CHO, and $(C_1-C_3)$ lower alkoxy; and $R^{12}$ is selected from hydrogen, $(C_1-C_3)$ lower alkyl, halogen and $(C_1-C_3)$ lower alkoxy.

More particularly preferred are compounds of the formulae:

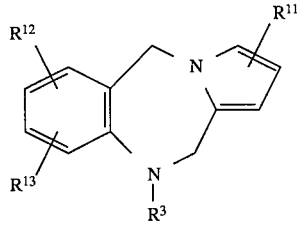

and

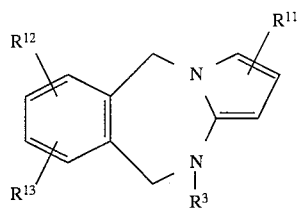

$R^3$ is the moiety:

wherein Ar is selected from the moieties:

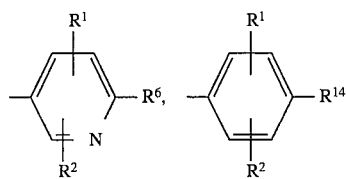

$R^6$ is

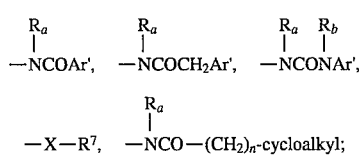

$R^{14}$ is

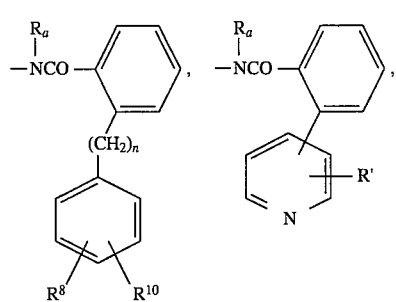

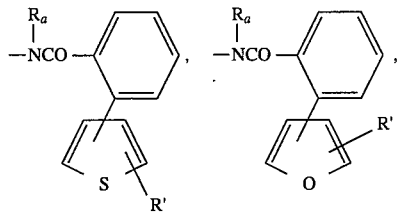

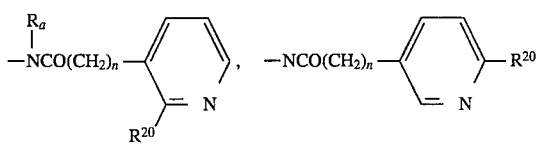

wherein n is 0 or 1; $R_a$ is hydrogen, —$CH_3$ or —$C_2H_5$; R' is hydrogen, $(C_1-C_3)$lower alkyl, $(C_1-C_3)$lower alkoxy and halogen; $R^{20}$ is hydrogen, halogen, $(C_1-C_3)$lower alkyl, $(C_1-C_3)$lower alkoxy, $NH_2$, —$NH(C_1-C_3)$ alkyl, —N—$[(C_1-C_3)$lower alkyl$]_2$,

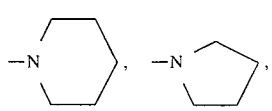

wherein cycloalkyl is defined as $C_3$–$C_6$ cycloalkyl, cyclohexenyl or cyclopentenyl; $R_b$ is hydrogen; $R_a$ is independently selected from hydrogen, —$CH_3$, —$C_2H_5$ or —$(CH_2)_q N(CH_3)_2$; Ar' is selected from the moieties:

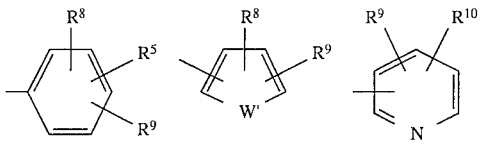

wherein q, X, $R_a$, $R_b$, $R^5$, $R^7$, $R^8$, $R^9$, $R^{10}$, $R^{11}$ and W' are as hereinbefore described;

$R^{12}$ and $R^{13}$ are independently selected from hydrogen, ($C_1$–$C_3$) lower alkyl, halogen, amino, ($C_1$–$C_3$) lower alkoxy or ($C_1$–$C_3$) lower alkylamino.

Also particularly preferred are compounds of the formulae:

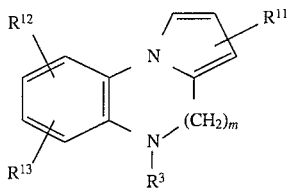

and

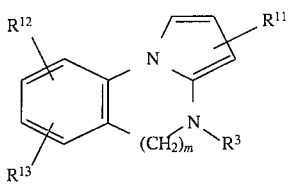

wherein m is one or two;
$R^3$ is the moiety:

wherein Ar is selected from the moieties:

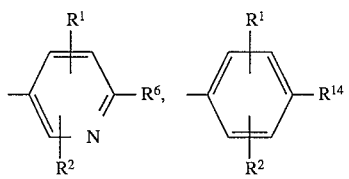

$R^6$ is

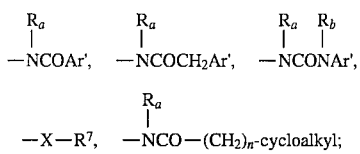

wherein cycloalkyl is defined as $C_3$–$C_6$ cycloalkyl, cyclohexenyl or cyclopentenyl; $R_b$ is hydrogen; $R_a$ is independently selected from hydrogen, —$CH_3$, —$C_2H_5$ or —$(CH_2)_q N(CH_3)_2$; and Ar' is selected from the moieties:

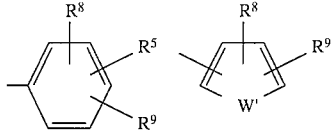

wherein q, x, $R_a$, $R_b$, $R^5$, $R^7$, $R^8$, $R^9$, $R^{11}$, $R^{14}$ and W' are as hereinbefore defined;

$R^{12}$ and $R^{13}$ are independently selected from hydrogen, ($C_1$–$C_3$) lower alkyl, halogen, amino, ($C_1$–$C_3$) lower alkoxy or ($C_1$–$C_3$) lower alkylamino.

The most highly broadly preferred of the compounds are those of the formula:

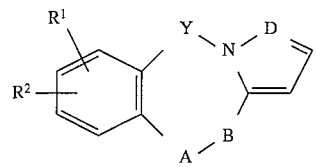

wherein Y is a moiety —$(CH_2)$—;
A–B is a moiety:

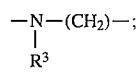

the moiety:

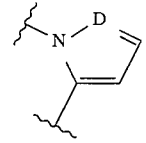

is a five membered aromatic (unsaturated) nitrogen containing heterocyclic ring optionally substituted by halogen, ($C_1$–$C_3$)lower alkyl, and —$(CH_2)_q$—$N(R_b)_2$ wherein D is carbon; q is 1 or 2; $R_b$ is independently selected from hydrogen, —$CH_3$, and $C_2H_5$;

$R^3$ is a moiety of the formula:

wherein Ar is a moiety selected from the group consisting of

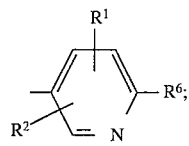

$R^1$ and $R^2$ are independently selected from hydrogen, ($C_1$–$C_3$) lower alkyl, ($C_1$–$C_3$)lower alkoxy and halogen; $R^6$ is selected from; (a) moiety of the formula:

wherein $R_a$ is hydrogen and Ar' is a moiety of the formula:

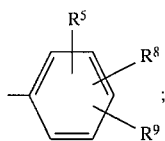

$R^5$ is selected from hydrogen, $(C_1-C_3)$lower alkyl, $(C_1-C_3)$lower alkoxy and halogen; $R^8$ and $R^9$ are independently selected from hydrogen, lower alkyl $(C_1-C_3)$, —S-lower alkyl $(C_1-C_3)$, halogen, —NH-lower alkyl $(C_1-C_3)$, —N—[lower alkyl $(C_1-C_3)]_2$, —OCF$_3$, —OH, —CN, —S—CF$_3$, —NO$_2$, —NH$_2$, O-lower alkyl$(C_1-C_3)$, CF$_3$, and

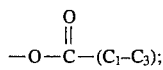

(b) a moiety of the formula:

wherein $R_b$ is hydrogen and J is a moiety:

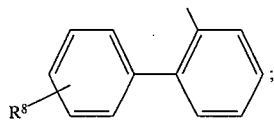

and the pharmaceutically acceptable salts, esters and prodrug forms thereof.

Compounds of this invention may be prepared as shown in Scheme I by reaction of tricyclic derivatives of Formula 3a and 3b with a substituted or unsubstituted 6-nitropyridine-3-carbonyl chloride 4 to give the intermediates 5a and 5b. Reduction of the nitro group in intermediates 5a and 5b gives the 6-aminopyridine derivatives 6a and 6b. The reduction of the nitro group in intermediates 5a and 5b may be carried out under catalytic reduction conditions (hydrogen-Pd/C; Pd/C-hydrazine-ethanol) or under chemical reduction conditions (SnCl$_2$-ethanol; Zn-acetic acid TlCl$_3$) and related reduction conditions known in the art for converting a nitro group to an amino group. The conditions for conversion of the nitro group to the amino group are chosen on the basis of compatability with the preservation of other functional groups in the molecule.

Reaction of compounds of Formula 6a and 6b with aroyl chloride or related activated aryl carboxylic acids in solvents such as chloroform, dichloromethane, dioxane, tetrahydrofuran, toluene and the like in the presence of a tertiary base such as triethylamine and diisopropylethylamine or pyridine and the like, affords the compounds 8a and 8b which are vasopressin antagonists.

Scheme 1

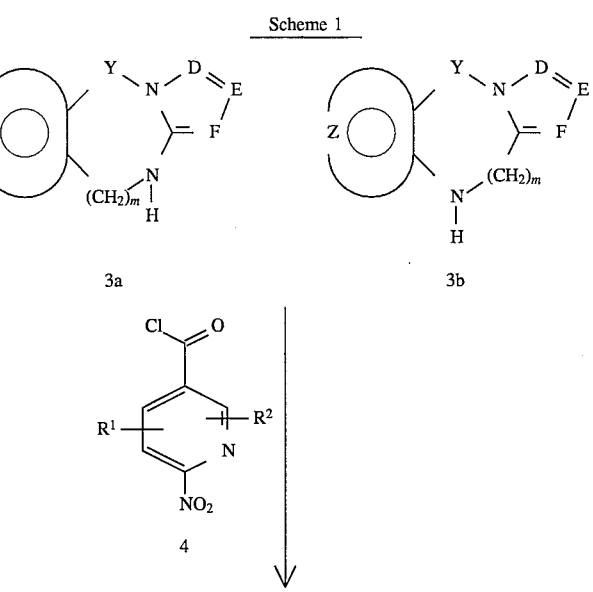

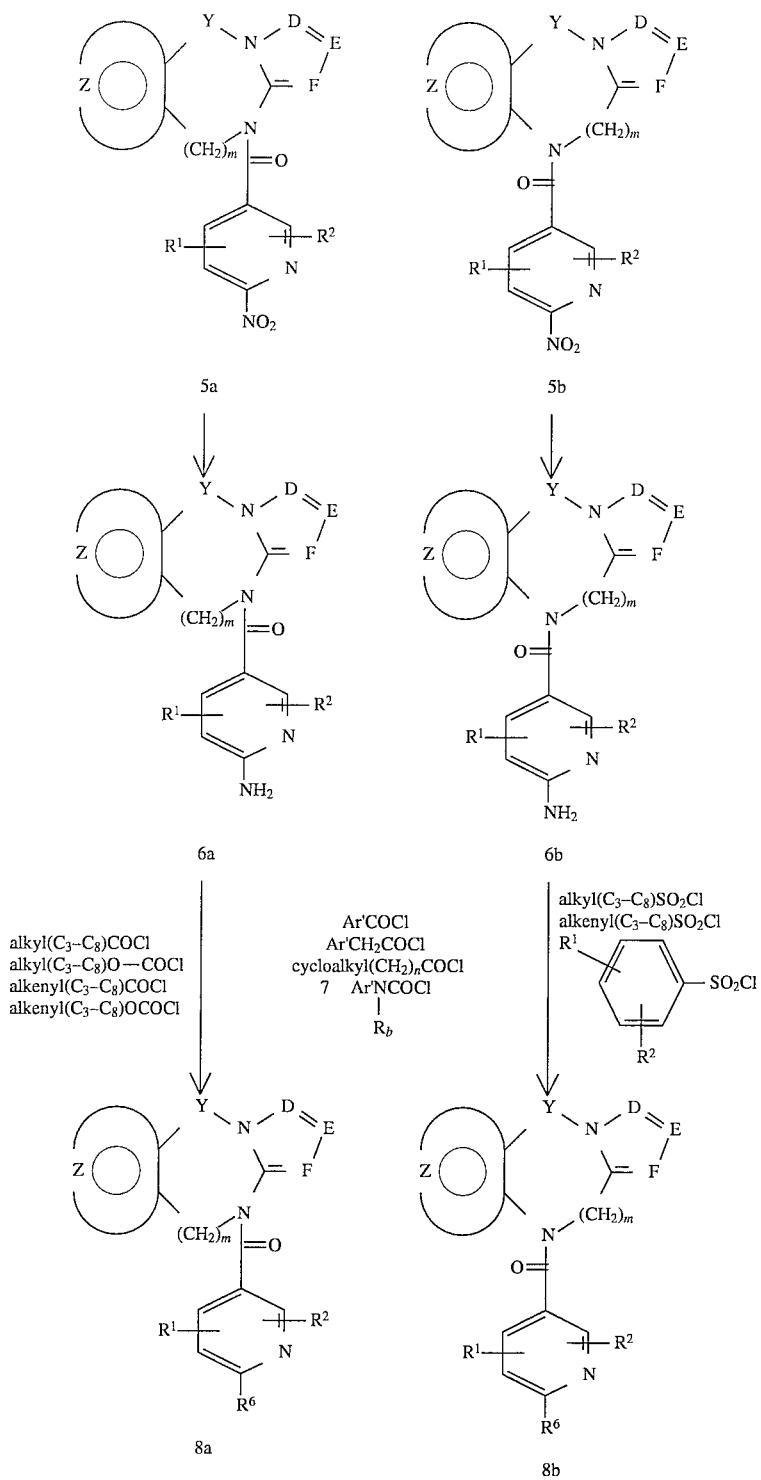
-continued
Scheme 1
$R_6 = $ NHCOAr'; —NHCONAr'; —NHCO(CH$_2$)$_n$cycloalkyl;
           |
           R$_b$
—NHCOCH$_2$Ar', —NHCOalkyl(C$_3$–C$_8$), —NHCO$_2$alkyl(C$_3$–C$_8$),
—NHCOalkenyl(C$_3$–C$_8$), —NHCO$_2$alkenyl(C$_3$–C$_8$),
—NHSO$_2$alkyl(C$_3$–C$_8$), —NHSO$_2$alkenyl(C$_3$–C$_8$), -continued
Scheme 1

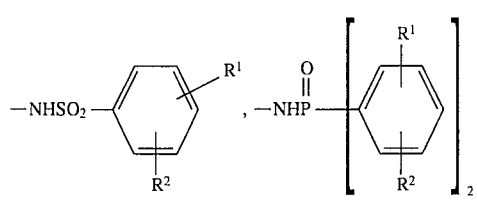

Reaction of tricyclic derivatives of Formula 6a and 6b with either a carbamoyl derivative 9 or a isocyanate derivative 10 gives compounds (Scheme 2) of formula 11a and 11b which are vasopressin antagonists of Formula I wherein $R^6$ is $$-NHCONAr' \atop | \atop R_b$$

Scheme 2

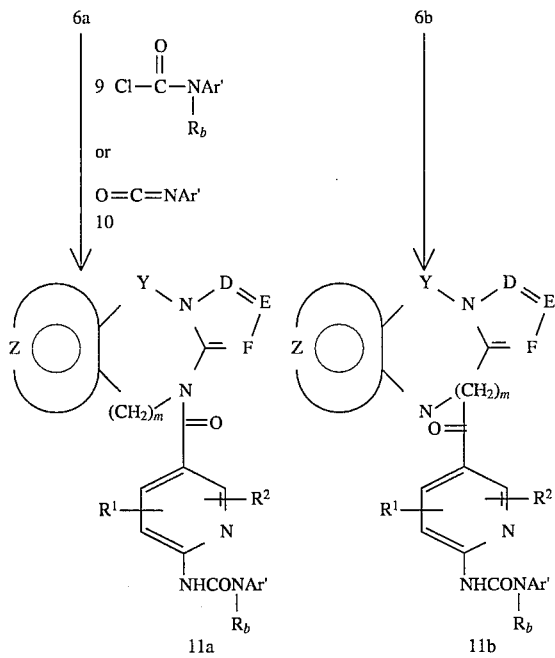

Reaction of tricyclic derivatives of Formula 6a and 6b with arylacetic acids, activated as the acid chlorides 12, anhydrides, mixed anhydrides or activated with known activating reagents, gives compounds 13a and 13b (Scheme 3).

Scheme 3

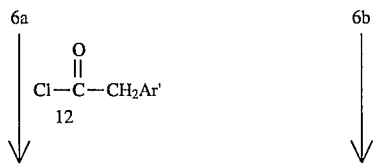

-continued
Scheme 3

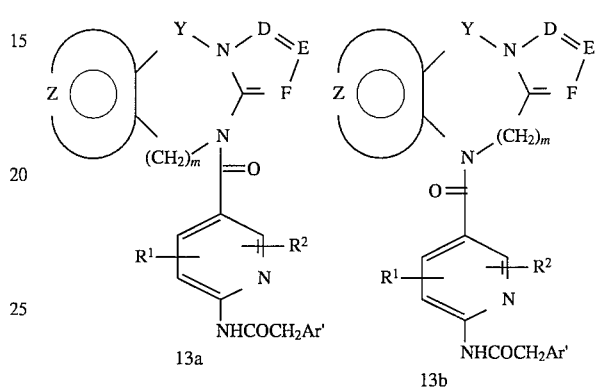

The compounds of Formula I wherein Y, A–B, Z, $R^1$, $R^2$ and $R^3$ are as defined and the Ar moiety of $R^3$ (—COAr) is

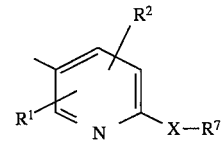

may be prepared, as shown in Scheme 4, by reacting an activated ester of the pyridine-3-carboxylic acid 14 with tricyclic derivatives 3a and 3b. The pyridine-3-carboxylic acids 14 may be activated by preparing the anhydride, a mixed anhydride or reacting with diethyl cyanophosphonate, N,N-carbonyldiimidazole or related peptide coupling reagents. Alternatively, the acid chloride derivatives 15 may be prepared from the acid derivatives 14 and oxalyl chloride or thionyl chloride in an inert solvent. The solvent is removed and the derivative reacted with 3a or 3b at 0° C. to 25° C. in dichloromethane as solvent and a tertiary amine such as triethylamine as a base. The activating reagent for the pyridine-3-carboxylic acids 14 is chosen on the basis of its compatibility with other substituent groups and the reactivity of the activated derivative toward the tricyclic derivatives 3a and 3b to give the vasopressin antagonists 16a and 16b.

Scheme 4

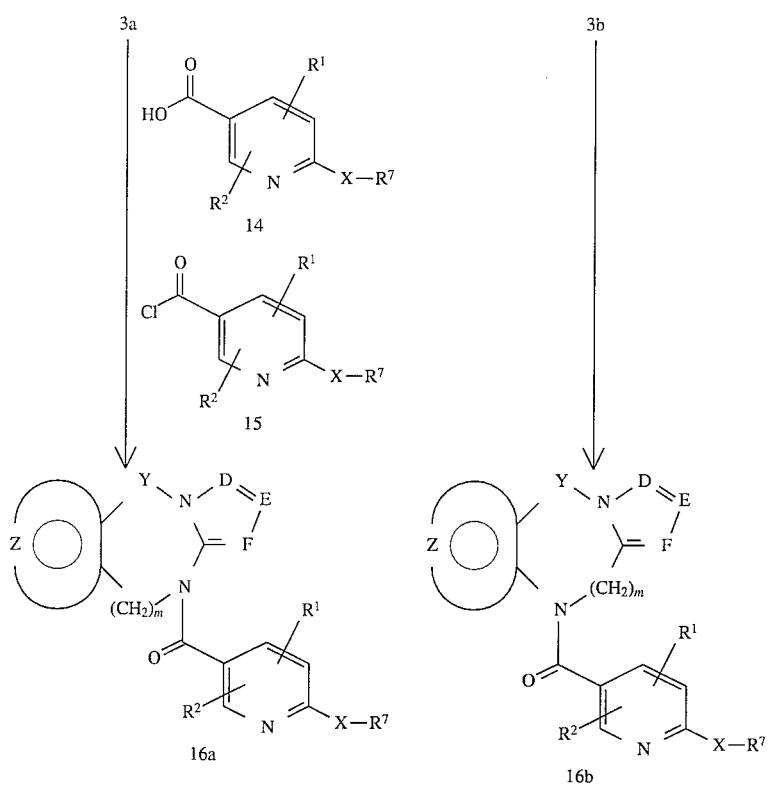

Alternatively, the compounds of Formula I wherein Y, A–B, Z, $R^1$, $R^2$ and $R^3$ are as defined and the Ar moiety of $R^3$ (—COAr) is

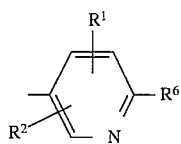

wherein $R^6$ is the moiety

—X—$R^7$ and X is S, NH, $NCH_3$ may be prepared as shown in Scheme 5 by first converting tricyclic derivatives 3a and 3b into the intermediates 17a and 17b and then reacting these intermediates with potassium, sodium, or lithium anions ($R^7$—$X^-$) to give the products 16a and 16b. The symbol $M^+$ is a metal cation derived from reacting a compound $HXR^7$ with a metal hydride (sodium or potassium hydride, for example) or LDA, n-butyl lithium, lithium bis(trimethylsilyl)amide and the like.

The reaction of intermediates 17a and 17b with the moieties $R^7$—$NH_2$ and $R^7$—$NHCH_3$ may also be carried without first forming the corresponding anions. Thus, heating intermediates 17a and 17b with excess $R^7$—$NH_2$ or $R^7$—$NHCH_3$ in an inert solvent or without solvent gives the products 16a and 16b wherein X is NH or $NCH_3$.

Scheme 5

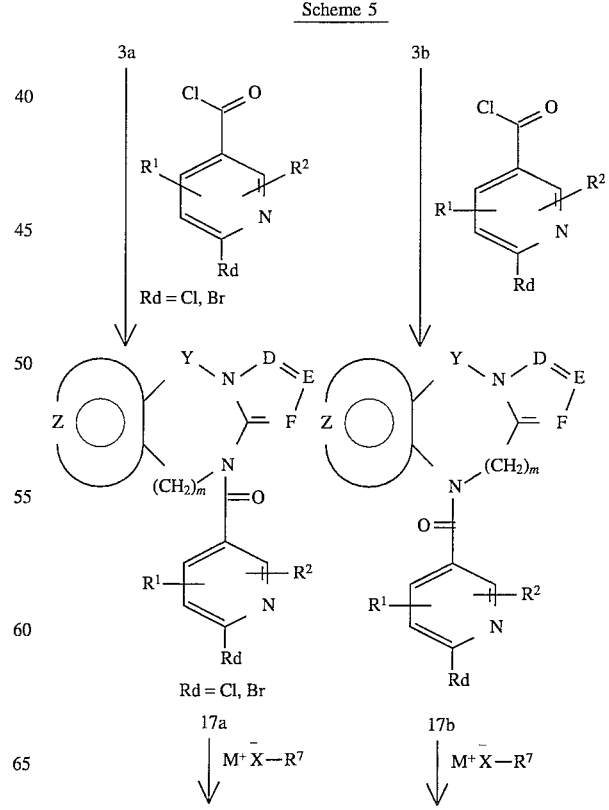

-continued
Scheme 5

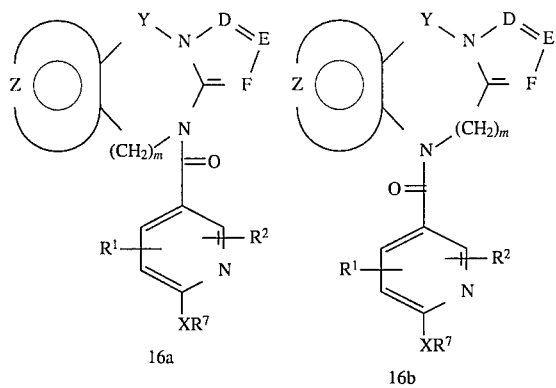

Alternatively, the intermediates 17a and 7b may be converted to the more reactive fluoride derivatives 18a and 18b as shown in Scheme 6. Reaction of the fluoride intermediates 18a and 18b with amines $NH_2R^7$ and $CH_3NHR^7$ gives the 6-aminonicotinoyl derivatives 19a and 19b.

Scheme 6

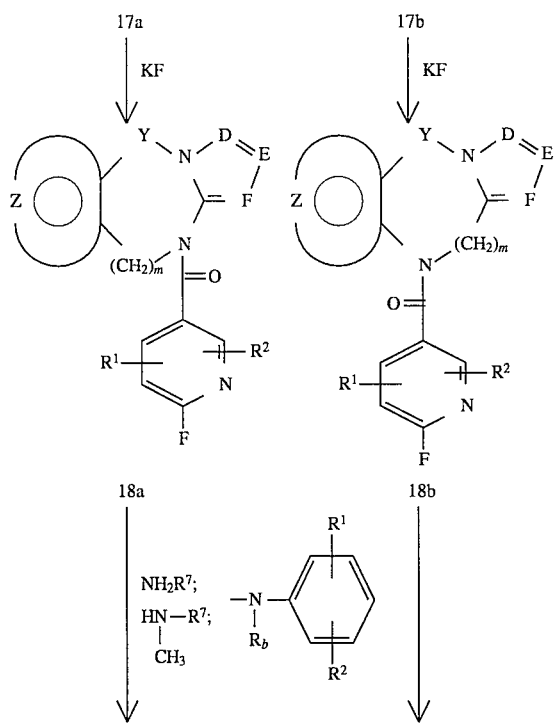

-continued
Scheme 6

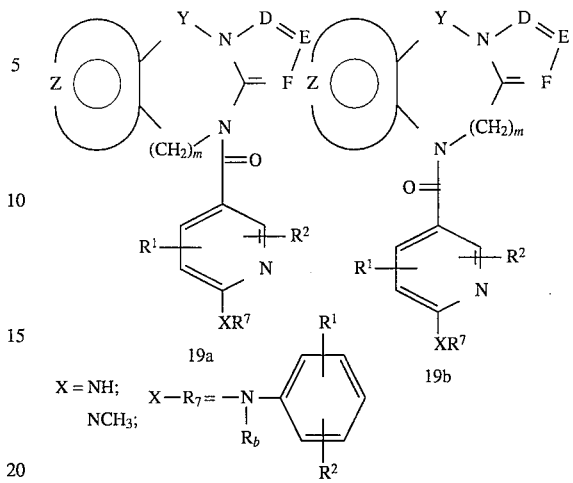

As an alternative method for synthesis of compounds of this invention as depicted in Formula I wherein Y, A–B, D, E, F and Z are as previously described and $R^3$ is

and Ar is

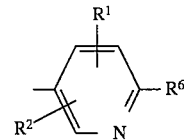

is the coupling of pyridinyl carboxylic acids 20 with the tricyclic derivatives 3a and 3b to give 21a and 21b.

The pyridine carboxylic acids are activated for coupling by conversion to an acid chloride, bromide or anhydride or by first reacting with an activating reagent such as N,N-dicyclocarbodiimide, diethyl cyanophosphonate and related "peptide type" activating reagents. The method of activating the acids 20 for coupling to the tricyclic derivatives 3a and 3b is chosen on the basis of compatibility with other substituent groups in the molecule. The method of choice is the conversion of the 3-pyridinyl carboxylic acids 20 to the corresponding 3-pyridinylcarbonyl chlorides. The 3-pyridinylcarbonyl chlorides 22 may be prepared by standard procedures known in the art, such as reaction with thionyl chloride, oxalyl chloride and the like. The coupling reaction is carried out in solvents such as halogenated hydrocarbons, toluene, xylene, tetrahydrofuran, or dioxane in the presence of pyridine or tertiary bases such as triethylamine and the like (Scheme 7). Alternatively, the 3-pyridinylcarbonyl chlorides 22, prepared from the carboxylic acids 20, may be reacted with derivatives 3a and 3b in pyridine with or without 4-(dimethylamino)pyridine.

In general, when the 3-pyridinyl carboxylic acids 20 are activated with "peptide type" activating reagents, higher temperatures are required than when the 3-pyridinylcarbonyl chlorides are used.

Scheme 7

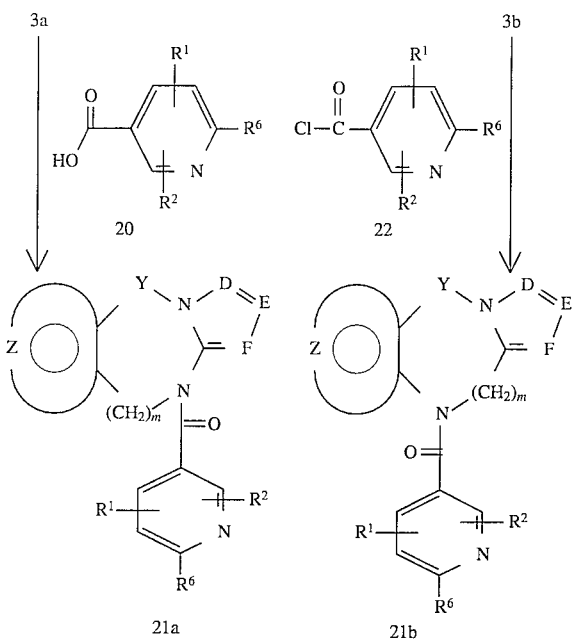

Scheme 8

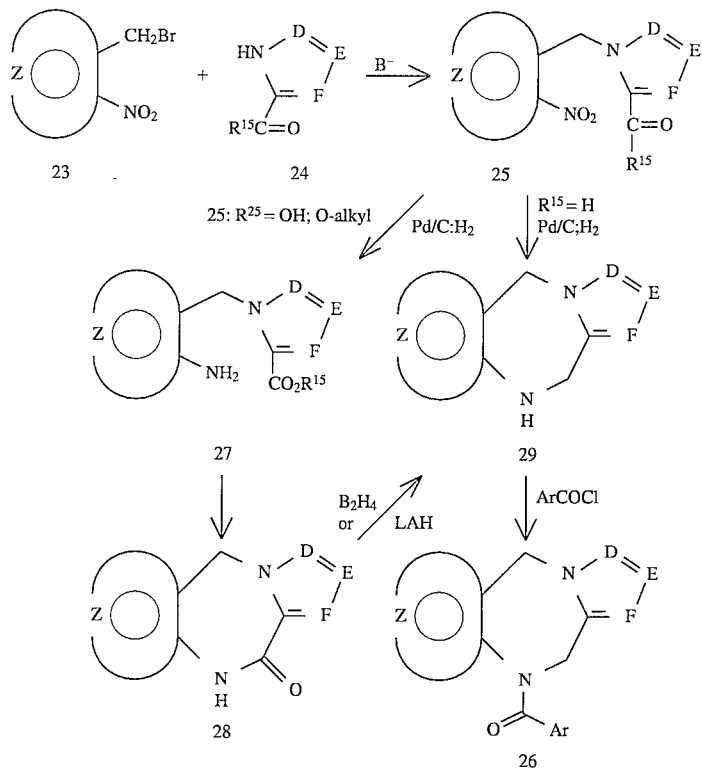

The starting materials 3a and 3b in the foregoing Schemes 1–7 may be prepared as follows. In accordance with Scheme 8, alkylation of heterocycles of structural type 24 with an alkylating moiety such as 23 gives intermediates 25. The heterocycle 24 may contain an α-carboxaldehyde function or an α-carboxylic and/or ester function as shown in Scheme 8. Where the intermediate 25 ($R^{15}$=H) contains an α-carboxaldehyde group, hydrogenation with palladium-on-carbon gives reduction and ring closure in one step to give 29.

In derivatives 25 where $R^{15}$ is an α-carboxylic and/or an α-carboxylic ester function, the intermediate amino acid derivative 27 is first isolated and then ring closed. The ring closure of derivatives 27 may be carried out by heating or by activation of the acid function (27:$R^{15}$=H) for ring closure. The cyclic lactams 28 are conveniently reduced with diborane or lithium aluminum hydride to give intermediates 29. Reaction of tricyclic derivatives 29 with aroyl chlorides (ArCOCl), where Ar is as hereinbefore defined, gives diazepines 26.

Tricyclic derivatives of structural type 36 may be prepared as shown in Scheme 9. Formylation of 32 under known conditions in the literature, such as Viismeier formylation, gives intermediates 35 which on reduction and ring closure affords tricyclics 37.

Where the ring containing the symbol Z is a substituted or unsubstituted phenyl group, the procedure gives 4,5-dihydropyrrolo[1,2-a]-quinoxalines 36. These derivatives 36 and 37 may be reacted with aroyl chlorides (ArCOCl) wherein Ar is as previously defined or with a substituted or unsubstituted 6-nitropyridine-3-carbonyl chloride or with a nitrogen protecting group, such as benzyloxycarbonyl chloride to give compounds 38 and 39. The compounds 38 and 39 may be reacted with chlorine, bromine or halogenating reagents such as N-chlorosuccinimide, N-bromosuccinimide and the like to give compounds 40 and 41 wherein $R^{17}$ is a halogen atom. The derivatives 38 and 39 may be formylated and acetylated to give products 40 and 41 wherein $R^{17}$ is a CHO or a —$COCH_3$ group. Halogenation, formylation and acetylation of derivatives 36 gives 1-substituted 4,5-dihydropyrrolo[1,2-a]quinoxalines. The derivatives 38, 39, 40 and 41 wherein $R^{16}$ is a substituted or unsubstituted 6-nitro-3-pyridinylcarbonyl group are reduced to give the 6-amino-3-pyridinylcarbonyl derivatives 42d and 43d which are reacted with reagents Ar'COCl, Ar'$CH_2$COCl or $$Ar'-\underset{\underset{R_b}{|}}{N}COCl;$$

wherein Ar' and $R_b$ are as previously hereinbefore defined, to give tricyclic diazepines 44 and 45.

Scheme 9

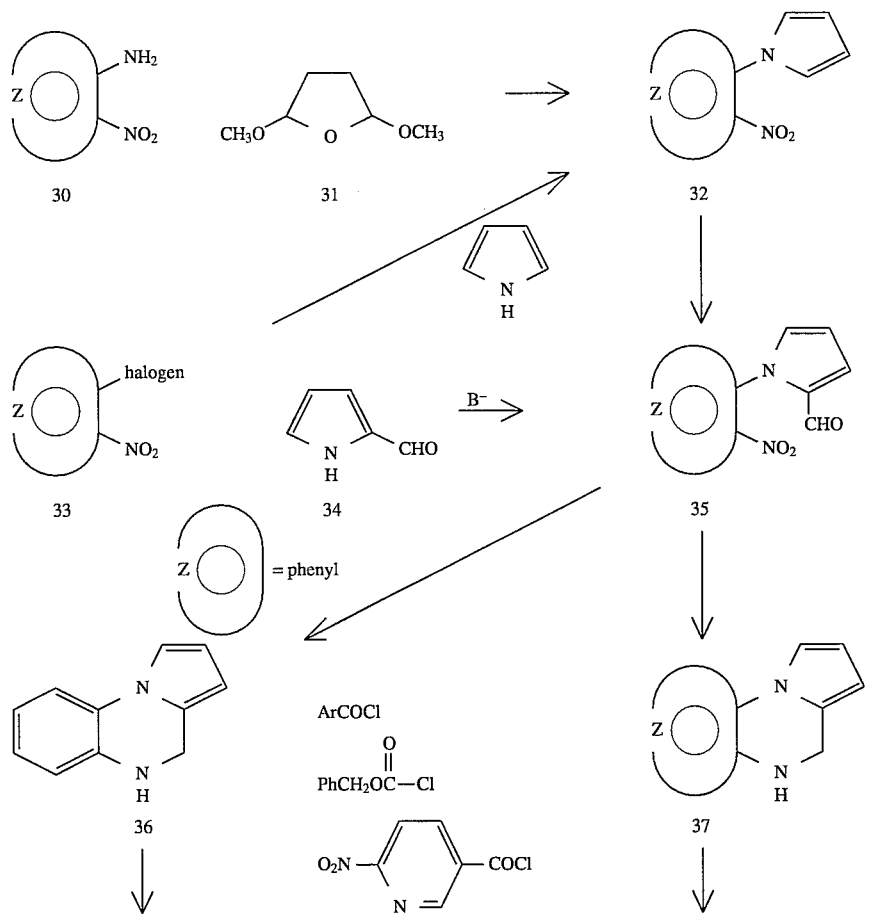

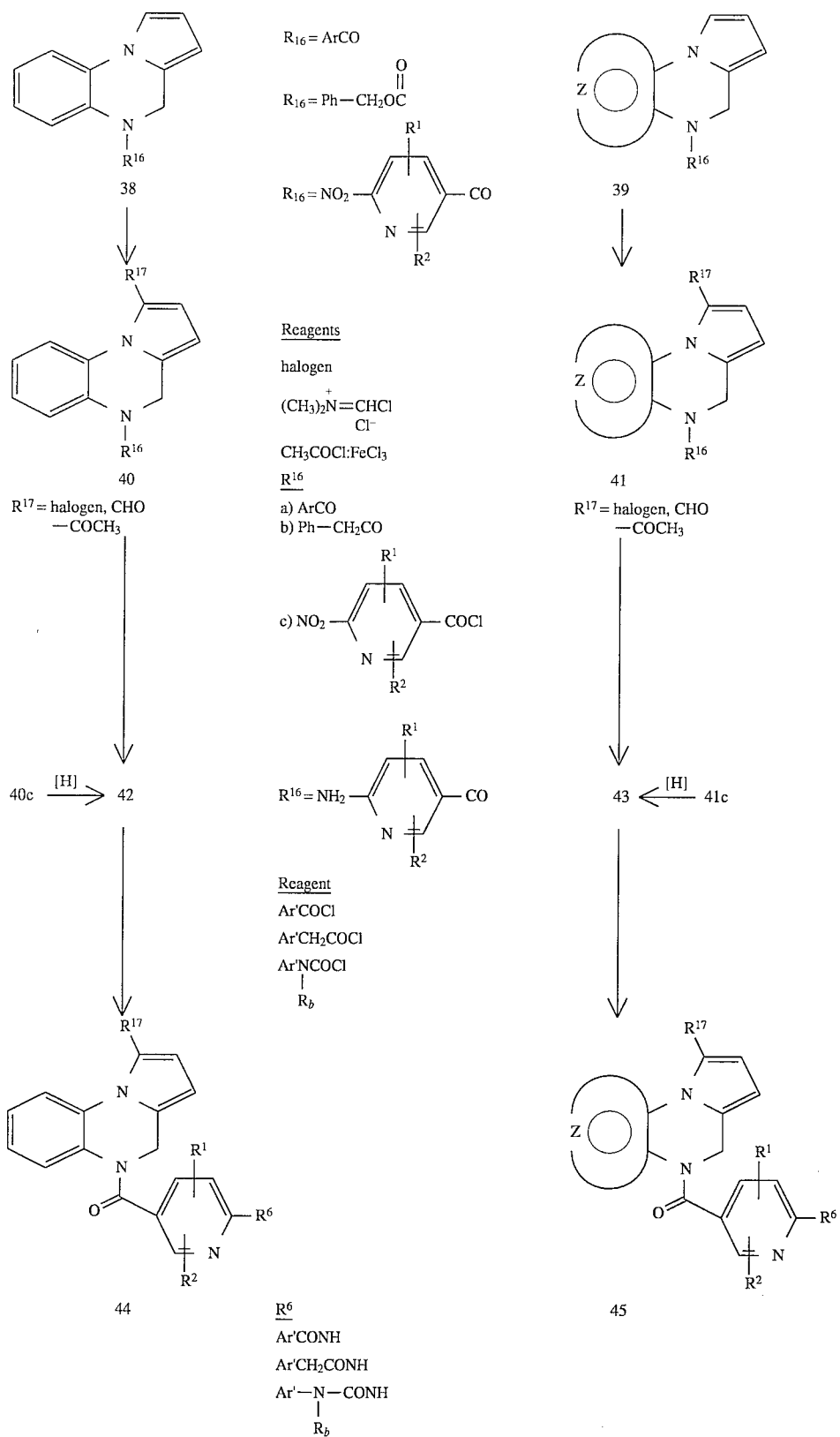

The compounds of this invention wherein $R^3$ is the moiety:

and the Ar group is the moiety:

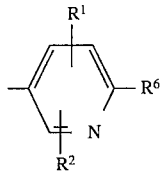

and $R^6$, $R_a$, $R_b$, Y, $R^1$, $R^2$, Z and Ar' are as previously defined and wherein $R^{11}$ is selected from the moieties:

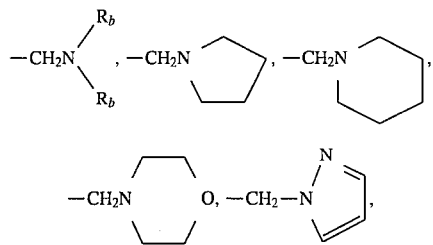

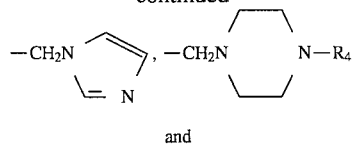

and

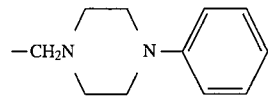

may be synthesized as shown in Scheme 10.

The tricyclic pyrrolodiazepines 46 and 47 are reacted with appropriate amines in the presence of formaldehyde to give the aminomethylene derivatives 48 and 49. The reaction may be carried out with aqueous formaldehyde or its equivalent in the presence of the appropriate amine in a lower alkanol at room temperature or preferably at temperatures of 50° C.–100° C. The aminomethylene derivatives 48 and 49 may be converted to hydrochloride salts or succinic acid and maleic acid salts as well as other pharmaceutically acceptable acid salts.

Scheme 10

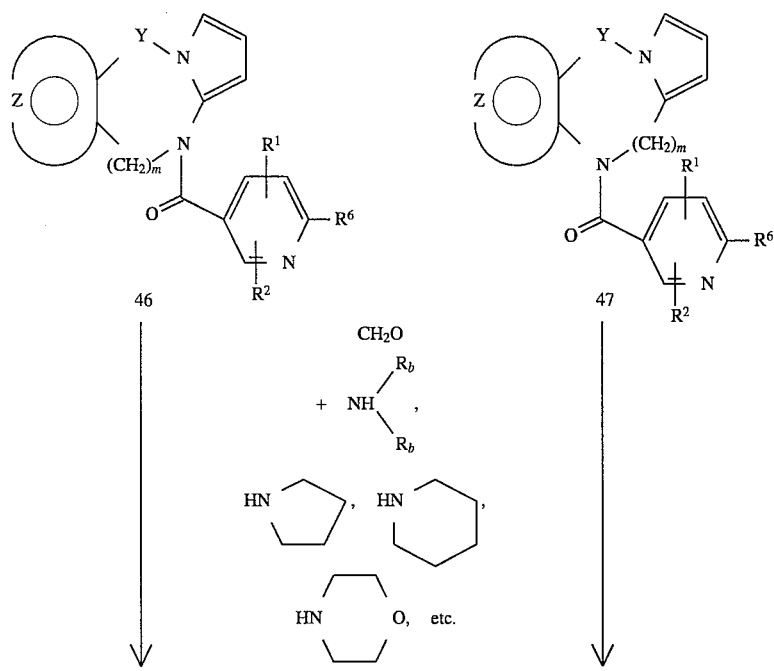

-continued
Scheme 10
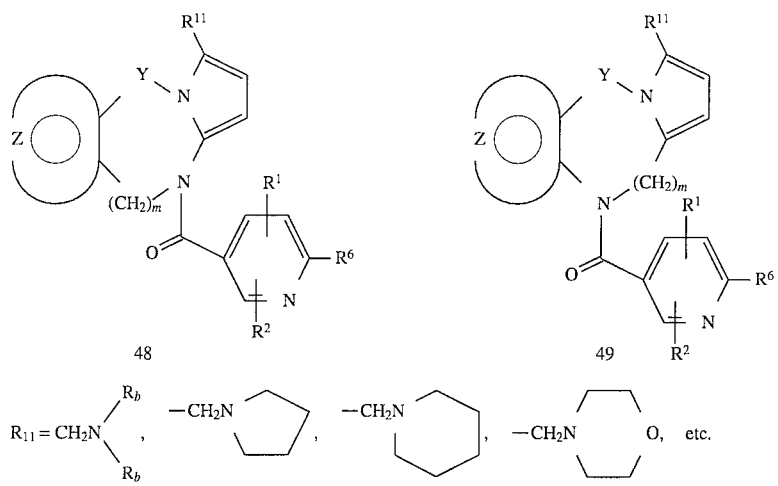
Scheme 11
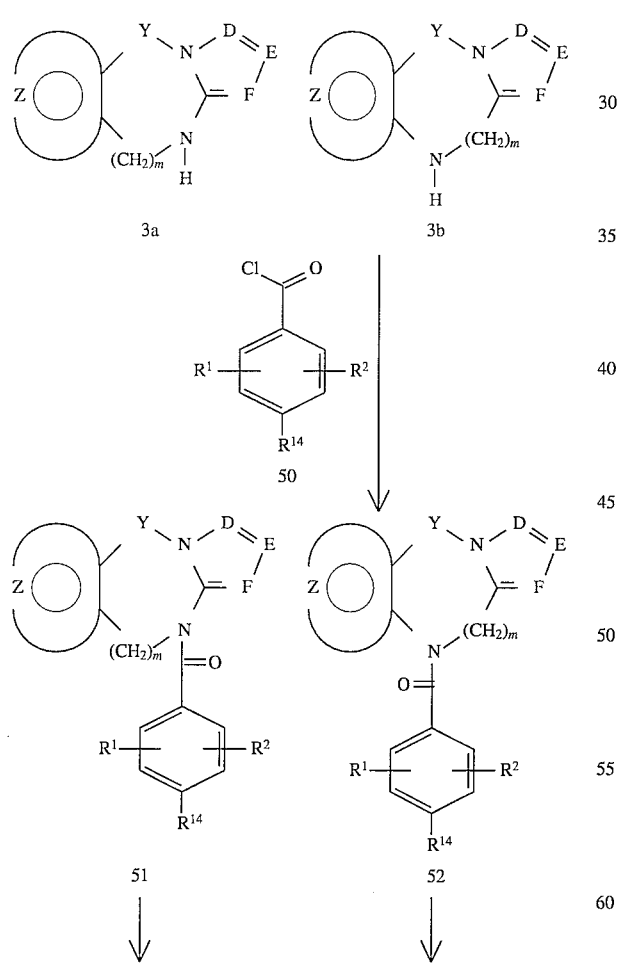
As shown in Scheme 11, reaction of tricyclic derivatives of Formula 3a and 3b with substituted and unsubstituted arylcarbonyl chlorides 50, wherein $R^1$, $R^2$ and $R^{14}$ are hereinbefore defined gives compounds 51 and 52 which are vasopressin antagonists.
Scheme 12
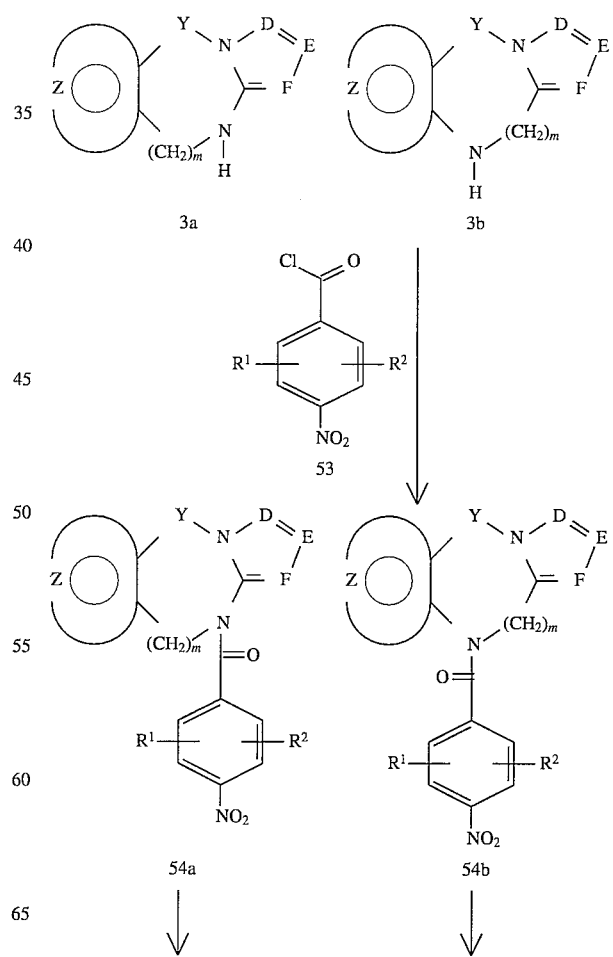

-continued
Scheme 12

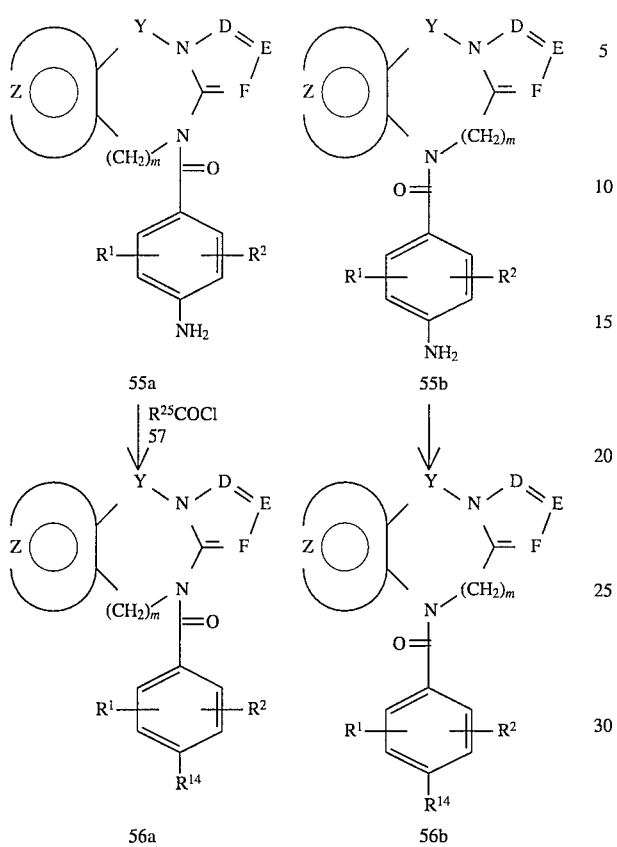

56a 56b

Reaction of tricyclic derivatives of Formula 3a and 3b with a substituted or unsubstituted phenyl carbonyl chloride 53 gives intermediates 54a and 54b. The reduction of the nitro group in intermediates 54a and 54b may be carried out under catalytic reduction conditions (hydrogen-Pd/C; Pd/C-hydrazine-ethanol) or under chemical reduction conditions ($SnCl_2$-ethanol; Zn-acetic acid $TlCl_3$ and related reduction conditions known in the art for converting a nitro group to an amino group. The conditions for conversion of the nitro group to the amino group are chosen on the basis of comparability with the preservation of other functional groups in the molecule.

Reaction of compounds of Formula 55a and 55b with acid chlorides, $R^{25}COCl$ or related activated acid carboxylic acids in solvents such as chloroform, dichloromethane, dioxane, tetrahydrofuran, toluene and the like in the presence of a tertiary base such as triethylamine and diisopropylethylamine or pyridine and the like, affords the compounds 56a and 56b which are vasopressin antagonists.

The acid chlorides $R^{25}COCl$ are those wherein $R^{25}$ is selected from the group

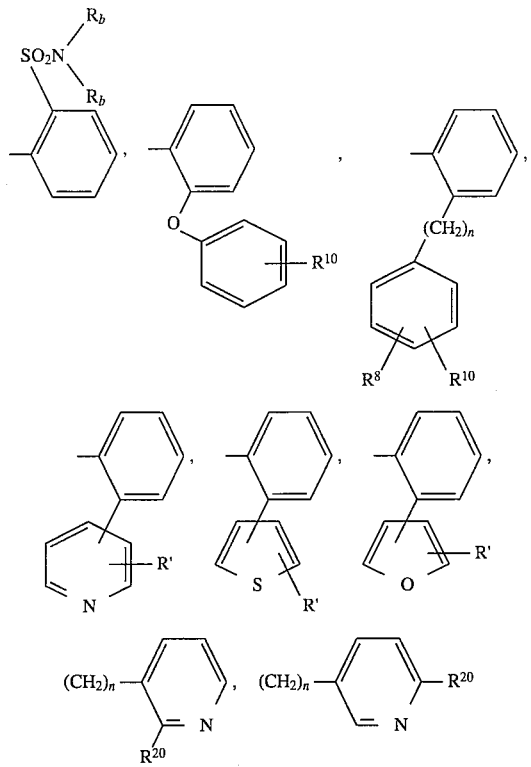

Wherein n is 0 or 1; $R_a$ is hydrogen, —$CH_3$ or —$C_2H_5$; $R^{20}$ is hydrogen, ($C_1$–$C_3$)lower alkyl, ($C_1$–$C_3$)lower alkoxy and halogen; $R^{20}$ is hydrogen, halogen, ($C_1$–$C_3$)lower alkyl, ($C_1$–$C_3$)lower alkoxy, $NH_2$, —$NH(C_1$–$C_3)$-lower alkyl, —N—[($C_1$–$C_3$)lower alkyl]$_2$,

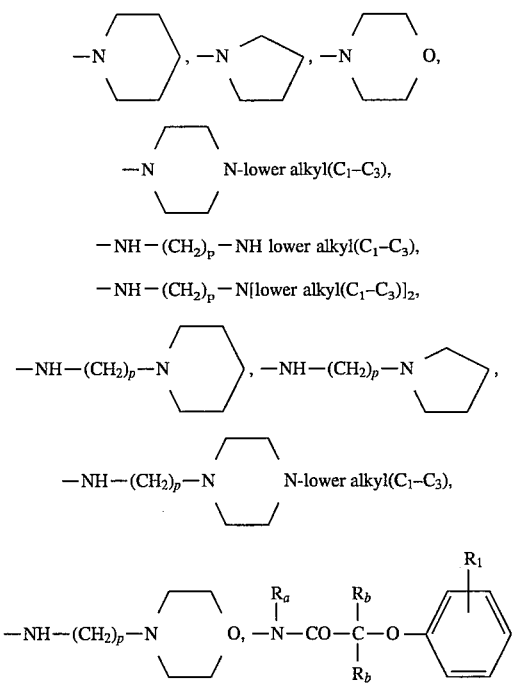

Preparation of some tricyclic diazepines useful for starting materials for the synthesis of compounds of this invention are shown in Schemes 8 and 9. Other tricyclic diazepines are prepared by literature procedures or by methods known in the art or by procedures reported for the synthesis of specific known tricyclic diazepines. These diazepine ring systems discussed below when subjected to reaction conditions shown in Schemes 1, 2, 3, 4, 5, 6, 7, 9 and 10 give the compounds of this invention.

The tricyclic diazepine ring system, 10,11-dihydro-5H-imidazo[2,1-c][1,4]benzodiazepine,

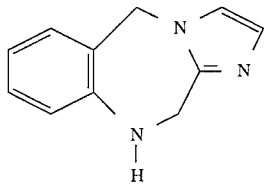

is reported by G. Stefancich, R. Silvestri and M. Artico, *J. Het. Chem.* 30, 529(1993); ring substitution on the same ring system is reported by G. Stefancich, M. Artico, F. Carelli, R. Silvestri, G. deFeo, G. Mazzanti, I. Durando, M. Palmery, *IL Farmaco, Ed. Sc.*, 40, 429(1985).

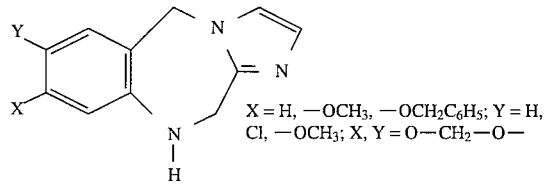

X = H, —OCH₃, —OCH₂C₆H₅; Y = H, Cl, —OCH₃; X, Y = O—CH₂—O—

The synthesis of 9,10-dihydro-4H-furo[2,3-e]pyrrolo[1,2-a][1,4]diazepin-9-one

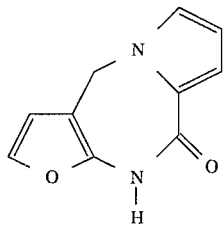

is reported by F. Povazunec, B. Decroix and J. Morel, *J. Het. Chem.* 29, 1507(1992) and is reduced to give the tricyclic heterocycle 9,10-dihydro-4H-furo[2,3-e]pyrrolo[1,2-a][1,4]diazepine.

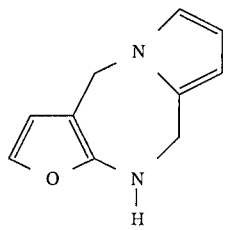

The tricyclic 5,10-dihydro-4H-pyrazolo[5,1-c][1,4]benzodiazepine ring system is reported by L. Cecchi and G. Filacchioni, *J. Het. Chem.*, 20, 871(1983);

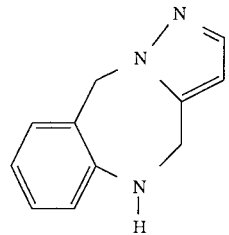

The synthesis of 9-oxo-9,10-dihydro-4H-pyrrolo[1,2-a]thieno[2,3-e][1,4]diazepine is reported by A. Daich and B. Decroix, *Bull. Soc. Chim.* Fr 129, 360(1992);

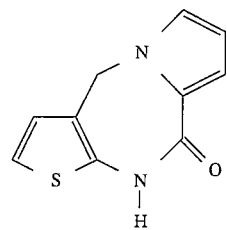

and is reduced with boron-dimethylsulfide to give 9,10-dihydro-4H-pyrrolo [1,2-a]thieno [2,3-e][1,4]diazepine.

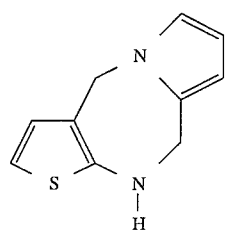

Also reported by A. Daich and B. Decroix is 5-oxo-4,5-dihydropyrrolo[1,2-a]thieno [3,2-e][1,4]diazepine

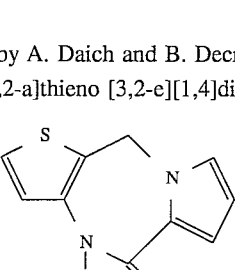

which is also reduced to give 4,10-dihydro-5H-pyrrolo-[1,2-a]thieno[3,2-e][1,4]diazepine

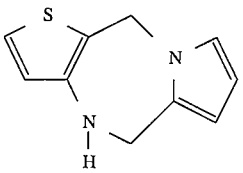

Reported by B. Decroix and J. Morel, *J. Het. Chem.*, 28, 81(1991) are 5H-pyrrolo[1,2-a]thieno[3,2-e][1,4]diazepine;

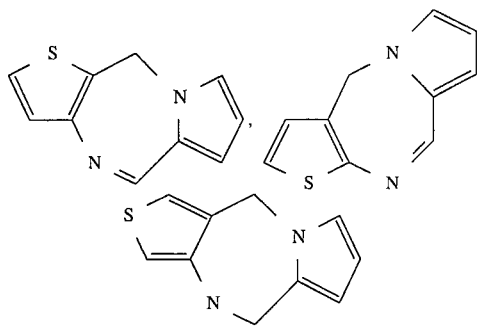

and 4H-pyrrolo[1,2-a]thieno[2,3-e][1,4]diazepine. The 10H-pyrrolo[1,2-a]thieno[3,4-e][1,4]diazepine is reported by A. Daich, J. Morel and B. Decroix, *J. Heterocyclic Chem.*, 31, 341(1994). Reduction by hydrogen-Pd/C or chemical reduction with reagents such as sodium cyanoborohydride and acetic acid gives the dihydro tricyclic heterocycles

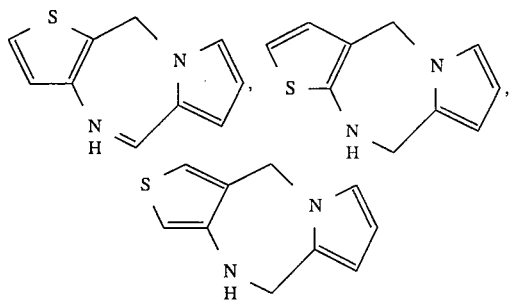

The synthesis of the tricyclic 1,5-benzodiazepine ring system, 6,7-dihydro-5H-pyrrolo[1,2-a][1,5]benzodiazepine, has been reported by F. Chimenti, S. Vomero, R. Giuliano and M. Artico, IL *Farmaco, Ed. Sc.*, 32, 339(1977). Annelated 1,5-benzodiazepines containing five membered rings have been reviewed by A. Chimirri, R. Gitto, S. Grasso, A. M. Monforte, G. Romeo and M. Zappala, *Heterocycles*, 36, No. 3, 604(1993), and the ring system 6,7-dihydro-5H-pyrrolo[1,2-a][1,5]benzodiazepine is described.

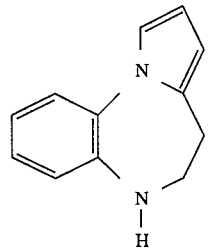

The preparation of 5,6-dihydro-4H-[1,2,4]triazolo-[4,3-a][1,5]benzodiazepin-5-ones from 1,2-dihydro-3H-4-dimethylamino-1,5-benzodiazepin-2-ones has been described by M. DiBroccio, G. Roma, G. Grossi, M. Ghia, and F. Mattioli *Eur. J. Med. Chem*; 26, 489(1991). Reduction of 5,6-dihydro-4H-[1,2,4]triazolo[4,3-a][1,5]benzodiazepin-5-ones with diborane or lithium hydride gives the tricyclic 5,6-dihydro derivatives.

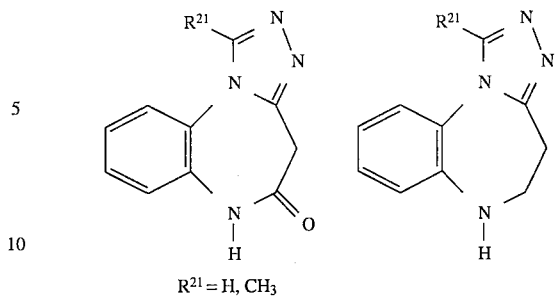

$R^{21}$ = H, $CH_3$

The compounds of this invention and their preparation can be understood further by the following examples, but should not constitute a limitation thereof.

REFERENCE EXAMPLE 1

1-(2-Nitrophenyl)-1H-pyrrole-2-carboxaldehyde

To a solution of 3.76 g of 1-(2-nitrophenyl)pyrrole in 20 ml of N,N-dimethylformamide at 0° C. is added dropwise with stirring 3 ml of phosphorus oxychloride. Stirring is continued for 30 minutes and the reaction mixture is heated at 90° C. for 1 hour. After cooling to room temperature the mixture is treated with crushed ice and the pH adjusted to 12 with 2N sodium hydroxide. The resulting suspension is filtered, washed with water and dried to give 5.81 g of the desired product as a light yellow solid, m.p. 119°–122° C.

REFERENCE EXAMPLE 2

4,5-Dihydro-pyrrolo-[1,2-a]-quinoxaline

To a solution of 1.0 g of 1-(2-nitrophenyl)-1H-pyrrole-2-carboxaldehyde in 40 ml of ethyl alcohol and 40 ml of ethyl acetate, under argon, is added 40 mg of 10% Pd/C. The mixture is hydrogenated at 40 psi for 2 hours and filtered through diatomaceous earth. The filtrate is concentrated in vacuo to a residue which is dissolved in ether and treated with hexanes to give 0.35 g of the desired product as a beige solid, m.p. 108°–110° C.

REFERENCE EXAMPLE 3

N-(2-Nitrobenzoyl)pyrrole-2-carboxaldehyde

To an ice bath cooled solution of 5.6 g of 2-pyrrolecarboxaldehyde in 40 ml of tetrahydrofuran is added 2.4 g of 60% sodium hydride in mineral oil. The temperature elevates to 40° C. After stirring for 20 minutes a solution of 11.0 g of 2-nitrobenzoyl chloride in 20 ml of tetrahydrofuran is added dropwise over 20 minutes. After stirring in the cold for 45 minutes, the reaction mixture is poured into ice water and ether then filtered. The cake is washed with additional ether. The two phase filtrate is separated and the ether layer dried and concentrated in vacuo to give 10 g of a residue as a dark syrup which is scratched with ethanol to give crystals which are collected by filtration, washed with ether and then dried to afford 3.2 g of solid, m.p. 95°–99° C.

REFERENCE EXAMPLE 4

10,11-Dihydro-5H-pyrrolo[2,1-c][1,4]benzodiazepin-5-one

A mixture of 1.5 g of N-(2-nitrobenzoyl)pyrrole-2-carboxaldehyde in 50 ml of ethyl acetate, 2 drops of concentrated HCl and 0.3 g of 10% Pd/C is shaken in a Parr apparatus under hydrogen pressure for 1.75 hours. The mixture is filtered, 0.4 g of 10% Pd/C added and the mixture shaken in a Parr apparatus under hydrogen pressure for 2 hours. The reaction mixture is filtered through diatomaceous earth and the filtrate concentrated in vacuo to give 1.0 g of a yellow oil. The residue is purified on thick layer chromatography plates by elution with 4:1 ethyl acetate:hexane to give 107 mg of the desired product as an oily solid.

REFERENCE EXAMPLE 5

1-(2-Nitrobenzyl)-2-pyrrolecarboxaldehyde

To 5.56 g of 60% sodium hydride in mineral oil, washed three times with hexane, is added 300 ml of N,N-dimethylformamide under argon. The reaction mixture is cooled in an ice-bath and 13.2 g of pyrrole-2-carboxaldehyde is added slowly. The reaction mixture becomes a complete solution and is stirred for an additional 10 minutes. While stirring, 30.0 g of 2-nitrobenzyl bromide is added slowly. After complete addition, the reaction mixture is stirred for 30 minutes, the ice bath is removed and the reaction mixture stirred at room temperature for 24 hours. The N,N-dimethylformamide is concentrated in vacuo to give a residue which is stirred with ice water for 1 hour. The resulting solid is collected, air dried, then vacuum dried to give 30.64 g of the desired product as a tan solid, m.p. 128°–132° C.

REFERENCE EXAMPLE 6

10,11-dihydro-5H-pyrrolo[2,1-c][1,4]benzodiazepine

A mixture of 30.6 g of 1-(2-nitrobenzyl)-2-pyrrolecarboxaldehyde and 3.06 g of 10% Pd/C in 400 ml of ethyl acetate and 400 ml of ethyl alcohol is hydrogenated over 18 hours. The reaction mixture is filtered through diatomaceous earth and the filtrate is treated with activated carbon and filtered through diatomaceous earth. The filtrate is concentrated in vacuo to give a residue which is dissolved in methylene chloride containing ethyl alcohol. The solution is passed through a pad of silica gel and the pad washed with a 7:1 hexaneethyl acetate solution to give 16.31 g of the desired product as solid, m.p. 145°–148° C.

REFERENCE EXAMPLE 7

3-Methylbenzo[b]thiophene-2-acetyl chloride

A mixture of 2.0 g of 3-methylbenzo[b]-thiophene-2-acetic acid and 19.4 ml of thionyl chloride is heated at reflux for 1 hour. The volatiles are evaporated in vacuo to give a residue which is concentrated from toluene three times and dried under vacuum to give 2.25 g of the desired product as a residue.

REFERENCE EXAMPLE 8

4-Chloro-2-methoxybenzoyl chloride

A solution of 2.0 g of 4-chloro-o-anisic acid in 22 ml of thionyl chloride is heated at reflux for 1 hour. The volatiles are evaporated in vacuo to give a residue which is concentrated from toluene three times and dried under vacuum to give 2.0 g of the desired product as a residue.

REFERENCE EXAMPLE 9

2-(Trifluoromethyl)benzoyl chloride

A solution of 2.0 g of o-trifluoromethylbenzoic acid in 21 ml of thionyl chloride is heated at reflux for 1 hour. The volatiles are evaporated in vacuo to give a residue which is concentrated from toluene three times and dried under vacuum to give 2.1 g of the desired product as a residue.

REFERENCE EXAMPLE 10

2-Methylphenylacetyl chloride

A solution of 2.0 g of o-tolylacetic acid in 27 ml of thionyl chloride is heated at reflux for 1 hour. The volatiles are evaporated in vacuo to give a residue which is concentrated from toluene three times and dried under vacuum to give 2.1 g of the desired product as a light brown oil.

REFERENCE EXAMPLE 11

3-Methyl-4-nitro-benzoyl chloride

A mixture of 1.81 g of 3-methyl-4-nitrobenzoic acid and 1.25 g of thionyl chloride in 75 ml of chloroform is heated at reflux under argon for 48 hours. The volatiles are removed in vacuo to a residue which is evaporated with toluene several times in vacuo. The residue is partially dissolved in methylene chloride and filtered free of solids and the filtrate evaporated in vacuo to give 1.47 g of the desired acid chloride.

REFERENCE EXAMPLE 12

1-(o-Nitrobenzyl)-imidazole-2-carboxaldehyde

A 2.0 g portion of sodium hydride (60% in oil) is washed with pentane two times. To the residue is added 110 ml of N,N-dimethylformamide under argon with stirring and external cooling, 4.80 g of 2-imidazole-carboxaldehyde is added and the cooling bath removed. Slight external heating results in a yellow solution. The reaction mixture is chilled in ice and 10.8 g of 2-nitrobenzyl bromide is added. The reaction mixture is stirred at 0° C. for 18 hours. The volatiles are removed in vacuo to a residue which is stirred with ice water, filtered and the cake washed well with water and suction dried to give 10.9 g of the desired product as a solid, m.p. 141°–144° C. MH+ 232.

REFERENCE EXAMPLE 13

10,11-Dihydro-5H-imidazo[2,1-c][1,4]benzodiazepine

A 5.0 g sample of 1-(o-nitrobenzyl)-imidazole-2-carboxaldehyde is dissolved in 150 ml of hot ethyl alcohol, cooled to room temperature and filtered. To the filtrate is added 0.5 g of 10% Pd/C and the mixture hydrogenated at 48 psi for 4 hours. An additional 0.5 g of 10% Pd/C is added and hydrogenation continued for 25 hours at 65 psi. The mixture is filtered through diatomaceous earth and the cake washed with ethyl acetate. The filtrate is evaporated in vacuo to a residue which is dissolved in methylene chloride, treated with activated carbon, filtered through diatomaceous earth and hexanes added to the filtrate at the boil to give 1.86 g of the desired product as a crystalline solid, m.p. 164°–170° C.

REFERENCE EXAMPLE 14

10,11-Dihydro-5H-imidazo[2,1-c][1,4]benzodiazepine

To a suspension of 4 mmol of lithium aluminum hydride in 20 ml of anhydrous tetrahydrofuran is added a 1 mmol solution of 10,11-dihydro-11-oxo-5H-imidazo-[2,1-c][1,4] benzodiazepine and the mixture is refluxed for 24 hours and cooled at 0° C. To the mixture is added dropwise 0.12 ml of water and 6 ml of 1N sodium hydroxide. The mixture is extracted with ethyl acetate and the solvent removed to give the desired product as a solid. Recrystallization from methylene chloride-hexane gives crystals, m.p. 164°–170° C.

REFERENCE EXAMPLE 15

9,10-Dihydro-4H-furo[2,3-e]pyrrolo[1,2-a][1,4]diazepine

To a suspension of 4 mmol of lithium aluminum hydride in 25 ml of anhydrous tetrahydrofuran is added 1 mmol of 9,10-dihydro-4H-furo[2,3-e]pyrrolo[1,2-a][1,4]-diazepin-9-one. The mixture is refluxed for 12 hours and allowed to stand overnight. To the mixture is added dropwise 0.12 ml of water and then 6 ml of 1N sodium hydroxide. The mixture is extracted with ethyl acetate and the extract dried ($Na_2SO_4$). The volatiles are removed in vacuo to give the desired product as a solid.

REFERENCE EXAMPLE 16

9,10-Dihydro-4H-furo[2,3-e[pyrrolo[1,2-a][1,4]diazepine

A solution of 1 mmol of 4H-furo[2,3-e]pyrrolo[1,2-a][1,4]diazepine and 0.2 g of 10% Pd/C in 10 ml of ethanol is hydrogenated for 18 hours. The reaction mixture is filtered through diatomaceous earth and the filtrate is evaporated in vacuo to give the desired product as a solid.

REFERENCE EXAMPLE 17

9,10-Dihydro-4H-pyrrolo[1,2-a]thieno[2,3-e][1,4]diazepine

To a mixture of 7.0 g of 9-oxo-9,10-dihydro-4H-pyrrolo[1,2-a]thieno[2,3-e][1,4]diazepin in 25 ml of anhydrous tetrahydrofuran is added 9 ml of 10 molar boron-dimethylsulfide in tetrahydrofuran. The mixture is refluxed for 6 hours. The solution is cooled to room temperature and 25 ml of methanol added dropwise. The volatiles are removed under vacuum. To the residue is added 100 ml of 2N NaOH. The mixture is refluxed 5 hours and filtered. The solid is extracted with dichloromethane and the extract is washed with 2N citric acid, water and dried ($Na_2SO_4$). The solvent is removed in vacuo to give the desired product as a solid.

REFERENCE EXAMPLE 18

4,10-Dihydro-5H-pyrrolo[1,2-a]thieno[3,2-e][1,4]diazepine

To a suspension of 7.0 g of 5-oxo-4,5-dihydropyrrolo[1,2-a]thieno[3,2-e][1,4]diazepine in 25 ml of anhydrous tetrahydrofuran is added 9 ml of 10M boranedimethylsulfide in tetrahydrofuran. The mixture is refluxed for 6 hours. The solution is cooled to room temperature and 25 ml of methanol added dropwise. The volatiles are removed under vacuum. To the residue is added 100 ml of 2N NaOH. The mixture is refluxed 5 hours and filtered. The solid is extracted with dichloromethane and the extract is washed with 2N citric acid, water and dried ($Na_2SO_4$). The solvent is removed to give a solid.

REFERENCE EXAMPLE 19

5,6-Dihydro-4H-[1,2,4]triazolo[4,3-a][1,5]benzodiazepine

A mixture of 7.0 g of 5,6-dihydro-4H-[1,2,4]triazolo-[4,3-a][1,5]benzodiazepin-5-one in 25 ml of tetrahydrofuran is added 9 ml of 10 M boranedimethylsulfide in tetrahydrofuran. The mixture is refluxed for 6 hours, cooled to room temperature and 25 ml of methanol added dropwise. The volatiles are removed under vacuum and to the residue is added 100 ml of 2N sodium hydroxide. The mixture is refluxed for 5 hours, chilled and extracted with dichloromethane. The extract is washed with 2N citric acid, water and dried ($Na_2SO_4$). The solvent is removed under vacuum to give a solid. The solid is purified by chromatography on silica gel to give the desired product.

REFERENCE EXAMPLE 20

1-(2-Nitrophenyl)-1H-pyrrole-2-carboxaldehyde

A sample of 4.7 g of sodium hydride (60% in oil) is washed with hexane (under argon). To the sodium hydride is added 200 ml of dry N,N-dimethylformamide and the mixture is chilled to 0° C. To the mixture is added 10.11 g of pyrrole-2-carboxaldehyde in small portions. The mixture is stirred 10 minutes and 15.0 g of 1-fluoro-2-nitrobenzene added dropwise. After the addition, the mixture is stirred at room temperature 16 hours and the mixture concentrated (65° C.) under high vacuum. To the residue is added 400 ml of dichloromethane and the mixture washed with 150 ml each of $H_2O$, brine and dried ($Na_2SO_4$). The solvent is removed in vacuo to give a yellow solid. Crystallization from ethyl acetate-hexane (9:1) gives 17.0 g of light yellow crystals, m.p. 119°–122° C.

REFERENCE EXAMPLE 21

4,1-Dihydro-5H-pyrrolo[1,2-a]thieno[3,2-e][1,4]diazepine

To an ice cooled mixture of 2.1 g of pyrrole-2-carboxylic acid and 2.3 g of methyl 3-aminothiophene-2-carboxylate in 40 ml of dry dichloromethane is added 4 g of N,N-dicyclohexylcarbodiimide. The mixture is stirred at room temperature for 3 hours and filtered. The filter cake is washed with dichloromethane and then extracted twice with 60 ml of acetone. The acetone extract is concentrated to dryness to give 0.8 g of solid, m.p. 214°–218° C. To a suspension of the preceding compound (1.19 g) in 20 ml of dry tetrahydrofuran is added 0.2 g of sodium hydride (60% in oil). After the hydrogen evolution, the mixture is stirred and refluxed for 4.5 hours, cooled and poured into ice-water. The precipitated solid is filtered and the solid triturated with petroleum ether (bp 30°–60° C.) to give 0.75 g of 4,10-dihydro-4,10-dioxo-5H-pyrrolo-[1,2-a]thieno[3,2e][1,4]diazepine as a solid, m.p. 280°–290° C. The preceding compound (0.362 g) is added to an ice-water cooled solution of 1M diborane in tetrahydrofuran. The mixture is stirred at room temperature for 65 hours. The solution is concentrated to dryness and ice-water added to the residue. The mixture is acidified with dilute HCl, stirred and then basified with solid NaHCO$_3$. The mixture is filtered to give 0.223 g of a solid (foam) m.p. 80°–85° C.

REFERENCE EXAMPLE 22

10,11-Dihydro-5H-1,2,4-triazolo[3,4-c][1,4]benzodiazepine

A mixture of 2.2 g of 2-cyanoaniline, 2.0 g of methyl bromoacetate and 1.3 g of potassium carbonate in 12 ml of dry N,N-dimethylformamide is heated at 150°–155° C. for 40 minutes. The cooled mixture is poured into ice-water and the mixture filtered to give 2 g of methyl [N-(2-cyanophenyl)amino]acetate as a yellow solid, m.p. 70°–78° C. The preceding compound (2.0 g) is added to a solution of 0.5 g of sodium methoxide in 50 ml of methanol. The mixture is shaken under an atmosphere of hydrogen with the catalyst Raney-Ni for 19 hours. The mixture is filtered through diatomaceous earth and the filtrate evaporated. Water is added to the residue and the mixture filtered to give 2,3,4,5-tetrahydro-1H-1,4-benzodiazepin-3-one as a yellow solid, m.p. 167°–170° C.

A mixture of the preceding compound (1.6 g) and 0.84 g of phosphorus pentasulfide in 10 ml of dry (dried over KOH) pyridine is stirred and heated at 80°–85° C. for 15 minutes. The mixture is poured into water and stirred for 30 minutes. Filtration gives 1.0 g of 1,2,4,5-tetrahydro-3H-1,4-benzodiazepin-3-thione as yellow solid, m.p. 150°–153° C.

The preceding compound (0.5 g) and 0.5 g of N-formylhydrazine in 6 ml of dry n-butanol is refluxed for 16 hours and the solvent removed. The gummy residue is triturated with cold water and the mixture filtered. The solid is triturated with acetone to give 0.19 g of yellow solid, m.p. 232°–237° C.

REFERENCE EXAMPLE 23

4,-Dihydro-6H-[1,2,4]triazolo[4,3-a][1,5]benzodiazepine

A mixture of 2,3,4,5-tetrahydro-1H-1,5-benzodiazepin-2-thione (0.8 g) and 0.80 g of N-formylhydrazine in 8 ml of n-butanol is stirred and refluxed for 18 hours and the solvent removed under vacuum. Ice water is added to the residual solid and the mixture filtered to give 0.312 g of a gray solid, m.p. 162°–165° C.

REFERENCE EXAMPLE 24

4,5-Dihydro-6H-imiidazo[1,2-a][1,5]benzodiazepine

A mixture of 30 g of acrylic acid, 33 g of o-phenylenediamine is heated on a steam bath for 1.5 hours and the cooled black mixture triturated with ice-water. The aqueous phase is decanted and ice and aqueous ammonium hydroxide added to the residue. The mixture is extracted with dichloromethane and the extract concentrated to dryness. The residue is triturated with carbon tetrachloride and filtered. The oily solid is triturated with a small amount of ethanol to give 9.7 g of a solid. Trituration of the solid with ethyl acetate gives 2,3,4,5-tetrahydro-1H-1,5-benzodiazepin-2-one as an impure solid, m.p. 75°–107° C.

A mixture of the preceding compound (11.3 g) and 5.9 g of phosphorus pentasulfide in 70 ml of dry pyridine is stirred and heated at approximately 80° C. for 20 minutes. The mixture is poured into water and the mixture stirred for 30 minutes. Filtration gives 8.6 g of 2,3,4,5-tetrahydro-1H-1,5-benzodiazepin-2-thione as a solid, m.p. 154°–157° C.

A mixture of the preceding compound (0.70 g), 1.0 g of aminoacetaldehyde dimethyl acetal and 15 mg of 4-methylbenzenesulfonic acid monohydrate in 6 ml of dry n-butanol is refluxed for 4 hours and the solvent removed under vacuum. The residue is heated (refluxed) with 10 ml of 3N hydrochloric acid for 55 minutes. Ice is added to the cooled mixture and the mixture made basic with solid NaHCO$_3$. The mixture is extracted with dichloromethane and the extract dried (Na$_2$SO$_4$). The solvent is removed to give an orange syrup which solidified on standing. The oily solid is triturated with acetone to give a light yellow solid (0.185 g) m.p. 119°–122° C.

REFERENCE EXAMPLE 25

1-(2-Nitrophenyl)-2-pyrroleacetic acid, ethyl ester

To a stirred mixture of 1.88 g of 1-(2-nitrophenyl)pyrrole, 4.80 g of ethyl iodoacetate and 2.22 g of FeSO$_4$.7H$_2$O in 40 ml of dimethyl sulfoxide is added dropwise 10 ml of 30% hydrogen peroxide while keeping the reaction mixture at room temperature with a cold water bath. The mixture is stirred at room temperature for one day. An additional 2.4 g of ethyl iodoacetate, 1.1 g of FeSO$_4$.7H$_2$O and 5 ml of 30% hydrogen peroxide is added and the mixture stirred at room temperature for 1 day. The mixture is diluted with water and extracted with diethyl ether. The organic extract is washed with water, brine and dried (Na$_2$SO$_4$). The solvent is removed and the residue (2.12 g) chromatographed on silica gel with ethyl acetate-hexane (1:4) as solvent to give 0.30 g of product as a brown gum.

REFERENCE EXAMPLE 26

6,7-Dihydro-5H-pyrrolo[1,2-a][1,5]benzodiazepin-6-one

To a solution of 0.8 mmol of 1-(2-nitrophenyl)-2-pyrroleacetic acid, ethyl ester in 3 ml of ethanol is added stannus chloride dihydrate (SnCl$_2$.2H$_2$O) in 2 ml of concentrated hydrochloric acid (with cooling in water bath). The mixture is stirred at room temperature for 5 hours and chilled in an ice bath. To the mixture is added slowly saturated sodium carbonate solution. The solid which precipitates is filtered and the solid washed with water and then extracted with ethyl acetate. The ethyl acetate extract is dried (Na$_2$SO$_4$) and the solvent removed to give 0.16 g of solid which is triturated with ether to give 0.11 g of product as an off-white solid.

REFERENCE EXAMPLE 27

6,7-Dihydro-5H-pyrrolo[1,2-a][1,5]benzodiazepine

To a solution of 0.070 g of 6,7-dihydro-5H-pyrrolo[1,2-a][1,5]benzodiazepin-6-one in 2 ml of tetrahydrofuran is added 0.45 ml of a 2.0M solution of diborane-dimethylsulfide in tetrahydrofuran. The mixture is refluxed for 3 hours, poured into water and made basic with 2N NaOH. The tetrahydrofuran is removed under vacuum and the residual aqueous mixture extracted with diethyl ether. The extract is washed with brine, dried ($Na_2SO_4$) and the solvent removed to give 0.065 g of a colorless oil; one spot by thin layer chromatography (silica gel) with ethyl acetate-hexane (1:2) as solvent (Rf 0.81).

REFERENCE EXAMPLE 28

1-[2-Nitro-5-(ethoxycarbonyl)benzyl]-pyrrole-2-carboxaldehyde

To a stirred slurry of 2.2 g of sodium hydride (60% in oil, washed with hexane) in tetrahydrofuran is added at 0° C. a solution of 4.5 g of pyrrole-2-carboxaldehyde in 25 ml of tetrahydrofuran. After the addition is complete, a solution of 15 g of ethyl 4-nitro-3-bromomethylbenzoate in 30 ml of dry tetrahydrofuran is slowly added under nitrogen. The reaction mixture is stirred at 20° C. for 8 hours and carefully quenched with water. The reaction mixture is extracted with chloroform which is washed with water, dried with $Na_2SO_4$ and concentrated in vacuo to give 12 g of the desired product as a solid; mass spectrum ($M^+H$)349.

REFERENCE EXAMPLE 29

1-[2-Nitro-4-(ethoxycarbonyl)benzyl]-pyrrole-2-carboxaldehyde

The conditions of Example 28 are used with ethyl 3-nitro-4-bromomethylbenzoate to give 13.0 g of the desired product as a solid; mass spectrum ($M^+H$)349.

REFERENCE EXAMPLE 30

Ethyl 10,11-Dihydro-5H-pyrrolo[2,1-c][1,4]benzodiazepine-7-carboxylate

A solution of 10.0 g of 1-[2-nitro-5-(ethoxycarbonyl)benzyl]-pyrrole-2-carboxaldehyde in 150 ml of absolute ethanol containing 1.0 g of 10% Pd/C is hydrogenated in a Parr apparatus for 16 hours under 40 psi of hydrogen. The reaction mixture is filtered through a pad of diatomaceous earth and the filtrate concentrated in vacuo to a residue of 5.5 g of the desired product as a solid; mass spectrum ($M^+H$)255.

REFERENCE EXAMPLE 31

Ethyl 10,11-Dihydro-5H-pyrrolo[2,1-c][1,4]benzodiazepine-8-carboxylate

The hydrogenation conditions of ethyl 10,11-dihydro-5H-pyrrolo[2,1-c][1,4]-benzodiazepine-7-carboxylate are used with 1-[2-nitro-4-(ethoxycarbonyl)-benzyl]-pyrrole-2-carboxaldehyde to give 5.0 g of the desired product as a solid; mass spectrum ($M^+H$)255.

REFERENCE EXAMPLE 32

2-Methylfurane-3-carbonyl chloride

A mixture of 4.0 g of methyl-2-methylfurane-3-carboxylate, 30 ml of 2N NaOH and 15 ml methanol is refluxed for 1.5 hours. The solvent is removed under vacuum to give a solid. The solid is extracted with dichloromethane (discarded). The solid is dissolved in water and the solution acidified with 2N citric acid to give a solid. The solid is washed with water and dried to give crystals 1.05 g of crystals of 2-methylfuran-3-carboxylic acid. The preceding compound (0.95 g) and 3 ml of thionyl chloride is refluxed for 1 hour. The solvent is removed, toluene added (20 ml, three times) and the solvent removed to give the product as an oil.

REFERENCE EXAMPLE 33

2-[2-(Tributylstannyl)-3-thienyl]-1,3-dioxolane

To a stirred solution of 15.6 g (0.10 mol) of 2-(3-thienyl)-1,3-dioxolane in 100 ml of anhydrous ether, n-butyl-lithium (1.48N, in hexane, 74.3 ml) is added dropwise under nitrogen at room temperature. After being refluxed for 15 minutes, the reaction mixture is cooled to −78° C. and tri-n-butyltin chloride (34.18 g, 0.105 mol) in 100 ml of dry tetrahydrofuran is added dropwise. After the addition is complete, the mixture is warmed to room temperature and the solvent evaporated. To the oily residue 100 ml of hexane is added, and the resulting precipitate (LiCl) is filtered off. The filtrate is evaporated and the residue distilled at reduced pressure, giving 34.16 g (77%) of the desired product.

REFERENCE EXAMPLE 34

Methyl 6-aminopyridine-3-carboxylate

Dry methanol (400 ml) is cooled in an ice bath and HCl gas is bubbled into the mixture for 25 minutes. To the MeOH-HCl is added 30 g of 6-aminopyridine-3-carboxylic acid and then the mixture is stirred and heated at 90° C. for 2 hours (all the solid dissolved). The solvent is removed under vacuum and the residual solid dissolved in 100 ml of water. The acidic solution is neutralized with saturated sodium bicarbonate (solid separated) and the mixture chilled and filtered to give 30 g of white crystals, m.p. 150°–154° C.

REFERENCE EXAMPLE 35

6-[(5-fluoro-2-methylbenzoyl)amino]pyridine-3-carboxylic acid

To a mixture of 4.5 g of methyl 6-aminopyridine-3-carboxylate and 5.53 ml of triethylamine in 40 ml of dichloromethane (cooled in an ice bath) is added 6.38 g of 5-fluoro-2-methylbenzoyl chloride in 10 ml of dichloromethane. The mixture is stirred at room temperature under argon for 18 hours and an additional 3.4 g of 5-fluoro-2-methylbenzoyl chloride added. After stirring at room temperature for 3 hours, the mixture is filtered to give 3.0 g of methyl 6-[[bis(5-fluoro-2-methylbenzoyl)]amino]pyridine-3-carboxylate. The filtrate is concentrated to dryness and the residue triturated with hexane and ethyl acetate to give an additional 9.0 g of bis acylated compound.

A mixture of 12.0 g of methyl 6-[[bis(5-fluoro-2-methylbenzoyl)]amino]pyridine-3-carboxylate, 60 ml of methanol-tetrahydrofuran (1:1) and 23 ml of 5N NaOH is stirred at room temperature for 16 hours. The mixture is concentrated under vacuum, diluted with 25 ml of water, cooled and acidified with 1N HCl. The mixture is filtered and the solid washed with water to give 6.3 g of the product as a white solid.

As described for Reference Example 35, but substituting the appropriate aroyl chloride, heteroaroyl chloride, cycloalkanoyl chlorides, phenylacetylchlorides and related appropriate acid chlorides, the following 6-[(aroylamino]pyridine-3-carboxylic acids, 6-[(heteroaroyl)amino]pyridine-3-carboxylic acids and related 6(acylated)amino]pyridine-3-carboxylic acids are prepared.

REFERENCE EXAMPLE 36

6-[(3-Methyl-2-thienylcarbonyl)amino]pyridine-3-carboxylic acid

REFERENCE EXAMPLE 37

6-[(2-Methyl-3-thienylcarbonyl)amino]pyridine-3-carboxylic acid

REFERENCE EXAMPLE 38

6-[(3-Methyl-2-furanylcarbonyl)amino]pyridine-3-carboxylic acid

REFERENCE EXAMPLE 39

6-[(2-Methyl-3-furanylcarbonyl)amino]pyridine-3-carboxylic acid

REFERENCE EXAMPLE 40

6-[(3-fluoro-2-methylbenzoyl)amino]pyridine-3-carboxylic acid

REFERENCE EXAMPLE 41

6-[(2-Methylbenzoyl)amino pyridine-3-carboxylic acid

REFERENCE EXAMPLE 42

6-[(2-chlorobenzoyl)amino]pyridine-3-carboxylic acid

REFERENCE EXAMPLE 43

6-[(2-Fluorobenzoyl)amino]pyridine-3-carboxylic acid

REFERENCE EXAMPLE 44

6-[(2-Chloro-4-fluorobenzoyl)amino]pyridine-3-carboxylic acid

REFERENCE EXAMPLE 45

6-[(2,4-Dichlorobenzoyl)amino]pyridine-3-carboxylic acid

REFERENCE EXAMPLE 46

6-[(4-Chloro-2-fluorobenzoyl)amino]pyridine-3-carboxylic acid

REFERENCE EXAMPLE 47

6-[(3,4,5-Trimethoxybenzoyl)amino]pyridine-3-carboxylic acid

REFERENCE EXAMPLE 48

6-[(2,4-Difluorobenzoyl)amino]pyridine-3-carboxylic acid

REFERENCE EXAMPLE 49

6-[(2-Bromobenzoyl)amino]pyridine-3-carboxylic acid

REFERENCE EXAMPLE 50

6-[(2-Chloro-4-nitrobenzoyl)amino]pyridine-3-carboxylic acid

REFERENCE EXAMPLE 51

6-[(Tetrahydrofuranyl-2-carbonyl)amino]pyridine-3-carboxylic acid

REFERENCE EXAMPLE 52

6-[(Tetrahydrothienyl-2-carbonyl)amino]pyridine-3-carboxylic acid

REFERENCE EXAMPLE 53

6-[(Cyclohexylcarbonyl)amino]pyridine-3-carboxylic acid

REFERENCE EXAMPLE 54

6-[(cyclohex-3-enecarbonyl)amino]pyridine-3-carboxylic acid

REFERENCE EXAMPLE 55

6-[(5-Fluoro-2-methylbenzeneacetyl)amino]pyridine-3-carboxylic acid

REFERENCE EXAMPLE 56

6-[(2-Chlorobenzeneacetyl)amino]pyridine-3-carboxylic acid

REFERENCE EXAMPLE 57

6-[(cyclopentylcarbonyl)amino]pyridine-3-carboxylic acid

REFERENCE EXAMPLE 58

6-[(cyclohexylacetyl)amino]pyridine-3-carboxylic acid

REFERENCE EXAMPLE 59

6-[(3-Methyl-2-thienylacetyl)amino]pyridine-3-carboxylic acid

REFERENCE EXAMPLE 60

6-[(2-Methyl-3-thienylacetyl)amino]pyridine-3-carboxylic acid

REFERENCE EXAMPLE 61

6-[(3-Methyl-2-furanylacetyl)amino]pyridine-3-carboxylic acid

EXAMPLE 62

6-[(2-Methyl-3-furanylacetyl)amino]pyridine-3-carboxylic acid

REFERENCE EXAMPLE 63

6-[(3-Methyl-2-tetrahydrothienylacetyl)amino]pyridine-3-carboxylic acid

REFERENCE EXAMPLE 64

6-[(2-Methyl-3-tetrahydrothienylacetyl)amino]pyridine-3-carboxylic acid

REFERENCE EXAMPLE 65

6-[(2,5-Dichlorobenzoyl)amino]pyridine-3-carboxylic acid

REFERENCE EXAMPLE 66

6-[(3,5-Dichlorobenzoyl)amino]pyridine-3-carboxylic acid

REFERENCE EXAMPLE 67

6-[(2-Methyl-4-chlorobenzoyl)amino]pyridine-3-carboxylic acid

REFERENCE EXAMPLE 68

6-[(2,3-Dimethylbenzoyl)amino]pyridine-3-carboxylic acid

REFERENCE EXAMPLE 69

6-[(2-Methoxybenzoyl)amino]pyridine-3-carboxylic acid

REFERENCE EXAMPLE 70

6-[(2-Trifluoromethoxybenzoyl)amino]pyridine-3-carboxylic acid

REFERENCE EXAMPLE 71

6-[(4-Chloro-2-methoxybenzoyl)amino]pyridine-3-carboxylic acid

REFERENCE EXAMPLE 72

6-[[2-(Trifluoromethyl)benzoyl]amino]pyridine-3-carboxylic acid

REFERENCE EXAMPLE 73

6-[(2,6-Dichlorobenzoyl)amino]pyridine-3-carboxylic acid

REFERENCE EXAMPLE 74

6-[(2,6-Dimethylbenzoyl)amino]pyridine-3-carboxylic acid

REFERENCE EXAMPLE 75

6-[(2-Methylthiobenzoyl)amino]pyridine-3-carboxylic acid

REFERENCE EXAMPLE 76

6-[(4-Fluoro-2-(trifluoromethyl)benzoyl)amino]pyridine -3-carboxylic acid

REFERENCE EXAMPLE 77

6-[(2,3-Dichlorobenzoyl)amino]pyridine-3-carboxylic acid

REFERENCE EXAMPLE 78

6-[(4-Fluoro-2-methylbenzoyl)amino]pyridine-3-carboxylic acid

REFERENCE EXAMPLE 79

6-[(2,3,5-Trichlorobenzoyl)amino]pyridine-3-carboxylic acid

REFERENCE EXAMPLE 80

6-[(5-Fluoro-2-chlorobenzoyl)amino]pyridine-3-carboxylic

REFERENCE EXAMPLE 81

6-[(2-Fluoro-5-(trifluoromethyl)benzoyl)amino]pyridine -3-carboxylic acid

REFERENCE EXAMPLE 82

6-[(5-Fluoro-2-methylbenzoyl)amino]pyridine-3-carbonyl chloride

A mixture of 6.2 g of 6-[(5-fluoro-2-methylbenzoyl)amino]pyridine-3-carboxylic acid and 23 ml of thionyl chloride is refluxed for 1 hour. An additional 12 ml of thionyl chloride is added and the mixture refluxed for 0.5 hour. The mixture is concentrated to dryness under vacuum and 30 ml of toluene added to the residue. The toluene is removed under vacuum and the process (add toluene and remove) is repeated to give 7.7 g of crude product as a solid.

As described for Reference Example 82, the following 6-(acyl)amino)pyridine-3-carbonyl chlorides are prepared.

REFERENCE EXAMPLE 83

6-[3-Methyl-2-thienylcarbonyl)amino]pyridine-3-carbonyl chloride

REFERENCE EXAMPLE 84

6-[(2-Methyl-3-thienylcarbonyl)amino]pyridine-3-carbonyl chloride

REFERENCE EXAMPLE 85

6-[(3-Methyl-2-furanylcarbonyl)amino]pyridine-3-carbonyl chloride

REFERENCE EXAMPLE 86

6-[(2-Methyl-3-furanylcarbonyl)amino]pyridine-3-carbonyl chloride

REFERENCE EXAMPLE 87

6-[(3-Fluoro-2-methylbenzoyl)amino]pyridine-3-carbonyl chloride

REFERENCE EXAMPLE 88

6-[(2-Methylbenzoyl)amino]pridine-3-carbonyl chloride

REFERENCE EXAMPLE 89

6-[(2-Chlorobenzoyl)amino]pyridine-3-carbonyl chloride, white crystals

REFERENCE EXAMPLE 90

6-[(2-Fluorobenzoyl)amino]pyridine-3-carbonyl chloride

REFERENCE EXAMPLE 91

6-[(2-Chloro-4-fluorobenzoyl)amino]pyridine-3-carbonyl chloride

REFERENCE EXAMPLE 92

6-[(2,4-Dichlorobenzoyl)amino]pyridine-3-carbonyl chloride

REFERENCE EXAMPLE 93

6-[(4-Chloro-2-fluorobenzoyl)amino]pyridine-3-carbonyl chloride

REFERENCE EXAMPLE 94

6-[(3,4,5-Trimethoxybenzoyl)amino]pyridine-3-carbonyl chloride

REFERENCE EXAMPLE 95

6-[(2,4-Difluorobenzoyl)amino]pyridine-3-carbonyl chloride

REFERENCE EXAMPLE 96

6-[(2-Bromobenzoyl)amino]pyridine-3-carbonyl chloride

REFERENCE EXAMPLE 97

6-[(2-Chloro-4-nitrobenzoyl)amino]pyridine-3-carbonyl chloride

REFERENCE EXAMPLE 98

6-[(Tetrahydrofuranyl-2-carbonyl)amino]pyridine-3-carbonyl chloride

REFERENCE EXAMPLE 99

6-[(Tetrahydrothienyl-2-carbonyl)amino]pyridine-3-carbonyl chloride

REFERENCE EXAMPLE 100

6-[(Cyclohexylcarbonyl)amino]pyridine-3-carbonyl chloride

REFERENCE EXAMPLE 101

6-[(Cyclohex-3-enecarbonyl)amino]pyridine-3-carbonyl chloride

REFERENCE EXAMPLE 102

6-[(2-Methylbenzeneacetyl)amino]pyridine-3-carbonyl chloride

REFERENCE EXAMPLE 103

6-[(2-Chlorobenzeneacetyl)amino]pyridine-3-carbonyl chloride

REFERENCE EXAMPLE 104

6-[(Cyclopentylcarbonyl)amino]pyridine-3-carbonyl chloride

REFERENCE EXAMPLE 105

6-[(Cyclohexylacetyl)amino]pyridine-3-carbonyl chloride

REFERENCE EXAMPLE 106

6-[(3-Methyl-2-thienylacetyl)amino]pyridine-3-carbonyl chloride

REFERENCE EXAMPLE 107

6-[(2-Methyl-3-thienylacetyl)amino]pyridine-3-carbonyl chloride

REFERENCE EXAMPLE 108

6-[(3-Methyl-2-furanylacetyl)amino]pyridine-3-carbonyl chloride

REFERENCE EXAMPLE 109

6-[(2-Methyl-3-furanylacetyl)amino]pyridine-3-carbonyl chloride

REFERENCE EXAMPLE 110

6-[(2-Methyl-5-flUorobenzeneacetyl)amino]pyridine-3-carbonyl chloride

REFERENCE EXAMPLE 111

6-[(3-Methyl-2-tetrahydrothienylacetyl)amino]pyridine-3-carbonyl chloride

REFERENCE EXAMPLE 112

6-[(2-Methyl-3-tetrahydrothienylacetyl)amino]pyridine-3-carbonyl chloride

REFERENCE EXAMPLE 113

6-[(2,5-Dichlorobenzoyl)amino]pyridine-3-carbonyl chloride

REFERENCE EXAMPLE 114

6-[(3,5-Dichlorobenzoyl)amino]pyridine-3-carbonyl chloride

REFERENCE EXAMPLE 115

6-[(2-Methyl-4-chlorobenzoyl)amino]pyridine-3-carbonyl chloride

REFERENCE EXAMPLE 116

6-[(2,3-Dimethylbenzoyl)amino]pyridine-3-carbonyl chloride

REFERENCE EXAMPLE 117

6-[(2-Methoxybenzoyl)amino]pyridine-3-carbonyl chloride

REFERENCE EXAMPLE 118

6-[(2-Trifluoromethoxybenzoyl)amino]pyridine-3-carbonyl chloride

REFERENCE EXAMPLE 119

6-[(4-Chloro-2-methoxybenzoyl)amino]pyridine-3-carbonyl chloride

REFERENCE EXAMPLE 120

6-[[2-(Trifluoromethyl)benzoyl]amino]pyridine-3-carbonyl chloride

REFERENCE EXAMPLE 121

6-[(2,6-Dichlorobenzoyl)amino]pyridine-3-carbonyl chloride

REFERENCE EXAMPLE 122

6-[(2,6-Dimethylbenzoyl)amino]pyridine-3-carbonyl chloride

REFERENCE EXAMPLE 123

6-[(2-Methylthiobenzoyl)amino]pyridine-3-carbonyl chloride

REFERENCE EXAMPLE 124

6-[(4-Fluoro-2-(trifluoromethyl)benzoyl)amino]pyridine-3-carbonyl chloride

REFERENCE EXAMPLE 125

6-[(2,3-Dichlorobenzoyl)amino]pyridine-3-carbonyl chloride

REFERENCE EXAMPLE 126

6-[(4-Fluoro-2-methylbenzoyl)amino]pyridine-3-carbonyl chloride

REFERENCE EXAMPLE 127

6-[(2,3,5-Trichlorobenzoyl)amino]pyridine-3-carbonyl chloride

REFERENCE EXAMPLE 128

6-[(5-Fluoro-2-chlorobenzoyl)amino]pyridine-3-carbonyl chloride

REFERENCE EXAMPLE 129

6-[(2-Fluoro-5-(trifluoromethyl)benzoyl)amino]pyridine-3-carbonyl chloride

REFERENCE EXAMPLE 130

1-(3-Nitro-2-pyridinyl)-1H-pyrrole-2-carboxaldehyde

A sample (3.6 g) of sodium hydride (60% in oil) is washed with hexane under argon. To the sodium hydride is added 100 ml of dry N,N-dimethylformamide. The mixture is cooled in an ice bath and 7.8 g of 1H-pyrrole-2-carboxaldehyde is added in small portions. After the addition the cooled mixture is stirred for 15 minutes and 13.0 g of 2-chloro-3-nitropyridine is added. The mixture is heated at 120° C. for 16 hours. The solvent is removed under vacuum at 80° C. and to the dark residue is added 200 ml of ethyl acetate. The mixture is filtered and to the filtrate is added 100 ml of water. The mixture is filtered through diatomaceous earth and then filtered through a thin pad of hydrous magnesium silicate. The filtrate is diluted with water, the organic layer separated, washed 2 times with 100 ml of water and once with 100 ml of brine and then dried (Na$_2$SO$_4$). The solvent is removed under vacuum to give 16 g of solid. The solid is chromatographed on a silica gel column with hexane-ethyl acetate (2:1) as solvent to give crystals which are recrystalizzed from ethyl acetate-hexane (97:3) to give 8.5 g of product as crystals, m.p. 122°–125° C.

REFERENCE EXAMPLE 131

5,6-Dihydropyrido[3,2-e]pyrrolo[1,2-a]pyrazine

To a suspension of 8.0 g of 1-(3-nitro-2-pyridinyl)-1H-pyrrole-2-carboxaldehyde in 150 ml of ethyl acetate is added 800 mg of 10% Pd/C. The mixture is shaken in a Parr hydrogenator for 3 hours and then filtered through diatomaceous earth. The filtrate is concentrated under vacuum to give 8.5 g of solid. The solid is purified by chromatography over silica gel with solvent hexane-ethyl acetate (2:1) as solvent to give 2.6 g of product as white crystals, m.p. 92°–94° C. and 1.6 g of pyrido[3,2-a]pyrrolo[1,2-a]pyrazine as tan needles, m.p. 88° C. to 90° C.

As described for Reference Example 35, the following bis acylated products (Table A) are prepared and purified by silica gel chromatography. These compounds are then hydrolysed to the acids as described in Example 35 (Table B).

TABLE A

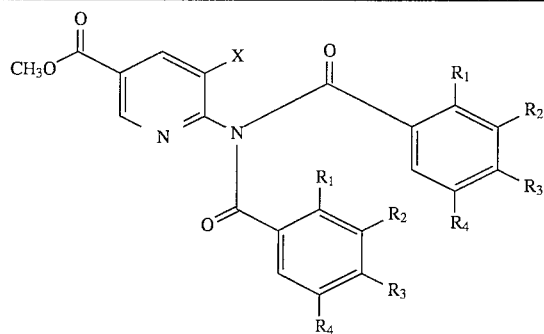

| Ref. Ex No. | $R_1$ | $R_2$ | $R_3$ | $R_4$ | X | $M^+$ |
|---|---|---|---|---|---|---|
| 132 | $CH_3$ | H | H | H | H | 388 |
| 133 | $CH_3$ | H | H | F | H | 424 |
| 134 | $CH_3$ | F | H | H | H | 426 |
| 135 | H | $OCH_3$ | $OCH_3$ | $OCH_3$ | H | 540 |
| 136 | Cl | H | H | H | H | 430 |
| 137 | F | H | F | H | H | 396 |
| 138 | Br | H | H | H | H | 520 |
| 139 | Cl | H | F | H | H | 412 |
| 140 | Ph | H | H | H | H | 512 |
| 142 | Cl | H | H | Br | H | 474 |
| 143 | $CH_3$ | H | H | F | Br | |
| 144 | $CH_3$ | H | H | H | Br | 468 |

$M^+$ is molecular ion found from FAB mass spectrum

TABLE B

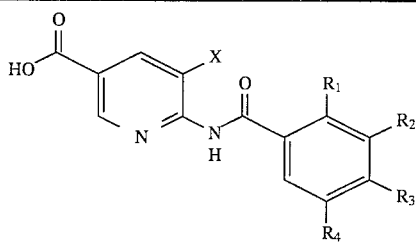

| Ref. Ex No. | $R_1$ | $R_2$ | $R_3$ | $R_4$ | X | $M^+$ |
|---|---|---|---|---|---|---|
| 145 | $CH_3$ | H | H | H | H | 256 |
| 146 | $CH_3$ | H | H | F | H | 274 |
| 147 | $CH_3$ | F | H | H | H | 274 |
| 148 | H | $OCH_3$ | $OCH_3$ | $OCH_3$ | H | 332 |

TABLE B-continued

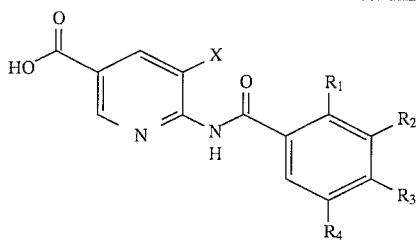

| Ref. Ex No. | $R_1$ | $R_2$ | $R_3$ | $R_4$ | X | $M^+$ |
|---|---|---|---|---|---|---|
| 149 | Cl | H | H | H | H | 276 |
| 150 | F | H | F | H | H | 278 |
| 151 | Br | H | H | H | H | 322 |
| 152 | Cl | H | F | H | H | 294 |
| 153 | Ph | H | H | H | H | 318 |
| 154 | Cl | H | H | Br | H | 356 |
| 155 | $CH_3$ | H | H | F | Cl | |
| 156 | $CH_3$ | H | H | H | Br | 336 |

$M^+$ is molecular ion found from FAB mass spectrum.

REFERENCE EXAMPLE 157

6-Amino-5-bromopyridine-3-carboxylic acid

To a stirred solution of 6-aminonicotinic acid (13.8 g, 0.1 mole) in glacial acetic acid (100 ml), bromine (16 g, 5 ml, 0.1 mole) in acetic acid (20 ml) is added slowly. The reaction mixture is stirred for 8 hours at room temperature and the acetic acid is removed under reduced pressure. The yellow solid residue is dissolved in water and carefully neutralized with 30% $NH_4OH$. The separated solid is filtered and washed with water to give 18 g of solid; mass spectrum: 218 ($M^+$).

REFERENCE EXAMPLE 158

Methyl 6-amino-5-bromopyridine-3-carboxylate

6-Amino-5-bromopyridine-3-carboxylic acid (10 g, 50 mmol) is dissolved in saturated methanolic HCl (100 ml) and refluxed for 24 hours. The solvent, methanol, is removed under reduced pressure and the residue is dis-solved in ice cold water. The aqueous solution is neutralized with 0.1N NaOH and the solid which separates is filtered; washed well with water and air dried to yield 10 g of product as a solid: mass spectrum 231 ($M^+$).

REFERENCE EXAMPLE 159

10-[[6-Chloro-3-pyridinyl]carbonyl]-10,11-dihydro-5H-pyrrolo[2,1-c][1,4]benzodiazepine To a mixture of 1.84 g of 10,11-dihydro-5H-pyrrolo[2,1-c][1,4]benzodiazepine and 1.52 g of triethylamine in 20 ml of dichloromethane is added a solution of 2.11 g of 6-chloronicotinyl chloride in 5 ml of dichloromethane. The mixture is stirred at room temperature for 2 hours and quenched with 30 ml of 1N sodium hydroxide. The mixture is diluted with 20 ml of dichloromethane and the organic layer separated. The organic layer is washed twice with 20 ml of 1N sodium hydroxide, washed with brine and dried ($Na_2SO_4$). The solvent is removed under vacuum and the residue triturated with ether to give 3.22 g of white solid; mass spectrum (CI) 324 ($M^+H$).

REFERENCE EXAMPLE 160

10-[[6-[(2-dimethylaminoethyl)amino]-3-pyridinyl]carbonyl]-10,11-dihydro-5H-pyrrolo[2,1-c][1,4-benzodiazepine A mixture of 10-[[6-chloro-3-pyridinyl]carbonyl]-10,11-dihydro-5H-pyrrolo[2,1-c][1,4]benzodiazepine (3.2 g), $K_2CO_3$ (5 g) and the 2-dimethylaminoethylamine (5 ml) is heated in dimethylsulfoxide (80 ml) for 6 hours at 100° C. (with stirring). The reaction mixture is quenched with water and the solid which separates, is filtered off and washed well with water. Examination of the TLC (CHCl$_3$:MeOH; 3:1) showed the products to be sufficiently pure to be used for further reactions without purification. Yield 3.2 g, 85%, mass spectrum (CI) 376 (M+1).

REFERENCE EXAMPLE 161

6-[(2-Methylbenzeneacetyl)amino]pyridine-3-carboxylic acid

To a cooled (0° C.) mixture of 5.0 g methyl 6-aminopyridine-3-carboxylate, 12.6 ml of N,N-diisopropylethylamine in 40 ml of dichloromethane is added a solution of 12.2 g of 2-methylbenzeneacetyl chloride in 10 ml of dichloromethane. The mixture is stirred under argon at room temperature overnight. The mixture is diluted with 200 ml of dichloromethane and 50 ml of water and the organic layer separated. The organic layer is washed with 50 ml each of 1M NaHCO$_3$, brine and dried (Na$_2$SO$_4$). The solution is filtered through a thin pad of hydrous magnesium silicate and the filtrate concentrated to dryness. The residue (9.0 g) is chromatographed on a silica gel column with hexane-ethyl acetate (3:1) as eluent to give 8.6 g of solid. This solid, mainly methyl 6-[[bis(2-methylbenzeneacetyl)]amino]pyridine-3-carboxylate, is dissolved in 60 ml of tetrahydrofuran-methanol (1:1) and 23 ml of 5N NaOH added to the solution. The mixture is stirred at room temperature overnight and the mixture concentrated under vacuum. Water (25 ml) is added and the mixture is stirred and acidified with cold 1N HCl. The mixture is chilled and the solid filtered and washed with water to give 5.9 g of off-white solid.

REFERENCE EXAMPLE 162

6-[(2-Methylbenzeneacetyl)amino]pyridine-3-carbonyl chloride

A mixture of 4.5 g of 6-[(2-methylbenzeneacetyl)amino]pyridine-3-carboxylic acid and 25 ml of thionyl chloride is refluxed for 1 hour and then concentrated to dryness under vacuum. To the residue is added 20 ml of toluene and the solvent removed under vacuum. The addition and removal of toluene is repeated and the residual solid dried at room temperature under vacuum to give 5.3 g of dark brown solid.

REFERENCE EXAMPLE 163

6-[(2-Methylbenzeneacetyl)amino]pyridine-3-carboxylic acid

To a chilled solution (0° C.) of 5.0 g of methyl 6-aminopyridine-3-carboxylate and 12.6 ml of diisopropylethylamine in 40 ml of dichloromethane under argon is added 12.2 g of 2-methylbenzeneacetyl chloride in 10 ml of dichloromethane. The mixture is stirred at room temperature 16 hours and diluted with 200 ml of dichloromethane and 50 ml of water. The organic layer is separated and washed with 50 ml each of 1M NaHCO$_3$, brine and dried (Na$_2$SO$_4$). The solution is filtered through a thin pad of hydrous magnesium silicate and the filtrate concentrated to dryness. The residue (9.0 g) is purified by chromatography on silica gel with hexaneethyl acetate (3:1) as eluent to give 0.70 g of methyl 6-[[bis(2-methylbenzeneacetyl)]amino]pyridine-3-carboxylate and 8.6 g of a mixture of methyl 6-[(2-methylbenzeneacetyl)amino]pyridine-3-carboxylate and the bis acylated product. The above mixture (8.6 g) of mono and bis acylated product is dissolved in 60 ml of tetrahydrofuran-methanol (1:1) and 23 ml of 5N NaOH is added. The solution is stirred at room temperature for 16 hours, concentrated under vacuum, diluted with 25 ml of H$_2$O and acidified with cold 1N HCl. The precipitated solid is filtered off and dried to give 5.9 g of white solid.

REFERENCE EXAMPLE 164

6-[(2-Methylbenzeneacetyl)amino]pyridine-3-carbonyl chloride

A mixture of 4.5 g of 6-[(2-methylbenzeneacetyl)amino]pyridine-3-carboxylic acid and 17 ml of thionyl chloride is heated on a steam bath for ½ hour. An additional 815 ml of thionyl chloride is added and the mixture refluxed for 0.5 hour. The volatiles are removed under vacuum and toluene (20 ml) added (twice) and the solvent removed under vacuum to give 5.3 g of a dark colored solid.

REFERENCE EXAMPLE 165

2-Biphenylcarbonyl chloride

A mixture of 5.6 g of 2-biphenylcarboxylic acid and 29 ml of thionyl chloride is heated on a steam bath for 0.5 hour and the volatiles removed under vacuum. Toluene (40 ml) is added (twice) and the solvent removed under vacuum to give 6.8 g of a yellow oil.

REFERENCE EXAMPLE 166

Methyl 6-[[bis(2-biphenylcarbonyl)]amino]pyridine-3-carboxylate

To a chilled (0° C.) solution of 2.64 g of methyl 6-aminopyridine-3-carboxylate and 5.5 ml of diisopropylethylamine in 30 ml of dichloromethane under argon is added 6.8 g of 2-biphenylcarbonyl chloride in 10 ml of dichloromethane. The mixture is stirred at room temperature 2 days and then diluted with 120 ml of dichloromethane and 50 ml of water. The organic layer is separated, washed with 50 ml each of 1M NaHCO$_3$ and brine and dried (Na$_2$SO$_4$). The solution is filtered through a thin pad of hydrous magnesium silicate and the filtrate concentrated under vacuum to give a solid. Crystallization from ethyl acetate gives 6.2 g of white crystals, m.p. 180°–188° C.

REFERENCE EXAMPLE 167

6-[(2-Biphenylcarbonyl)amino]pyridine-3-carboxylic acid

To a chilled (0° C.) mixture of 6.0 g of methyl 6-[[bis(2-biphenylcarbonyl)]amino]pyridine-3-carboxylate in 40 ml of methanol and 30 ml of tetrahydrofuran is added slowly 18 ml of 2N NaOH. The mixture is stirred at room temperature overnight and brought to pH 5 with glacial acetic acid. The mixture is concentrated, acidified to pH 2–3 with 1N HCl and extracted with 250 ml of ethyl acetate. The extract is washed with 50 ml of brine, dried (Na$_2$SO$_4$) and the solvent removed under vacuum. The residual white solid is triturated with 15 ml of ethyl acetate to give 3.35 g of white crystals, m.p. 215°–217° C.

REFERENCE EXAMPLE 168

6-[(2-Biphenylcarbonyl)amino]pyridine-3-carbonyl chloride

A mixture of 1.9 g of 6-[(2-biphenylcarbonyl)amino] pyridine-3-carboxylic acid and 9 ml of thionyl chloride is refluxed for 1 hour and then concentrated to dryness under vacuum. Toluene (15 ml) is added (twice) to the residue and the solvent removed under vacuum to give 2.1 g of a light brown oil.

REFERENCE EXAMPLE 169

6-[(Cyclohexylcarbonyl)amino]pyridine-3-carboxylic acid

To a chilled (0° C.) solution of 5.0 g of methyl 6-aminopyridine-3-carboxylate and 12.6 ml of diisopropylethylamine in 50 ml of dichloromethane under argon is added a solution of 9.7 ml of cyclohexylcarbonyl chloride in 10 ml of dichloromethane. The mixture is stirred at room temperature overnight and diluted with 200 ml of dichloromethane and 60 ml of water. The organic layer is separated, washed with 60 ml of brine and dried (Na$_2$SO$_4$). The solution is filtered through a thin pad of hydrous magnesium silicate and the filtrate concentrated under vacuum to give 12.8 g of a solid.

The above solid (12.0 g) in a mixture of 150 ml of tetrahydrofuran-methanol (1:1) is chilled (0° C.) and 62 ml of 2N sodium hydroxide added. The mixture is stirred at room temperature for 3 hours, neutralized with 10 ml of glacial acetic acid and concentrated under vacuum. The mixture (containing solid) is acidified to pH 1 with 1N HCl and extracted with 250 ml of ethyl acetate and twice with 100 ml of ethyl acetate. The combined extract is washed with 100 ml of brine, dried (Na$_2$SO$_4$) and concentrated to a white solid. Trituration with hexane gives 6.5 g of product as a white solid.

REFERENCE EXAMPLE 170

5-[(6-Chloro-3-pyridinyl)carbonyl]-5,10-dihydro-4H-pyrazolo[5,1-c][1,4]benzodiazepine To a solution of 10 mmol of 5,10-dihydro-4H-pyrazolo[5,1-c][1,4]-benzodiazepine and 1.5 g of triethylamine in 20 ml of dichloromethane is added a solution of 2.11 g of 6-chloropyridine-3-carbonyl chloride in 5 ml of dichloromethane. The mixture is stirred for 3 hours at room temperature diluted with 20 ml of dichloromethane and washed with 30 ml of 1N NaOH. The organic layer is washed twice with 20 ml of 1N NaOH, dried (Na$_2$SO$_4$) and the solvent removed. The residue is triturated with ether to give 3 g of solid.

REFERENCE EXAMPLE 171

Methyl 4-[([1,1'-Biphenyl]-2-carbonyl)amino]-3-methoxybenzoate

A mixture of 10.0 g of [1,1'-biphenyl]-2-carboxylic acid in 75 ml of methylene chloride and 12.52 g of oxalyl chloride is stirred at room temperature for 15 hours. The volatiles are evaporated in vacuo to give 11.06 g of an oil. A 2.16 g portion of the above oil in 25 ml of methylene chloride is reacted with 1.81 g of methyl 4-amino-3-methoxybenzoate and 1.30 g of N,N-diisopropylethylamine by stirring at room temperature for 18 hours. The reaction mixture is washed with water, saturated aqueous NaHCO$_3$ and the organic layer dried(Na$_2$SO$_4$). The organic layer is passed through hydrous magnesium silicate and hexane added to the filtrate at the boil to give 3.20 g of the desired product as a crystalline solid, m.p. 115°–117° C.

REFERENCE EXAMPLE 172

Methyl 4-[([1,1'-Biphenyl]-2-carbonyl)amino-2-chlorobenzoate

A solution of 2.37 g of [1,1'-biphenyl]-2-carbonyl chloride in 10 ml of methylene chloride is added dropwise to an ice cold solution of 1.84 g of methyl 4-amino-2-chlorobenzoate and 1.49 g of N,N-diisopropylethylamine in 50 ml of methylene chloride. The reaction mixture is stirred at room temperature for 18 hours and washed with water, saturated aqueous NaHCO$_3$ and the organic layer dried(Na$_2$SO$_4$). The organic layer is passed through a pad of hydrous magnesium silicate and hexane added at the boil to give 1.1 g of the desired product as a crystalline solid, m.p. 132°–134° C. M$^+$H=365

REFERENCE EXAMPLE 173

4-[([1,1'-Biophenyl]-2-carbonyl)amino]-2-chlorobenzoic Acid

A mixture of 3.0 g of methyl 4-[([1,1'-biphenyl]-2-carbonyl)amino]-2-chlorobenzoate in 75 ml of absolute ethanol and 2.0 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 0.1 g of the desired product as a crystalline solid, m.p. 217°–219° C.

REFERENCE EXAMPLE 174

4-[([1,1'-Biphenyl]-2-carbonyl)-amino]-3-methoxybenzoyl Chloride

A solution of 2.69 g of 4-[([1,1'-biphenyl]-2-carbonyl] amino]-3-methoxy benzoic acid in 5 ml of thionyl chloride is heated on a steam bath for 1 hour under Argon. The volatiles are removed in vacuo to give a residue which is stirred with hexane to give 2.58 g of crystalline solid, m.p. 121°–123° C. M+361.

REFERENCE EXAMPLE 175

Methyl 4-[([1,1'-Biphenyl]-2-carbonyl)amino]benzoate

A mixture of 10.0 g of [1,1'-biphenyl]-2-carboxylic acid in 75 ml of methylene chloride and 12.52 g of oxalyl chloride is stirred at room temperature for 18 hours. The volatiles are evaporated in vacuo to give 11.66 g of an oil. A 7.5 g portion of the above oil in 25 ml of methylene chloride is added dropwise to a solution of 4.53 g of methyl 4-aminobenzoate and 4.3 g of N,N-diisopropylethylamine in 100 ml of methylene chloride at 0° C. The reaction mixture is stirred at room temperature for 18 hours and washed with water, and saturated aqueous NaHCO$_3$ and the organic layer dried($Na_2SO_4$). The organic layer is passed through hydrous magnesium silicate and hexane added to the filtrate at the boil to give 8.38 g of the desired product as a crystalline solid, m.p. 163°–165° C.

REFERENCE EXAMPLE 176

4-[((1,1'-Biphenyl-2-carbonyl)amino]benzoic Acid

A 3.15 g sample of methyl 4-[((1,1'-biphenyl]-2-carbonyl)amino]benzoate is refluxed for 8 hours in 100 ml of ethyl alcohol and 2.5 ml of 10N sodium hydroxide. The cooled reaction mixture is acidified with [[? acid]] and the desired product collected and dried to give 2.9 g of the desired product as a solid m.p. 246°–249° C. M+H=318.

REFERENCE EXAMPLE 177

4-[((1,1'-Biphenyl]-2-carbonyl)amino]benzoyl Chloride

A mixture of 1.39 g of 4-[((1,1'-biphenyl]-2-carbonyl)amino]benzoic acid in 2.0 ml of thionyl chloride is heated on a steam bath for 1 hour. Cold hexane is added and the crystalline solid collected and dried to give 1.34 g of the desired product, m.p. 118°–120° C.

REFERENCE EXAMPLE 178

2-(Phenylmethyl)benzoyl Chloride

A mixture of 5.0 g of 2-(phenylmethyl)benzoic acid in 5.0 ml of thionyl chloride is heated on a steam bath for 1 hour. The volatiles are evaporated in vacuo to give 5.74 g of the desired product as an oil. $M^+$=227 as methyl ester.

REFERENCE EXAMPLE 179

Methyl 4-[[2-(Phenylmethyl)benzoyl]amino]benzoate

To 3.03 g of methyl 4-aminobenzoate and 3.12 g of N,N-diisopropylethylamine in 75 ml of methylene chloride is added 5.54 g of 2-(phenylmethyl)benzoyl chloride and the reactants stirred at room temperature for 18 hours. The reaction mixture is washed with water, saturated aqueous $NaHCO_3$ and the organic layer dried($Na_2SO_4$). The organic layer is passed through hydrous magnesium silicate two times and hexane added to the filtrate at the boil to give 5.04 g of the desired product as a crystalline solid, m.p. 138°–139° C.

REFERENCE EXAMPLE 180

Sodium 4-[[2-(Phenylmethyl)benzoyl]amino]benzoate

A mixture of 4.90 g of methyl 4-[[2-(phenylmethyl)benzoyl]amino]benzoate in 100 ml of absolute ethanol and 3.50 ml of 10N sodium hydroxide is heated on a steam bath for 3 hours. The aqueous phase is filtered and the resulting solid collected and dried to give 4.25 g of the desired product m.p. 340°–346° C.

REFERENCE EXAMPLE 181

4-[[2-(Phenylmethyl)benzoyl]amino]benzoic Acid

A mixture of 4.0 g sodium 4-[[2-(phenylmethyl)benzoyl] amino]benzoate is suspended in water and the pH adjusted to 5 with acetic acid. The solid is collected by filtration and dried at 80° C. in vacuo to give 3.75 g of the desired product, 246°–247° C. $M^+$=332.

REFERENCE EXAMPLE 182

4-[[2-(Phenylmethyl)benzoyl]amino]benzoyl Chloride

A mixture of 2.0 g of 4-[[2-(phenylmethyl)benzoyl] amino]benzoic acid in 2.0 ml of thionyl chloride is heated on a steam bath for 1 hour. The volatiles are evaporated in vacuo to give 1.53 g of the desired product as an oil. $M^+$=346 as methyl ester.

REFERENCE EXAMPLE 183

Methyl 4-[[(2-phenylmethyl)benzoyl]amino]-2-chlorobenzoate

A mixture of 5.0 g of 2-(phenylmethyl)benzoic acid in 5.0 ml of thionyl chloride is heated on a steam bath for 1 hour. The volatiles are evaporated in vacuo to give 5.70 g of an oil. A 2.85 g portion of the above oil in 25 ml of methylene chloride is added to a solution of 50 ml of methylene chloride containing 1.85 g of methyl 4-amino-2-chlorobenzoate and 1.65 g of N,N-diisopropylethylamine by stirring at room temperature for 18 hours. The reaction mixture is washed with water, saturated aqueous $NaHCO_3$ and the organic layer dried($Na_2SO_4$). The organic layer is passed through hydrous magnesium silicate two times and hexane added to the filtrate at the boil to give 2.96 g of the desired product as a crystalline solid, m.p. 133°–135° C. $M^+$=380.

REFERENCE EXAMPLE 184

Methyl 4-[[(2-Phenylmethyl)benzoyl]amino]-3-methoxybenzoate

A solution of 2.85 g of 2-(phenylmethyl)benzoyl chloride in 25 ml of methylene chloride is added dropwise to an ice cold solution of 1.84 g of methyl 4-amino-3-methoxybenzoate and 1.61 g of N,N-diisopropylethylamine in 50 ml of methylene chloride. The reaction mixture is stirred at room temperature for 18 hours and washed with water, saturated aqueous $NaHCO_3$ and the organic layer dried($Na_2SO_4$). The organic layer is passed through a pad of hydrous magnesium silicate and hexane added at the boil to give 2.2 g of the desired product as a crystalline solid, m.p. 129°–131° C. $M^+$=376.

REFERENCE EXAMPLE 185

2-Chloro-4-[[(2-Phenylmethyl)benzoyl]amino]benzoic Acid

A mixture of 2.8 g of methyl 2-chloro-4-[[(2-phenylmethyl)benzoyl]aminobenzoate in 75 ml of absolute ethanol and 1.84 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 2.6 g of the desired product as a crystalline solid, m.p. 184°–187° C. $M^+H$=366.

REFERENCE EXAMPLE 186

3-Methoxy-4-[[(2-phenylmethyl)benzoyl]amino]benzoate

A mixture of 2.05 g of methyl 4-[[(2-phenylmethyl)benzoyl]amino]-3-methoxybenzoate in 75 ml of absolute ethanol and 1.4 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 1.87 g of the desired product as a crystalline solid, m.p. 176°–178° C. $M^+H=362$.

REFERENCE EXAMPLE 187

3-Methoxy-4-[[(2-phenylmethyl)benzoyl]amino]benzoyl Chloride

A mixture of 1.71 g of 3-methoxy-4-[[(2-phenylmethyl)benzoyl]amino]benzoic acid in 2.0 ml of thionyl chloride is heated on a steam bath under Argon for 1 hour and hexane added. The resulting solid is collected and dried to give 1.71 g of the desired product as a crystalline solid, m.p. 130°–135° C. $M^+=376$ as the methyl ester.

REFERENCE EXAMPLE 188

[4'-(Trifluoromethyl)-[1,1'-biphenyl]-2-carbonyl Chloride

A mixture of 5.0 g of 4'-(trifluoromethyl)[1,1'-biphenyl]-2-carboxylic acid in 5.0 ml of thionyl chloride is heated on a steam bath under Argon for 1 hour and hexane added. The resulting solid is collected and dried to give 5.36 g of the desired product as a colorless oil. $M^+=280$ as methyl ester.

REFERENCE EXAMPLE 189

Methyl 2-Chloro-4-[([4'-(trifluoromethyl)[1,1'-biphenyl]carbonyl)amino]benzoate

A solution of 3.13 g of [4'-(trifluoromethyl)[1,1'-biphenyl]-2-carbonyl chloride in 25 ml of methylene chloride is added dropwise to an ice cold solution of 1.84 g of methyl 4-aminobenzoate and 1.43 g of N,N-diisopropylethylamine in 50 ml of methylene chloride. The reaction mixture is stirred at room temperature for 18 hours and washed with water, saturated aqueous $NaHCO_3$ and the organic layer dried($Na_2SO_4$). The organic layer is passed through a pad of hydrous magnesium silicate and hexane added at the boil to give 3.36 g of the desired product as a crystalline solid, m.p. 164°–165° C. $M^+=396$.

REFERENCE EXAMPLE 190

3-Methoxy-4-[([4'-(trifluoromethyl)[1,1'-biphenyl]-2-carbonyl)amino]benzoyl Chloride A mixture of 2.0 g of 3-methoxy-4-[([4'-(trifluoromethyl)[1,1'-biphenyl]-2-carbonyl)amino]benzoic acid in 20 ml of thionyl chloride is heated on a steam bath under Argon for 1 hour and hexane added. The resulting solid is collected and dried to give 1.92 g of the desired product as a crystalline solid, m.p. 136°–138° C.

REFERENCE EXAMPLE 191

3-Methoxy-4-[([4'-trifluoromethyl)[1,1'-biphenyl]-2-carbonyl)amino]benzoic Acid

A mixture of 3.78 g of methyl 3-methoxy-4-[([4'-trifluoromethyl)[1,1+-biphenyl]-2-carbonyl)amino]benzoate in 75 ml of absolute ethanol and 2.20 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 3.49 g of the desired product as a crystalline solid, m.p. 213°–215° C.

REFERENCE EXAMPLE 192

Methyl 3-Methoxy-4-[([4'-trifluoromethyl)[1,1'-biphenyl]-2-carbonyl)amino]benzoate A solution of 3.56 g of [4'-(trifluoromethyl)[1,1'-biphenyl]-2-carbonyl chloride in 25 ml of methylene chloride is added dropwise to an ice cold solution of 1.81 g of methyl 4-amino-3-methoxybenzoate and 1.62 g of N,N-diisopropylethylamine in 50 ml of methylene chloride. The reaction mixture is stirred at room temperature for 18 hours and washed with water, saturated aqueous $NaHCO_3$ and the organic layer dried($Na_2SO_4$). The organic layer is passed through a pad of hydrous magnesium silicate and hexane added at the boil to give 3.9 g of the desired product as a crystalline solid, m.p. 112°–113° C.

REFERENCE EXAMPLE 193

2-Chloro-4-[([4'-(trifluoromethyl)[1,1'-biphenyl]-2-carbonyl)amino]benzoyl Chloride A mixture of 1.39 g of 2-chloro-4-[([4'-(trifluoromethyl)[1,1'-biphenyl]-2-carbonyl)amino]benzoic acid in 2.0 ml of thionyl chloride is heated on a steam bath for 1 hour. The reaction mixture is concentrated to a residue in vacuo to a residue. Cold hexane is added to the residue and the solid collected and dried to give 1.39 g of the desired product.

REFERENCE EXAMPLE 194

2-Chloro-4-[([4'-(trifluoromethyl)[1,1'-biphenyl]-2-carbonyl)amino]benzoic acid

A mixture of 3.83 g of methyl 2-chloro-4-[([4'-(trifluoromethyl)[1,1'-biphenyl]-2-carbonyl)amino]benzoate in 75 ml of absolute ethanol and 2.20 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 3.42 g of the desired product as a crystalline solid, m.p. 187°–189° C.

REFERENCE EXAMPLE 195

Methyl 2-Chloro-4-[([4'-(trifluoromethyl)[1,1'-biphenyl]-2-carbonyl)amino]benzoate A solution of 3.56 g of [4'-(trifluoromethyl)[1,1'-biphenyl]-2-carbonyl chloride in 10 ml of methylene chloride is added dropwise to an ice cold solution of 1.86 g of methyl 2-chloro-4-aminobenzoate and 1.6 g of N,N-diisopropylethylamine in 50 ml of methylene chloride. The reaction mixture is stirred at room temperature for 18 hours and washed with water, saturated aqueous NaHCO₃ and the organic layer dried(Na₂SO₄). The organic layer is passed through a pad of hydrous magnesium silicate(3×) and hexane added to the filtrate at the boil to give 4.0 g of the desired product as a crystalline solid, m.p. 130°–132° C.

REFERENCE EXAMPLE 196

4-[([4'-(Trifluoromethyl)[1,1'-biphenyl]carbonyl)amino]benzoic Acid

A mixture of 3.0 g of methyl 4-[([4'-(trifluoromethyl)[1,1'-biphenyl]-2-carbonyl)amino]benzoate in 75 ml of absolute ethanol and 2.0 ml of 10N sodium hydroxide is heated on a steam bath for 3 hours. Water is added to obtain a solution which is extracted with methylene chloride. The aqueous phase is acidified with acetic acid and the resulting solid collected and dried in vacuo at 80° C. to give 2.93 g of the desired product as a crystalline solid, m.p. 243°–245° C. $M^+$=385.

REFERENCE EXAMPLE 197

Methyl 6-[[3-(2-methylpyridinyl)carbonyl]amino]pyridine-3-carboxylate

To a stirred solution of 3 g of methyl 6-aminopyridine-3-carboxylate and 4 ml of N,N-diisopropylethylamine in 100 ml of methylene chloride is added dropwise a solution of 6.4 g of 2-methylpyridine-3-carbonyl chloride in 25 ml of methylene chloride. The reaction mixture is stirred at room temperature for 2 hours and quenched with water. The organic layer is washed with water, dried(MgSO₄), filtered and evaporated in vacuo to a residue which is stirred with ether and the resulting solid collected and air dried to give 6.8 g of the desired product. $M^+$=390.

REFERENCE EXAMPLE 198

6-[[3-(2-methylpyridinyl)carbonyl]amino]pyridine-3-carboxylic Acid

To a solution of 6.5 g of methyl 6-[[3-(2-methylpyridinyl)carbonyl]amino]pyridine-3-carboxylate in 100 ml of 1:1 tetrahydrofuran:methyl alcohol is added 20 ml of 5N NaOH. The reaction mixture is stirred overnight and evaporated in vacuo to a residue. The residue is dissolved in water and neutralized with acetic acid. The separated solid is filtered and air-dried to give 3.0 g of the desired product. $M^+$=257.

REFERENCE EXAMPLE 199

Methyl 6-[([1,1'-biphenyl]-2-carbonyl)amino]-pyridine-3-carboxylate

To a solution of 1.5 g of methyl 6-aminopyridine-3-carboxylate in 100 ml of methylene chloride is added 3 ml of N,N-diisopropylethylamine at room temperature. To the stirred reaction mixture is slowly added a solution of 2.5 g of [1,1'-biphenyl]-2-carbonyl chloride. The reaction mixture is stirred at room temperature for 4 hours and then quenched with water. The organic layer is washed well with water and dried over anhydrous MgSO₄, filtered and evaporated in vacuo to a solid residue. The residue is stirred with ether, filtered and dried to give 3.0 g of the desired product:$M^+$=332.

REFERENCE EXAMPLE 200

6-[([1,1'-Biphenyl]-2-carbonyl)amino]pyridine-3-carboxylic Acid

To a stirred solution of 2.5 g of methyl 6-[([1,1'-Biphenyl]-2-carbonyl)amino]-pyridine-3-carboxylate in 50 ml of 1:1 tetrahydrofuran:methanol is added 10 ml of 5N sodium hydroxide and the mixture stirred at room temperature for 16 hours. The reaction mixture is concentrated in vacuo to a residue which is dissolved in water and neutralized with acetic acid. The separated colorless solid is filtered and air dried to give 2.0 g of the desired product:$M^+$=318.

REFERENCE EXAMPLE 201

Methyl 2-(2-Pyridinyl)benzoate

A mixture of 12 g of methyl 2-(iodomethyl)benzoate, 20 g of n-butyl stannane and 2 g of tetrakis(triphenylphosphine)palladium (O) are refluxed in degassed toluene for 48 hours. The reaction mixture is concentrated in vacuo to a residue which is purified by column chromatography on silica gel by elution with 1:1 ethyl acetate:hexane to give 5.5 g of the desired product as an oil. $M^+$=213.

REFERENCE EXAMPLE 202

2-(2-Pyridinyl)benzoic Acid

A mixture of 3.0 g of methyl 2-(2-pyridinyl)benzoate and 600 mg of sodium hydroxide in 50 ml of 9:1 methanol:water is refluxed for 4 hours. The reaction mixture is concentrated in vacuo and the residue dissolved in 50 ml of cold water. The solution is neutralized with glacial acetic acid and the resulting product filtered, washed with water, and dried to give 2.5 g of the desired product:M+=200.

Example 1

N-[5-(5H-Pyrrolo[2,1-c][1,4]benzodiazepin-10(11H)-ylcarbonyl)-2-pyridinyl]-5-fluoro-2-methylbenzamide A mixture of thionyl chloride (100 ml) and 6-[(5-fluoro-2-methylbenzoyl)amino]pyridine-3-carboxylic acid (2.7 g, 10 mmol) is heated to reflux for 5 hours. At the end, excess thionyl chloride is removed and the acid chloride is dissolved in CH₂Cl₂ (100 ml). At room temperature, the methylene chloride solution of the 6-[(5-fluoro-2-methylbenzoyl)amino]pyridine-3-carbonyl chloride is added slowly. The reaction mixture is stirred at room temperature for 2 hours and quenched with ice cold water. The reaction mixture is washed with 0.1N NaOH and subsequently washed with water. The CH₂Cl₂ layer is separated; dried (MgSO₄), filtered and concentrated. The product is purified by silica gel column chromatography by eluting first with 10% ethyl acetate-hexane (1 L) and then with 30% ethyl acetate-hexane. The product is crystallized from ethyl acetate-hexane. Yield 1.0 g, 46; mass spectrum (FAB), $M^+1$ 441; $M^+$Na: 462.

As described for Example 1, the following compounds are prepared (Table C).

TABLE C

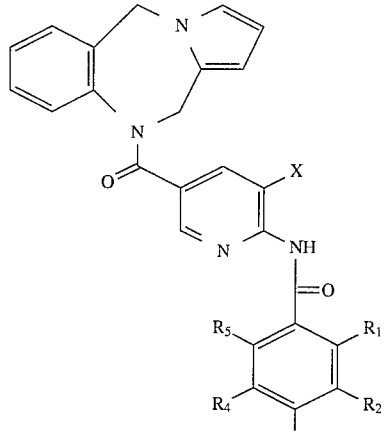

| Ex. No | R₁ | R₂ | R₃ | R₄ | R₅ | X | M+1 |
|---|---|---|---|---|---|---|---|
| 2 | CH₃ | H | H | H | H | H | 423 |
| 3 | CH₃ | H | H | H | F | H | |
| 4 | CH₃ | F | H | H | H | H | 441 |
| 5 | H | OCH₃ | OCH₃ | OCH₃ | H | H | 499 |
| 6 | Cl | H | H | H | H | H | 443 |
| 7 | F | H | F | H | H | H | 445 |
| 8 | Br | H | H | H | H | H | 489 |
| 9 | Cl | H | F | H | H | H | 461 |
| 10 | Ph | H | H | H | H | H | |
| 11 | Cl | H | H | Br | H | H | |
| 12 | CH₃ | H | H | H | H | Br | 502 |
| 13 | CH₃ | H | H | F | H | Cl | |
| 14 | Cl | H | H | Cl | H | H | |
| 15 | CH₃ | CH₃ | H | H | H | H | |
| 16 | Cl | H | F | H | H | H | |
| 17 | Cl | H | H | CF₃ | H | H | |
| 18 | Cl | H | H | H | F | H | |
| 19 | Cl | H | H | H | Cl | H | |
| 20 | Cl | H | H | F | H | H | |
| 21 | 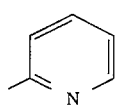 | H | H | H | H | H | |
| 22 | 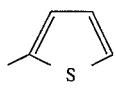 | H | H | H | H | H | |
| 23 | CH₃ | H | H | H | CH₃ | H | |
| 24 | Cl | H | H | F | H | Cl | |
| 25 | Cl | H | F | H | H | Cl | |
| 26 | Cl | Cl | H | H | H | H | |
| 27 | Cl | H | H | Cl | H | H | |
| 28 | —OCH₃ | H | H | H | H | H | |
| 29 | OCF₃ | H | H | H | H | H | |
| 30 | —CF₃ | H | H | H | H | H | |

TABLE C-continued

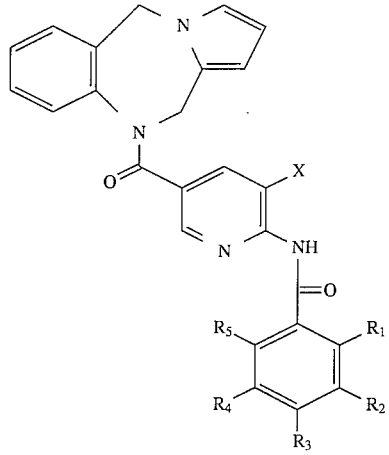

| Ex. No | R₁ | R₂ | R₃ | R₄ | R₅ | X | M+1 |
|---|---|---|---|---|---|---|---|
| 31 | Cl | Cl | H | Cl | H | H | |
| 32 | —SCH₃ | H | H | H | H | H | |
| 33 | Cl | H | NO₂ | H | H | H | |
| 34 | CH₃ | H | H | CH₃ | H | H | |
| 35 | F | H | H | Cl | H | H | |
| 36 | Cl | H | H | NH₂ | H | H | |
| 37 | F | CF₃ | H | H | H | H | |
| 38 | —OCH₃ | H | H | Cl | H | H | |
| 39 | Cl | H | H | —SCH₃ | H | H | |
| 40 | F | H | H | H | CF₃ | H | |
| 41 | F | H | CF₃ | H | H | H | |
| 42 | CF₃ | H | F | H | H | H | |
| 43 | NO₂ | H | H | H | H | H | |
| 44 | F | H | H | H | H | H | |
| 45 | Cl | H | NH₂ | H | H | H | |

EXAMPLE 46

N-[5-(5H-Pyrrolo[2,1-c][1,4]benzodiazepin-10(11H)ylcarbonyl)-2-pyridinyl]-2-methylbenzene-acetamide A mixture of 2.0 mmol of 10,11-dihydro-10-(6-amino-3-pyridinylcarbonyl)-5H-pyrrolo[2,1-c][1,4]benzodiazepine, 2.1 mmol of 2-methylbenzeneacetyl chloride and 5 mmol of triethylamine in 10 ml of dichloromethane is stirred under argon at room temperature for 16 hours. The solvent is removed under vacuum and the residue partitioned between 50 ml of ethyl acetate and 25 ml of water. The organic layer is separated, washed with H₂O, 1N NaHCO₃, brine and dried (Na₂SO₄). The solvent is removed and the residue chromatographed on silica gel with ethyl acetate-hexane as solvent to give the product as a solid.

As described for Example 46, the following compounds are prepared (Table D).

TABLE D

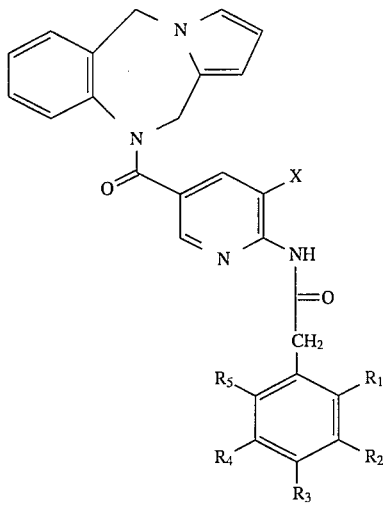

| Ex No. | R₁ | R₂ | R₃ | R₄ | R₅ | X |
|---|---|---|---|---|---|---|
| 47 | CH₃ | H | H | CH₃ | H | H |
| 48 | CH₃ | H | H | H | H | Br |
| 49 | CH₃ | H | H | H | H | Cl |
| 50 | Cl | H | H | H | H | H |
| 51 | Cl | H | H | H | H | Br |
| 52 | Cl | H | H | H | H | Cl |
| 53 | Cl | H | Cl | H | H | H |
| 54 | Cl | H | Cl | H | H | Br |
| 55 | Cl | H | Cl | H | H | Cl |
| 56 | —OCH₃ | H | H | H | H | H |
| 57 | —OCH₃ | H | H | H | H | Br |
| 58 | —OCH₃ | H | H | H | H | Cl |
| 59 | —OCH₃ | H | H | —OCH₃ | H | H |
| 60 | —OCH₃ | H | H | —OCH₃ | H | Br |
| 61 | —OCH₃ | H | H | —OCH₃ | H | Cl |
| 62 | H | —OCH₃ | —OCH₃ | H | H | H |
| 63 | H | —OCH₃ | —OCH₃ | H | H | Br |
| 64 | H | —OCH₃ | —OCH₃ | H | H | Cl |
| 65 | H | Cl | H | H | H | H |
| 66 | H | Cl | H | H | H | Br |
| 67 | H | Cl | H | H | H | Cl |
| 68 | H | H | Cl | H | H | H |
| 69 | H | H | Cl | H | H | Br |
| 70 | H | H | Cl | H | H | Cl |
| 71 | F | H | H | H | H | H |
| 72 | F | H | H | H | H | Br |
| 73 | F | H | H | H | H | Cl |
| 74 | H | F | H | H | H | H |
| 75 | H | F | H | H | H | Br |
| 76 | H | F | H | H | H | Cl |
| 77 | H | H | F | H | H | H |
| 78 | H | H | F | H | H | Br |
| 79 | H | H | F | H | H | Cl |
| 80 | H | CH₃ | H | H | H | H |
| 81 | H | CH₃ | H | H | H | Br |
| 82 | H | CH₃ | H | H | H | Cl |

EXAMPLE 83

10,11-Dihydro-10-[[6-[[[2-methylphenyl)amino]carbonyl]amino]-3-pyridinyl]carbonyl]-5H-pyrrolo[2,1-c][1,4]benzodiazepine A mixture of 2.0 mmol of 10,11-dihydro-10-(6-amino-3-pyridinylcarbonyl)-5H-pyrrolo[2,1-c][1,4]benzodiazepine and 4.0 mmol of (2-methylphenyl)isocyanate in 12 ml of tetrahydrofuran is refluxed for 16 hours. The solvent is removed and the residue chromatographed on silica gel with ethyl acetate-hexane as solvent to give the product as a solid.

As described for Example 83, the following compounds are prepared (Table E).

TABLE E

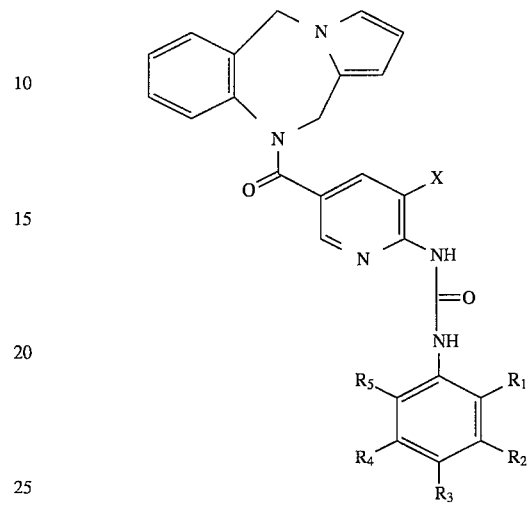

| Ex No. | R₁ | R₂ | R₃ | R₄ | R₅ | X |
|---|---|---|---|---|---|---|
| 84 | H | CH₃ | H | H | H | H |
| 85 | H | CH₃ | H | H | H | Br |
| 86 | H | CH₃ | H | H | H | Cl |
| 87 | H | H | CH₃ | H | H | H |
| 88 | H | H | CH₃ | H | H | Br |
| 89 | H | H | CH₃ | H | H | Cl |
| 90 | Cl | H | H | H | H | H |
| 91 | Cl | H | H | H | H | Br |
| 92 | Cl | H | H | H | H | Cl |
| 93 | H | Cl | H | H | H | H |
| 94 | H | Cl | H | H | H | Br |
| 95 | H | Cl | H | H | H | Cl |
| 96 | H | H | Cl | H | H | H |
| 97 | H | H | Cl | H | H | Br |
| 98 | H | H | Cl | H | H | Cl |
| 99 | Cl | Cl | H | H | H | H |
| 100 | Cl | Cl | H | H | H | Br |
| 101 | Cl | Cl | H | H | H | Cl |
| 102 | Cl | H | Cl | H | H | H |
| 103 | Cl | H | Cl | H | H | Br |
| 104 | Cl | H | Cl | H | H | Cl |
| 105 | Cl | H | H | H | Cl | H |
| 106 | Cl | H | H | H | Cl | Br |
| 107 | Cl | H | H | H | Cl | Cl |
| 108 | H | Cl | Cl | H | H | H |
| 109 | H | Cl | Cl | H | H | Br |
| 110 | H | Cl | Cl | H | H | Cl |
| 111 | F | H | F | H | H | H |
| 112 | F | H | F | H | H | Br |
| 113 | F | H | F | H | H | Cl |
| 114 | F | H | H | F | H | H |
| 115 | F | H | H | F | H | Br |
| 116 | F | H | H | F | H | Cl |
| 117 | F | H | H | H | F | H |
| 118 | F | H | H | H | F | Br |
| 119 | F | H | H | H | F | Cl |

EXAMPLE 120

N-[5-[[3-[(Dimethylamino)methyl]-[5H-pyrrolo[2,1-c][1,4]benzodiazepin-10(11H)]-yl]carbonyl]-2-pyridinyl]-5-fluoro-2-methylbenzamide A mixture of 0.44 g of N-[5-(5H-pyrrolo-2,1-c][1,4]benzodiazepin-10(11H)-ylcarbonyl)-2pyridinyl]-5-fluoro-2-methylbenzamide, 5 ml of a 40% aqueous solution of dimethylamine and 5 ml of an aqueous solution of formaldehyde in 50 ml of tetrahydrofuranmethanol (1:1) is refluxed for 16 hours in the presence of a drop of glacial acetic acid. The mixture is concentrated under vacuum and the residue extracted with chloroform. The extract is washed with water, dried (MgSO$_4$) and the solvent removed. The residue is purified by column chromatography on silica gel with 5% methanol in chloroform as eluent to give 0.45 g of solid: mass spectrum (CI) 499 (M+1).

The following Examples are prepared as described for Example 120 with formaldehyde and the appropriate amine.

EXAMPLE 121

N-[5-[[3-[(Dimethylamino)methyl]-[5H-pyrrolo[2,1-c][1,4]benzodiazepin-10(11H)]-yl]carbonyl]-2-pyridinyl]-5-chloro -2-methylbenzamide

EXAMPLE 122

N-[5-[[3-[(Dimethylamino)methyl]-[5H-pyrrolo[2,1-c][1,4]benzodiazepin-10(11H)]-yl]carbonyl]-2-pyridinyl]-3-fluoro-2-methylbenzamide

EXAMPLE 123

N-[5-[[3-[(Dimethylamino)methyl]-[5H-pyrrolo[2,1-c][1,4]benzodiazepin-10(11H) -yl]carbonyl]-2-pyridinyl]-2-chloro-4-fluorobenzamide

EXAMPLE 124

N-[5-[[3-[(Dimethylamino)methyl]-[5H-pyrrolo[2,1-c][1,4]benzodiazepin-10(11H)]-yl]carbonyl]-2-pyridinyl]-2-chloro-5-fluorobenzamide

EXAMPLE 125

N-[5-[[3-[(Dimethylamino)methyl]-[5H-pyrrolo[2,1-c][1,4]benzodiazepin-10(11H)]-yl carbonyl]-2-pyridinyl]-2-chlorobenzamide

EXAMPLE 126

N-[5-[[3-[(Dimethylamino)methyl]-[5H-pyrrolo[2,1-c][1,4]benzodiazepin-10(11H)]-yl]carbonyl]-2-pyridinyl]-2-fluoro-5-chlorobenzamide

EXAMPLE 127

N-[5-[[3-[(Dimethylamino)methyl]-5H-pyrrolo[2,1-c][1,4]benzodiazepin-10(11H)]-yl]carbonyl]-2-pyridinyl]-2,4-dichlorobenzamide

EXAMPLE 128

N-[5-[[3-(1-Pyrrolidinylmethyl)-5H-pyrrolo[2,1-c][1,4]benzodiazepin-10(11H)-yl]carbonyl]-2-pyridinyl]-2-chloro-4-fluorobenzamide

EXAMPLE 129

N-[5-[[3-[(Dimethylamino)methyl]-5H-pyrrolo[2,1-c][1,4]benzodiazepin-10(11H)]-yl]carbonyl]-2-pyridinyl ]-2-chlorobenzeneacetamide

EXAMPLE 130

N-[2-(Dimethylamino)ethyl]-N-[5-(5H-pyrrolo[2,1-c][1,4]benzodiazepin-10(11H) -ylcarbonyl)-2-pyridinyl]-5-fluoro-2-methylbenzamide To a solution of 0.75 g of 10-[[6-[2-(dimethylamino)ethylamino]-3-pyridinyl]carbonyl]-10,11-dihydro-5H-pyrrolo[2,1-c][1,4]benzodiazepine and 5 ml of diisopropylethylamine in 75 ml of dichloromethane is added (slowly) 0.35 g of 5-fluoro-2-methylbenzoyl chloride in 10 ml of dichloromethane. The mixture is stirred at room temperature for 16 hours and the solution washed well with water. The organic layer is dried (MgSO$_4$) and the solvent removed under vacuum. The residue is purified by column chromatography on silica gel with 30% methanol in chloroform as eluent to give 0.80 g of yellow solid; mass spectrum (CI), 511 (M+1).

EXAMPLE 131

N-[3-(Dimethylamino)propyl]-N-[5-(5H-pyrrolo[2,1-c][1,4]benzodiazepin-10(11H) -ylcarbonyl)-2-pyridinyl]-5-fluoro-2-methylbenzamide A solution of 6.35 g of 5-fluoro-2-methylbenzoyl chloride in 10 ml of dichloromethane is added to a solution of 2 mmol of 10-[[6-[3-(dimethylamino)propylamino]-3-pyridinyl]carbonyl]-10,11-dihydro-5H-pyrrolo[2,1-c][1,4]benzodiazepine and 5 ml of diisopropylethylamine in 75 ml of dichloromethane. The solution is stirred 16 hours at room temperature, washed with water, dried (MgSO$_4$) and the solvent removed. The residue is purified by column chromatography over silica gel with 30% methanol in chloroform as eluent to give 0.75 g of solid; mass spectrum (CI) 525 (M+1).

EXAMPLE 132

N-[2-(Dimethylamino)methyl]-N-5-(5H-pyrrolo[2,1-c][1,4]benzodiazepin-10(11H)-ylcarbonyl)-2-pyridinyl]-5-fluoro- 3-methylbenzamide As described for Example 130, a solution of 2 mmol of 10-[[6-[2-(dimethylamino)methylamino]-3-pyridinyl]carbonyl]-10,11-dihydro-5H-pyrrolo[2,1-c][1,4]benzodiazepine, 8 ml of diisopropylethylamine, and 2.2 mmol of 5-fluoro-2-methylbenzoyl chloride in 100 ml of dichloromethane is stirred at room temperature for 16 hours. The solvent is removed and the product purified by chromatography on silica gel to give a solid.

EXAMPLE 133

N-[5-[[3-[(Dimethylamino)methyl]-[5H-pyrrolo[2.1-c][1,4]benzodiazepin-10(11H)]yl]carbonyl]-2-pyridinyl]-3,4,5-trimethoxybenzamide A mixture of 1.0 g of N-[5-(5H-pyrrolo[2,1c][1,4]benzodiazepin-10(11H) -ylcarbonyl)-2-pyridinyl]3,4,5-trimethoxybenzamide, 10 ml of 40% aqueous dimethylamine, 10 ml of 35% aqueous formaldehyde in 50 ml of tetrahydrofuran-methanol (1:1) plus 1 drop of acetic acid is refluxed for 16 hours. The mixture is concentrated and the residue extracted with chloroform. The extract is washed with water, dried (MgSO$_4$), concentrated and the residue purified by column chromatography (silica gel) with 5% methanol in chloroform as eluent. The fractions containing product are combined to give 0.80 g of solid; mass spectrum (CI) 556 (M+1).

EXAMPLE 134

N-[5-(Pyrido[3,2-e]pyrrolo[1,2-a]pyrazin-5(6H)ylcarbonyl)-2-pyridinyl]-5-fluoro-2-methylbenzamide To a chilled (0° C.) solution of 0.343 g of 5,6-dihydropyrido[3,2-e]pyrrolo[1,2-a]pyrazine and 1.1 ml of triethylamine in 5 ml of dichloromethane is added 1.17 g of 6-(5-fluoro-2-methylbenzoyl)aminopyridine-3-carbonyl chloride. The mixture is stirred at room temperature for 16 hours. To the mixture is added 50 ml of dichloromethane and 20 ml of water. The organic layer is separated and washed with 20 ml each of 1M NaHCO₃ and brine. The organic layer is dried (Na₂SO₄) and passed through a thin pad of hydrous magnesium silicate and the pad washed with dichloromethane. The filtrate is concentrated and the residue chromatographed on silica gel prep-plates with ethyl acetate-hexane (1:1) as eluent. The product is crystallized from ethyl acetate to give 0.38 g of white crystals, m.p. 226°–234° C.

As described for Example 134 the following compounds are prepared (Table F).

TABLE F

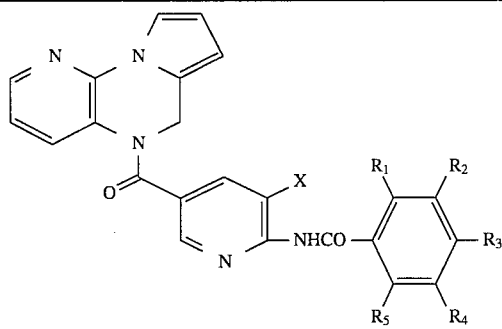

| Ex No. | R₁ | R₂ | R₃ | R₄ | R₅ | X |
|---|---|---|---|---|---|---|
| 135 | H | CH₃ | H | H | H | H |
| 136 | H | CH₃ | H | H | H | Br |
| 137 | H | CH₃ | H | H | H | Cl |
| 138 | H | H | CH₃ | H | H | H |
| 139 | H | H | CH₃ | H | H | Br |
| 140 | H | H | CH₃ | H | H | Cl |
| 141 | Cl | H | H | H | H | H |
| 142 | Cl | H | H | H | H | Br |
| 143 | Cl | H | H | H | H | Cl |
| 144 | H | Cl | H | H | H | H |
| 145 | H | Cl | H | H | H | Br |
| 146 | H | Cl | H | H | H | Cl |
| 147 | H | H | Cl | H | H | H |
| 148 | H | H | Cl | H | H | Br |
| 149 | H | H | Cl | H | H | Cl |
| 150 | Cl | Cl | H | H | H | H |
| 151 | Cl | Cl | H | H | H | Br |
| 152 | Cl | Cl | H | H | H | Cl |
| 153 | Cl | H | Cl | H | H | H |
| 154 | Cl | H | Cl | H | H | Br |
| 155 | Cl | H | Cl | H | H | Cl |
| 156 | Cl | H | H | H | Cl | H |
| 157 | Cl | H | H | H | Cl | Br |
| 158 | Cl | H | H | H | Cl | Cl |
| 159 | H | Cl | Cl | H | H | H |
| 160 | H | Cl | Cl | H | H | Br |
| 161 | H | Cl | Cl | H | H | Cl |
| 162 | F | H | F | H | H | H |
| 163 | F | H | F | H | H | Br |
| 164 | F | H | F | H | H | Cl |
| 165 | F | H | H | F | H | H |
| 166 | F | H | H | F | H | Br |
| 167 | F | H | H | F | H | Cl |
| 168 | F | H | H | H | F | H |
| 169 | F | H | H | H | F | Br |
| 170 | F | H | H | H | F | Cl |

EXAMPLE 171

N-[5-(Pyrrolo[1,2a]quinoxalin-5(4H)-ylcarbonyl)-2-pyridinyl]-5-fluoro-2-methylbenzamide To a chilled (0° C.) solution of 0.341 g of 4,5-dihydropyrrolo[1,2-a]quinoxaline and 1.11 ml of triethylamine in 5 ml of dichloromethane is added 1.17 g of 6-[(5-fluoro-2-methylbenzoyl)amino]pyridine-3-carbonyl chloride. The mixture is stirred under argon at room temperature for 16 hours. The mixture is diluted with 50 ml of dichloromethane and 20 ml of water and the organic layer is separated. The organic layer is washed with 20 ml each of 1M NaHCO₃ and brine and dried (Na₂SO₄). The solution is filtered through a thin pad of hydrous magnesium silicate and the pad washed with dichloromethane. The filtrate is concentrated and the residue purified on silica gel prep-plates with ethyl acetate-hexane (1:1) as solvent to give a solid. The solid is crystallized from ethyl acetate to give 0.38 g of crystals, m.p. 190°–196° C.

As described for Example 171 the following compounds are prepared (Table G).

TABLE G

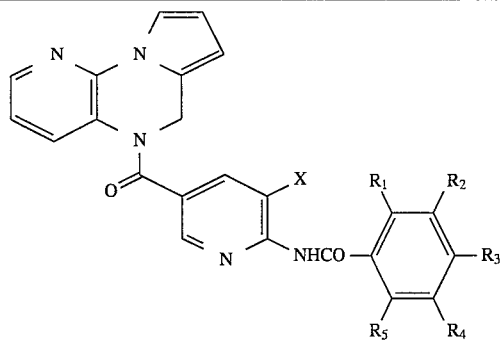

| Ex No. | R₁ | R₂ | R₃ | R₄ | R₅ | X |
|---|---|---|---|---|---|---|
| 172 | H | CH₃ | H | H | H | H |
| 173 | H | CH₃ | H | H | H | Br |
| 174 | H | CH₃ | H | H | H | Cl |
| 175 | H | H | CH₃ | H | H | H |
| 176 | H | H | CH₃ | H | H | Br |
| 177 | H | H | CH₃ | H | H | Cl |
| 178 | Cl | H | H | H | H | H |
| 179 | Cl | H | H | H | H | Br |
| 180 | Cl | H | H | H | H | Cl |
| 181 | H | Cl | H | H | H | H |
| 182 | H | Cl | H | H | H | Br |
| 183 | H | Cl | H | H | H | Cl |
| 184 | H | H | Cl | H | H | H |
| 185 | H | H | Cl | H | H | Br |
| 186 | H | H | Cl | H | H | Cl |
| 187 | Cl | Cl | H | H | H | H |
| 188 | Cl | Cl | H | H | H | Br |
| 189 | Cl | Cl | H | H | H | Cl |
| 190 | Cl | H | Cl | H | H | H |
| 191 | Cl | H | Cl | H | H | Br |
| 192 | Cl | H | Cl | H | H | Cl |
| 193 | Cl | H | H | H | Cl | H |
| 194 | Cl | H | H | H | Cl | Br |
| 195 | Cl | H | H | H | Cl | Cl |
| 196 | H | Cl | Cl | H | H | H |
| 197 | H | Cl | Cl | H | H | Br |
| 198 | H | Cl | Cl | H | H | Cl |
| 199 | F | H | F | H | H | H |
| 200 | F | H | F | H | H | Br |
| 201 | F | H | F | H | H | Cl |
| 202 | F | H | H | F | H | H |
| 203 | F | H | H | F | H | Br |
| 204 | F | H | H | F | H | Cl |
| 205 | F | H | H | H | F | H |
| 206 | F | H | H | H | F | Br |
| 207 | F | H | H | H | F | Cl |

EXAMPLE 208

N-[5-(4H-Pyrazolo[5,1-c][1,4]benzodiazepin-5(10H)ylcarbonyl)-2-pyridinyl]-5-fluoro-2-methyl-benzamide To a chilled (0° C.) solution of 0.37 g of 5,10-dihydro-4H-pyrazolo [5,1-c][1,4]benzodiazepine and 836 microliters of triethylamine in 5 ml of dichloromethane is added 0.761 g of 6-[(5-fluoro-2-methylbenzoyl)amino]pyridine-3-carbonyl chloride. The mixture is stirred at room temperature under argon for 5 hours. An additional 420 microliters of triethylamine and 0.38 g of 6-[(5-fluoro-2-methylbenzoyl)amino]pyridine-3-carbonyl chloride is added and the mixture stirred 16 hours. The mixture is diluted with 60 ml of dichloromethane and washed with 25 ml each of H₂O, 1M NaHCO₃, brine and dried (Na₂SO₄). The solution is filtered (twice) through a thin pad of hydrous magnesium silicate and the pad washed with dichloromethane. The filtrate is concentrated to give a yellow glass (0.68 g) which is crystallized from ethyl acetate to give 0.38 g of white crystals, m.p. 250°–260° C.; mass spectrum (FABL) 442.4 (M+H).

TABLE H

| Ex No. | $R_1$ | $R_2$ | $R_3$ | $R_4$ | $R_5$ | X |
|---|---|---|---|---|---|---|
| 209 | H | CH₃ | H | H | H | H |
| 210 | H | CH₃ | H | H | H | Br |
| 211 | H | CH₃ | H | H | H | Cl |
| 212 | H | H | CH₃ | H | H | H |
| 213 | H | H | CH₃ | H | H | Br |
| 214 | H | H | CH₃ | H | H | Cl |
| 215 | Cl | H | H | H | H | H |
| 216 | Cl | H | H | H | H | Br |
| 217 | Cl | H | H | H | H | Cl |
| 218 | H | Cl | H | H | H | H |
| 219 | H | Cl | H | H | H | Br |
| 220 | H | Cl | H | H | H | Cl |
| 221 | H | H | Cl | H | H | H |
| 222 | H | H | Cl | H | H | Br |
| 223 | H | H | Cl | H | H | Cl |
| 224 | Cl | Cl | H | H | H | H |
| 225 | Cl | Cl | H | H | H | Br |
| 226 | Cl | Cl | H | H | H | Cl |
| 227 | Cl | H | Cl | H | H | H |
| 228 | Cl | H | Cl | H | H | Br |
| 229 | Cl | H | Cl | H | H | Cl |
| 230 | Cl | H | H | H | Cl | H |
| 231 | Cl | H | H | H | Cl | Br |
| 232 | Cl | H | H | H | Cl | Cl |
| 233 | H | Cl | Cl | H | H | H |
| 234 | H | Cl | Cl | H | H | Br |
| 235 | H | Cl | Cl | H | H | Cl |
| 236 | F | H | F | H | H | H |
| 237 | F | H | F | H | H | Br |
| 238 | F | H | F | H | H | Cl |
| 239 | F | H | H | F | H | H |
| 240 | F | H | H | F | H | Br |
| 241 | F | H | H | F | H | Cl |
| 242 | F | H | H | H | F | H |
| 243 | F | H | H | H | F | Br |
| 244 | F | H | H | H | F | Cl |

EXAMPLE 245

N-[5-(4H-Pyrazolo[5,1-c][1,4]benzodiazepin-5(10H)ylcarbonyl)-2-pyridinyl]-[1,1'-biphenyl]-2-carboxamide To a chilled (0° C.) solution of 0.185 g of 5,10-dihydro-4H-pyrazolo[5,1-c][1,4]benzodiazepine and 417 µl of triethylamine in 3.5 ml of dichloromethane is added 0.35 g of 6-(2-biphenylcarbonyl)aminopyridine-3-carbonyl chloride in 1.5 ml of dichloromethane. The mixture is stirred at room temperature under argon for 16 hours, diluted with 40 ml of dichloromethane and 20 ml of water. The organic layer is separated, washed with 20 ml of brine and dried (Na₂SO₄). The solution is filtered through a thin pad of hydrous magnesium silicate. The filtrate is concentrated to dryness under vacuum to give 0.4 g of solid. The solid is purified on silica gel prep-plates with ethyl acetate-hexane (3:1) as eluent to give 170 mg of a brown glass, m.p. 110°–150° C.

As described for Example 245, the following derivatives are prepared (Table H).

TABLE H

| Ex. No. | $R_1$ | X | $R_2$ |
|---|---|---|---|
| 246 | H | Cl | phenyl |

TABLE H-continued

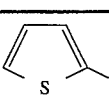

| Ex. No. | R₁ | X | R₂ |
|---|---|---|---|
| 247 | H | H | 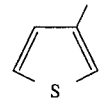 (2-thienyl) |
| 248 | H | H | 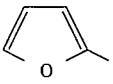 (3-thienyl) |
| 249 | H | H | 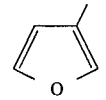 (2-furyl) |
| 250 | H | H | 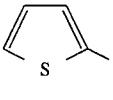 (3-furyl) |
| 251 | Cl | Cl | 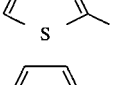 (2-thienyl) |
| 252 | Cl | H | 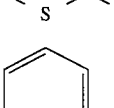 (2-thienyl) |
| 253 | H | Cl | 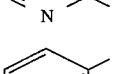 (2-thienyl) |
| 254 | H | H | 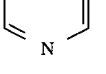 (2-pyridyl) |
| 255 | Cl | H | 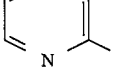 (3-pyridyl) |
| 256 | H | Cl | 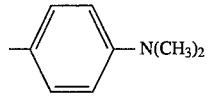 (2-pyridyl) |
| 257 | H | H | 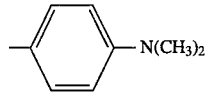 -C₆H₄-N(CH₃)₂ |
| 258 | H | Cl | -C₆H₄-N(CH₃)₂ |

TABLE H-continued

| Ex. No. | R₁ | X | R₂ |
|---|---|---|---|
| 259 | H | H | -C₆H₄-NH₂ |
| 260 | H | H | -C₆H₄-NHCH₃ |

EXAMPLE 261

10-[[6-[(2-Methylpropyl)amino]-3-pyridinyl]carbonyl]-10,11-dihydro-5H-pyrrolo[2,1-c][1,4]benzodiazedine A mixture of 0.16 g of 10-[(6-chloro-3-pyridinyl)carbonyl]-10,11-dihydro-5H-pyrrolo[2,1-c][1,4]benzodiazepine, 40 mg of pyridine and 2 ml of 2-methylpropylamine is stirred and heated at 100° C. in a sealed vessel for 1 hour. To the mixture is added 0.2 ml of N,N-dimethylpropyleneurea and the mixture is heated at 110° C. for 7 hours. The volatiles are removed under vacuum and 10 ml of 0.5N NaOH is added to the residue. The mixture is filtered and the solid washed with water and then hexane. The solid is dissolved in ethyl acetate and the solution washed with 0.5N NaOH, brine and dried (Na₂SO₄). The solution is filtered through a thin pad of hydrous magnesium silicate and the filtrate concentrated to dryness. The residue is triturated with diisopropylether-hexane to give 0.18 g of white solid; mass spectrum (CI) 361 (M+H).

As described for Example 261, the following derivatives are prepared (Table I).

TABLE I

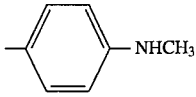

| Ex. No. | D | R |
|---|---|---|
| *262 | C | -CH₂CH₂C(CH₃)₃ |

TABLE I-continued

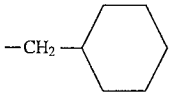

| Ex. No. | D | R |
|---|---|---|
| **263 | C | 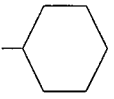 |
| 264 | C | 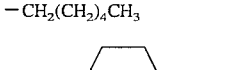 |
| 265 | C | —CH$_2$CH$_2$C(CH$_3$)$_2$CH$_2$CH$_3$ |
| 266 | C | —CH$_2$(CH$_2$)$_4$CH$_3$ |
| 267 | C | 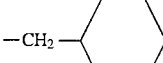 |
| 268 | C | —CH$_2$CH$_2$CH(CH$_3$)$_2$ |
| 269 | N | —CH$_2$CH$_2$C(CH$_3$)$_3$ |
| 270 | N | 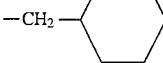 |
| 271 | N | 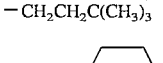 |
| 272 | N | —CH$_2$(CH$_2$)$_4$CH$_3$ |

*mass spectrum (CI) 389 (M + 1)
**mass spectrum (CI) 401 (M + 1)

EXAMPLE 273

10-[[6-[(Phenylmethyl)amino]-3-pyridinyl]carbonyl]-10,11-dihydro-5H-pyrrolo[2,1-c][1,4]benzodiazepine A mixture of 0.16 g of 10-[(6-chloro-3-pyridinyl)carbonyl]-10,11-dihydro-5H-pyrrolo[2,1-c][1,4]benzodiazepine, 0.5 ml of benzylamine and 0.2 ml of N,N'-dimethylpropyleneurea is stirred and heated at 110° C. for 7 hours. After cooling to room temperature, the mixture is washed with hexane (3 times 10 ml). The residue is dissolved in water and made alkaline with 1N NaOH. The suspension is washed with H$_2$O and extracted with ethyl acetate. The organic extract is washed with brine, dried (Na$_2$SO$_4$) and filtered through a thin pad of hydrous magnesium silicate. The filtrate is evaporated and the residue triturated with diethyl ether-hexane to give 0.20 g of white solid; mass spectrum (CI) 395 (M+H).

As described for Example 273, the following derivatives are prepared (Table J).

TABLE J

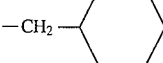

| Ex. No. | D | R |
|---|---|---|
| 274 | C |  |
| 275 | C | 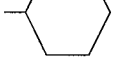 |
| 276 | C | 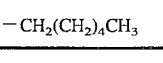 |
| 277 | C | 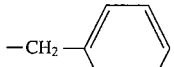 |
| 278 | C | 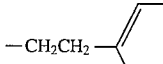 |
| 279 | C | 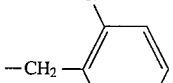 |
| 280 | C | 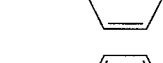 |
| 281 | N |  |
| 282 | N | 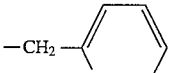 |
| 283 | N | 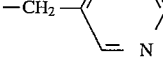 |
| 284 | N | 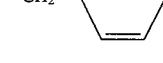 |

TABLE J-continued

[Structure: benzodiazepine with pyrrole/pyrazole (D), N-C(=O)-pyridine-NHR]

| Ex. No. | D | R |
|---------|---|---|
| 285 | N | −CH₂CH₂−(thiophene-2-yl) |
| 286 | N | −CH₂CH₂−(phenyl) |
| 287 | N | −CH₂−(pyridin-3-yl) |

EXAMPLE 288

10,11-Dihydro-10-[[6-(cyclohexylthio)-3-pyridinyl]carbonyl]-5H-pyrrolo-[2,1-c][1,4]benzodiazepine

To a suspension of 35 mg of sodium hydride (60% in oil) in 3 ml of tetrahydrofuran is added under argon 0.10 g of cyclohexylmercaptan. A white precipitate forms and after 0.5 hour at room temperature, 1 ml of N,N'-dimethylpropyleneurea is added. To the mixture is added 0.13 g of 10-[(6-chloro-3-pyridinyl)carbonyl]-10,11-dihydro-5H-pyrrolo[2,1-c][1,4]benzodiazepine in 2 ml of tetrahydrofuran. The mixture is stirred at room temperature for 18 hours, quenched with water and ammonium chloride and concentrated under vacuum. The aqueous suspension is filtered and the solid washed with water and hexane. The solid is purified by chromatography on silica gel prep-plates with ethyl acetate-hexane (1:4) as eluent to give 0.13 g of white solid; mass spectrum (CI): 404 (M+H).

As described for Example 288, the following derivatives are prepared (Table K).

TABLE K

[Structure: benzodiazepine with D-containing 5-ring bearing $R_1$, N-C(=O)-pyridine-S-R]

| Ex. No. | D | R |
|---------|---|---|
| 289 | C | −CH₂−(cyclohexyl) |
| 290 | C | −CH₂−(phenyl) |
| 291 | C | −CH₂CH₂C(CH₃)₃ |
| 292 | C | −CH₂CH₂−(phenyl) |
| 293 | C | −CH₂CH₂−(thiophene-2-yl) |
| 294 | N | −CH₂−(cyclohexyl) |
| 295 | N | −CH₂−(phenyl) |
| 296 | N | −CH₂CH₂C(CH₃)₃ |
| 297 | N | −CH₂CH₂−(phenyl) |
| 298 | N | −CH₂CH₂−(thiophene-2-yl) |
| 299 | N | −CH₂−(pyridin-3-yl) |
| 300 | C | −CH₂−(pyridin-2-yl) |

EXAMPLE 301

10,11-Dihydro-10-[[6-[(2-methylphenyl)amino]-3-pyridinyl]carbonyl]-5H-pyrrolo[2,1-c][1,4]benzodiazepine A mixture of 0.5 g of 10-[(6-chloro-3-pyridinyl)carbonyl]-10,11-dihydro-5H-pyrrolo[2,1c-1[1,4]benzodiazepine and 0.36 g of o-toluidine in 60 ml of N,N-dimethylformamide is refluxed for 16 hours. The mixture is poured into 200 ml of ice-water and extracted with three 100 ml portions of chloroform. The extract is washed with water, dried ($Na_2SO_4$) and the solvent removed. The residue is purified by chromatography on silica gel prep-plates with hexane-ethyl acetate (5:1) as solvent to give 0.56 g of yellow solid: mass spectrum (CI) 395.2 (M+H).

As described for Example 301, the following derivatives are prepared (Table L).

TABLE L

| Ex No. | D | R | $R_1$ | $R_2$ | $R_3$ | $R_4$ | $R_5$ |
|---|---|---|---|---|---|---|---|
| 302 | C | H | Cl | H | H | H | H |
| 303 | C | H | Cl | H | Cl | H | H |
| 304 | C | H | Cl | H | H | F | H |
| 305 | C | H | F | H | F | H | H |
| 306 | C | H | $CH_3$ | H | H | F | H |
| 307 | C | H | $CF_3$ | H | H | H | H |
| 308 | C | $CH_3$ | $CH_3$ | H | H | H | H |
| 309 | C | H | H | H | H | H | H |
| 310 | N | H | H | H | H | H | H |
| 311 | N | $CH_3$ | H | H | H | H | H |
| 312 | N | H | $CF_3$ | H | Cl | H | H |
| 313 | N | H | $CH_3$ | H | H | F | H |
| 314 | N | H | F | H | F | H | H |
| 315 | N | H | Cl | H | H | F | H |
| 316 | N | H | Cl | H | Cl | H | H |
| 317 | N | H | Cl | H | H | H | H |

EXAMPLE 318

N-[4-(5H-Pyrrolo[2,1-c][1,4]benzodiazepin-10(11H)ylcarbonyl)-2-methoxyphenyl][1,1'-biphenyl]-2-carboxamide To a solution of 0.70 g of 10,11-dihydro-5H-pyrrolo[2,1-c][1,4]benzodiazepine and 0.56 g of N,N-diisopropylethylamine in 50 ml of methylene chloride is added 1.35 g of 4-[([1,1'-biphenyl]-2-carbonyl)amino]-3-methoxybenzoyl chloride followed by stirring at room temperature for 18 hours. The reaction mixture is washed with water and saturated aqueous $NaHCO_3$ and the organic layer dried($Na_2SO_4$). The organic layer is passed through hydrous magnesium silicate and the filtrate concentrated in vacuo to give a residue which is dissolved in methylene chloride and passed through a pad of hydrous magnesium silicate two additional times to give upon concentration in vacuo to give 1.5 g of amorphous solid. M+=512.

EXAMPLE 319

N-[b 4-(5H-Pyrrolo[2,1-c][1,4]benzodiazepin-10(11H)ylcarbonyl)-3-chlorophenyl][1,1'-biphenyl]-2-carboxamide To a solution of 0.52 g of 10,11-dihydro-5H-pyrrolo[2,1-c][1,4]benzodiazepine and 0.39 g of N,N-diisopropylethylamine in 25 ml of methylene chloride is added 1.1 g of 4-[([1,1'-biphenyl]-2-carbonyl)amino]-2chlorobenzoyl chloride followed by stirring at room temperature for 18 hours. The reaction mixture is washed with water and saturated aqueous $NaHCO_3$ and the organic layer dried($Na_2SO_4$). The organic layer is passed through hydrous magnesium silicate and the filtrate concentrated in vacuo to give a residue which is dissolved in methylene chloride and passed through hydrous magnesium silicate two additional times to give upon concentration in vacuo 1.10 g of the desired product as a residue. $M^+$=516,518,520.

EXAMPLE 320

N-[4-(5H-Pyrrolo[2,1-c][1,4]benzodiazepin-10(11H)ylcarbonyl)phenyl][1,1'-biphenyl]-2-carboxamide To a solution of 0.65 g of 10,11-dihydro-5H-pyrrolo[2,1-c][1,4]benzodiazepine and 0.52 g of N,N-diisopropylethylamine in 25 ml of methylene chloride is added 1.34 g of 4-[([1,1'-biphenyl]-2-carbonyl)amino]benzoyl chloride followed by stirring at room temperature for 18 hours. The reaction mixture is washed with water and saturated aqueous $NaHCO_3$ and the organic layer dried($Na_2SO_4$). The organic layer is passed through hydrous magnesium silicate and the filtrate concentrated in vacuo to give a residue which is dissolved in methylene chloride and passed through hydrous magnesium silicate two additional times to give upon concentration in vacuo to give 1.02 g of the desired product as a residue. $M^+$=482.

EXAMPLE 321

N-[4-(5H-Pyrrolo[2,1-c][1,4]benzodiazepine-10(11H)ylcarbonyl)phenyl]-2-(phenylmethyl)benzamide To a solution of 0.75 g of 10,11-dihydro-5H-pyrrolo[2,1-c][1,4]benzodiazepine and 0.57 g of N,N-diisopropylethylamine in 50 ml of methylene chloride is added 1.53 g of 4-[[2-(phenylmethyl)benzoyl]amino]benzoyl chloride followed by stirring at room temperature for 18 hours. The reaction mixture is washed with water and saturated aqueous $NaHCO_3$ and the organic layer dried($Na_2SO_4$)o The organic layer is passed through hydrous magnesium silicate and the filtrate concentrated in vacuo to give a residue which is dissolved in methylene chloride and passed through hydrous magnesium silicate two additional times to give upon concentration in vacuo to give 1.97 g of the desired product as an amorphous solid.

EXAMPLE 322

N-[4-(5H-Pyrrolo[2,1-c][1,4]benzodiazepin-10(11H)ylcarbonyl)-3-chlorophenyl]-2-(phenylmethyl)benzamide To a solution of 0.92 g of 10,11-dihydro-5H-pyrrolo[2,1-c][1,4]benzodiazepine and 0.72 g of N,N-diisopropylethylamine in 50 ml of methylene chloride is added 2.4 g of 2-chloro-4-[[(2-phenylmethyl)benzoyl]amino]benzoyl chloride followed by stirring at room temperature for 18 hours. The reaction mixture is washed with water and saturated aqueous NaHCO₃ and the organic layer dried(Na₂SO₄). The organic layer is passed through hydrous magnesium silicate and the filtrate concentrated in vacuo to give a residue which is dissolved in methylene chloride and passed through hydrous magnesium silicate two additional times to give upon concentration in vacuo 2.87 g of the desired product as an amorphous compound.

EXAMPLE 323

N-[4-(5H-Pyrrolo[2,1-c][1,4]benzodiazepin-10(11H)ylcarbonyl)-2-methoxyphenyl]-2-(phenylmethyl)benzamide To a solution of 0.75 g of 10,11-dihydro-5H-pyrrolo[2,1-c][1,4]benzodiazepine and 0.58 g of N,N-diisopropylethylamine in 50 ml of methylene chloride is added 1.69 g of 3-methoxy-4-[[(2-phenylmethyl)benzoyl]amino]benzoyl chloride followed by stirring at room temperature for 18 hours. The reaction mixture is washed with water and saturated aqueous NaHCO₃ and the organic layer dried(Na₂SO₄). The organic layer is passed through hydrous magnesium silicate to give upon concentration in vacuo 1.92 g of the desired product as an amorphous solid.

EXAMPLE 324

N-[4-(5H-Pyrrolo[2,1-c][1,4]benzodiazepin-10(11H)ylcarbonyl)phenyl]-4'-(trifluoromethyl)[1,1'-biphenyl]-2-carboxamide A solution of 1.14 g of [4'-(trifluoromethyl)[1,1'-biphenyl]-2-carbonyl chloride in 10 ml of methylene chloride is added dropwise to an ice cold solution of 1.0 g of 10,11-dihydro-10-(4-aminobenzoyl)-5H-pyrrolo[2,1-c][1,4]benzodiazepine and 0.52 g of N,N-diisopropylethylamine in 25 ml of methylene chloride. The reaction mixture is stirred at room temperature for 18 hours and washed with water, saturated aqueous NaHCO₃ and the organic layer dried(Na₂SO₄). The organic layer is passed through a pad of hydrous magnesium silicate two times to give 1.70 g of the desired product as an amphorous compound.

EXAMPLE 325

N-[4-(5H-Pyrrolo[2,1-c][1,4]benzodiazepin-10(11H)ylcarbonyl)-3-methoxyphenyl][4'-(trifluoromethyl)[1,1'-biphenyl]-2-carboxamide A solution of 1.87 g of [4'-(trifluoromethyl)[1,1'-biphenyl]-2-carbonyl chloride in 10 ml of methylene chloride is added dropwise to an ice cold solution of 0.74 g of 10,11-dihydro-10-(4-aminobenzoyl)-5H-pyrrolo[2,1-c][1,4]benzodiazepine and 0.56 g of N,N-diisopropylethylamine in 50 ml of methylene chloride. The reaction mixture is stirred at room temperature for 18 hours and washed with water, saturated aqueous NaHCO₃ and the organic layer dried(Na₂SO₄). The organic layer is passed through a pad of hydrous magnesium silicate two times to give the desired product as a residue which is crystallized from ethyl acetate to give 2.33 g of the desired product, 211°–212° C.

EXAMPLE 326

N-[4-(5H-Pyrrolo[2,1-c][1,4]benzodiazepin-10(11H)ylcarbonyl)-2-chlorophenyl][4'-(trifluoromethyl)[1,1'-biphenyl]-2-carboxamide A solution of 1.35 g of 2-chloro-4-[([4'-(trifluoromethyl)[1,1'-biphenyl]-2-carbonyl)amino]benzoyl chloride in 10 ml of methylene chloride is added dropwise to an ice cold solution of 0.63 g of 10,11-dihydro-5H-pyrrolo[2,1-c][1,4]benzodiazepine and 0.48 g of N,N-diisopropylethylamine in 50 ml of methylene chloride. The reaction mixture is stirred at room temperature for 18 hours and washed with water, saturated aqueous NaHCO₃ and the organic layer dried(Na₂SO₄). The organic layer is passed through a pad of hydrous magnesium silicate two times to give 1.63 g of the desired product as a non-crystalline solid.

EXAMPLE 327

N-[4-(5H-Pyrrolo[2,1-c][1,4]benzodiazepin-10(11H)ylcarbonyl)phenyl]-2-methylpyridine-3-carboxamide To a stirred solution of 1.0 g of 10,11-dihydro-10-(4-aminobenzoyl)-5[-pyrrolo[2,1-c][1,4]benzodiazepine and 3 ml of N,N-diisopropylethylamine in 100 ml of methylene chloride is slowly added 600 mg of 2-methylpyridine-3-carbonyl chloride dissolved in 15 ml of methylene chloride. The reaction mixture is stirred at room temperature for 2 hours. The reaction mixture is quenched with water and the organic layer washed well with water. The organic layer is dried(MgSO₄), filtered and evaporated in vacuo to a residue which is purified by column chromatography on silica gel by elution with 1:1 ethyl acetate:hexane to give 800 mg of the desired product as a pale yellow residue. $M^+=422$.

EXAMPLE 328

N-[4-(5H-Pyrrolo[2,1-c][1,4]benzodiazepin-10(11H)-ylcarbonyl)-3-chlorophenyl]-2-methylpyridine-3-carboxamide A mixture of 1.1 g of 10,11-dihydro-10-(4-amino-2-chlorobenzoyl)-5H-pyrrolo[2,1-c]1[1,4]benzodiazepine and 3 ml of N,N-diisopropylethylamine in 100 ml of methylene chloride is stirred while a solution of 600 mg of 2-methylpyridine-3-carbonyl chloride in 15 ml of methylene chloride is added slowly. The reaction mixture is stirred at room temperature for 2 hours. The reaction mixture is quenched with water and the organic layer washed with water, dried(MgSO₄), filtered and evaporated in vacuo to a residue. The product is purified by column chromatography on silica gel by elution with 1:1 ethyl acetate:hexane to give the desired product as a pale yellow residue. $M^+=456$.

EXAMPLE 329

N-[5-(5H-Pyrrolo[2,1-c][1,4]benzodiazepin-10(11H)ylcarbonyl]-2-pyridinyl]-2-methylpyridine-3-carboxamide A mixture of 2.5 g of 6-[[3-(2-methylpyridinyl)carbonyl]amino]pyridine-3-carboxylic acid and 25 ml of thionyl chloride is refluxed for 3 hours and the mixture evaporated to dryness in vacuo to give a solid. A solution of the solid in 50 ml of methylene chloride is added to 2 g of 10,11-dihydro-5H-pyrrolo[2,1-c][1,4]benzodiazepine dissolved in 50 ml of dichloromethane containing 3 ml of N,N-diisopropylethylamine at room temperature. The reaction mixture is stirred at room temperature for 2 hours and quenched with water; washed with water; dried(MgSO$_4$), filtered and evaporated in vacuo to a residue. The residue is purified by column chromatography on silica gel by elution with 1:1 ethyl acetate:hexane to give 2.0 g of the desired product as a solid. M$^+$=423.

EXAMPLE 330

N-[5-(5H-Pyrrolo[2,1-c][1,4]benzodiazepin-10(11H)ylcarbonyl]-2-pyridinyl]-2-methylpyridine-3-carboxamide Hydrochloride To a solution of 1.0 g of N-[5-(5H-pyrrrolo[2,1-c][1,4]benzodiazepin-10(11H)-ylcarbonyl)-2-pyridinyl]-2-methylpyridine-3-carboxamide in 50 ml of methanol is added hydrogen chloride gas. The mixture is stirred at room temperature for 30 minutes and the solvent removed under vacuum. The residue is triturated with ether to give 1.0 g of the desired product as a solid: mass spectrum (CCl);459(M$^+$).

EXAMPLE 331

N-[4-(5H-Pyrrolo[2,1-c][1,4]benzodiazepin-10(11H)ylcarbonyl)phenyl]-2-[N-methylpiperazine]-pyridine-3-carboxamide Hydrochloride The method of Example 330 is used to prepare the desired product as a solid: M$^+$=543.

EXAMPLE 332

N-[4-(5H-Pyrrolo[2,1-c][1,4]benzodiazepin-10(11H)ylcarbonyl)phenyl]-2-(dimethylamino)-pyridine-3-carboxamide Hydrochloride The method of Example 330 is used to prepare the desired product as a solid: M$^+$=487.

EXAMPLE 333

N-[4-(5H-Pyrrolo[2,1-c][1,4]benzodiazepin-10(11H)ylcarbonyl)phenyl]-2-Chloropyridine-3-carboxamide To a stirred solution of 6.06 g of 10,11-dihydro-10-(4-aminobenzoyl)-5H-pyrrolo[2,1-c]1[1,4]benzodiazepine and 10 ml of N,N-diisopropylethylamine is added a solution of 4.0 g of 2-chloropyridine-3-carbonyl chloride in 25 ml of methylene chloride. The reaction mixture is stirred at room temperature for 1 hour. The reaction mixture is quenched with water and the organic layer washed well with water. The organic layer is dried, filtered and evaporated in vacuo to a pale yellow product which is crystallized from 1:1 ethyl acetate:hexane to give 7.0 g of the desired product; M$^+$=442.

EXAMPLE 334

N-[4-(5H-Pyrrolo[2,1-c][1,4]benzodiazedine-10(11H)ylcarbonyl)phenyl]-2-(methylamino)pyridine-3-carboxamide A mixture of 1 g of N-[4-(5H-pyrrolo[2,1-c][1,4]benzodiazepin-10(11H)-ylcarbonyl)phenyl]-2-chloropyridine-3-carboxamide, 1 g of K$_2$CO$_3$ and 10 ml of a 40% solution of monomethylamine is heated in 25 ml of dimethylsulfoxide for 8 hours at 100° C. The reaction mixture is poured over water and the pale yellow solid separated. The reaction mixture is filtered and the collected solid washed well with water. After drying the solid is purified by column chromatography on silica gel by elution with 9:1 ethyl acetate:methanol to give 850 mg of the desired product as a pale yellow solid:M$^+$=437.

EXAMPLE 335

N-[4-(5H-pyrrolo[2,1-c][1,4]benzodiazepin-10(11H)ylcarbonyl)phenyl]-2-[(3-dimethylaminopropyl)amino]pyridine-3-carboxamide Using the conditions of Example 334 and N-[4-(5H-pyrrolo[2,1-c][1,4]benzodiazepin-10(11H)-ylcarbonyl)phenyl]-2-chloropyridine-3-carboxamide and 3-(dimethylamino)propylamine gives 900 mg of the desired product:M$^+$=508.

EXAMPLE 336

N-[4-(5H-Pyrrolo[2,1-c][1,4]benzodiazepin-10(11H)ylcarbonyl)phenyl]-2-(1-piperidinyl)-pyridine-3-carboxamide Using the conditions of Example 334 and 1 g of N-[4-(5H-pyrrolo[2,1-c][1,4]benzodiazepin-10(11H)ylcarbonyl)phenyl]-2-chloropyridine-3-carboxamide and 5 ml of piperidine gives 700 mg of the desired product:M$^+$=491.

EXAMPLE 337

N-[4-(5H-pyrrolo[2,1-c][1,4]benzodiazepin-10(11H)ylcarbonyl)phenyl]-2-(4-methyl-1-piperazinyl)-pyridine-5-carboxamide using the conditions of Example 334 and 1 g of N-[4-(5H-pyrrolo[2,1-c][1,4]benzodiazepin-10(11H)ylcarbonyl)phenyl]-2-chloropyridine-3-carboxamide and 5 ml of N-methylpiperazine gives 1 g of the desired product :M$^+$=500.

EXAMPLE 338

N-[4-(5H-Pyrrolo[2,1-c][1,4]benzodiazepin-10(11H)ylcarbonyl)phenyl]-2-(dimethylamino)-pyridine-3-carboxamide using the conditions of Example 334 and 1 g of N-[4-(5H-pyrrolo[2,1-c][1,4]benzodiazepin-10(11H)ylcarbonyl)-phenyl]-2-chloropyridine-3-carboxamide and 10 ml of 40% N,N-dimethylamine gives 700 mg of the desired product :M$^+$=451.

EXAMPLE 339

N-[4-(5H-Pyrrolo[2,1-c][1,4]benzodiazepin-10(11H)-ylcarbonyl)phenyl]-2-(morpholino)-pyridine-3-carboxamide Using the conditions of Example 334 and 1 g of N-[4-(5H-pyrrolo[2,1-c][1,4]benzodiazepin-10(11H)ylcarbonyl)-phenyl]-2-chloropyridine-3-carboxamide and 5 ml of morpholine gives 800 mg of the desired product:$M^+$=493.

EXAMPLE 340

N-[5-(5H-Pyrrolo[2,1-c][1,4]-benzodiazepin-10(11H)ylcarbonyl)-2-pyridinyl][1,1'-biphenyl]-2-carboxamide A mixture of 2.0 g of 6-[([1,1'-biphenyl]-2carbonyl)amino]pyridine-3-carboxylic acid and 20 ml of thionyl chloride is refluxed for 3 hours. The excess thionyl chloride is removed in vacuo to a residue which is dissolved in 50 ml of methylene chloride. This solution is added added dropwise to a stirred solution of 2.0 g of 10,11-dihydro-5H-pyrrolo [2,1-c][1,4]benzodiazepeine in 50 ml of methylene chloride and 5 ml of N,N-diisopropylethylamine. The reaction mixture is stirred at room temperature for 2 hours and quenched with water. The organic layer is washed well with water and dried over anhydrous $MgSO_4$. The organic layer is concentrated in vacuo to a residue which is purified by column chromatography on silica gel by elution with 40% ethyl acetate:hexane to give 1.2 g of a colorless solid:$M^+$= 484.

EXAMPLE 341

N-[4-(5H-Pyrrolo[2,1-c][1,4]benzodiazepin-10(11H)ylcarbonyl)phenyl]-2-(2-pyridinyl)benzamide A mixture of 1.94 g of N-[4-(5H-pyrrolo[2,1-c][1,4]benzodiazepin-10(11H)-ylcarbonyl)phenyl]-2-bromobenzamide, 2.95 g of 2-pyridyl tri-n-butyl tin and 400 mg of tetrakis(triphenylphosphine)palladium(O) is refluxed for 24 hours in degassed toluene for 24 hours. The reaction mixture is concentrated in vacuo to a residue which is purified by column chromatography on silica gel by elution with 70% ethyl acetate:hexane to give 900 mg of the desired product as a pale yellow solid:M+1=485.

EXAMPLE 342

N-[5-(5H-Pyrrolo[2,1-c][1,4]benzodiazepin-10(11H)ylcarbonyl)-2-pyridinyl]-2-(2-pyridinyl)benzamide A mixture of 484 mg of N-[5-(5H-pyrrolo[2,1-c][1,4] benzodiazepin-10(11H)-ylcarbonyl)-2-pyridinyl]-2-bromobenzamide, 814 mg of 4-(N,N-di-methyl)anilino-tri-n-butyl stannane and 100 mg of tetrakis(triphenylphosphine)palladium (O) is refluxed in degassed toluene for 24 hours. The reaction mixture is concentrated in vacuo to a residue which is purified by column chromatography on silica gel by elution with ethyl acetate to give 200 mg of the desired product: M+1=528.

EXAMPLE 343

10,11-Dihydro-10-(4-(4-butyloxy)benzoyl)-5H-pyrrolo [2,1-c][1,4]benzodiazepine

To a solution of 92 mg of 10,11-dihydro-5-H-pyrrolo[2,1-c][1,4]benzodiazepine in 2 ml of methylene chloride is added 100 mg of triethylamine followed by 130 mg of 4-(n-butyloxy)benzoyl chloride. The reaction mixture is stirred at room temperature for 24 hours and then treated with 4 ml of 1N sodium hydroxide. The mixture is extracted with 10 ml of ethyl acetate and the extract washed with 1N sodium hydroxide and 5 ml of brine. The organic layer is dried over anhydrous sodium sulfate and filtered through hydrous magnesium silicate. The filtrate is concentrate in vacuo to a residue which is stirred with ether-hexanes to give 160 mg of the desired product as a white solid:mass spectrum (CI), 361 ($MH^+$).

EXAMPLE 344

5,10-Dihydro-2-hydroxymethyl-5-(4-(4-butyloxy)benzoyl)-4H-pyrazolo[5,1-c][1,4]benzodiazepine As described for Example 343 4-(n-butyloxy)benzoyl chloride is reacted with 5,10-dihydro-4H-pyrazolo[5,1-c][1,4]benzodiazepine to give the desired product as a solid; mass spectrum (CI), 392 ($MH^+$).

EXAMPLE 345

10,11-Dihydro-10-(4-(5-pentyloxy)benzoyl)-5H-pyrrolo[2,1-c][1,4]benzodiazepine

As described for Example 343 4-(n-pentyloxy)benzoyl chloride is reacted with 10,11-dihydro-5H-pyrrolo[2,1-c][1,4]benzodiazepine to the desired product as a solid:mass spectrum (CI), 375($MH^+$).

EXAMPLE 346

N-[4-(5H-Pyrrolo[2,1-c][1,4]benzodiazepin-10(11H)ylcarbonyl)phenyl]-2-(4-Chlorophenyloxy)pyridine-3-carboxamide The conditions of Example 325 are used with 2-(4-chlorophenyloxy)pyridine-3-carbonyl chloride to give the desired product as a crystalline solid, m.p. 211°–212° C. (M+Na)=557.3.

EXAMPLE 347

N-[4-(5H-Pyrrolo[2,1-c][1,4]benzodiazepin-10(11H)ylcarbonyl)phenyl]-2-methyl-2-(4-chlorophenyloxy)propionamide The conditions of Example 325 are used with 2-(4-chlorophenoxy)-2-methylpropionyl chloride to give the desired product as a solid. M+499.

EXAMPLE 348

10-[[6-(1,1-dimethylethyl)amino]-3-pyridinyl)carbonyl]-10,11-dihydro-5H-pyrrolo[2,1-c][1,4]benzodiazepine Using the conditions of Example 273 and t-butylamine gives the desired product as a beige solid. MS(CI): 361(M+H).

EXAMPLE 349

10-[[6-(1-Methylethyl)amino)-3-pyridinyl)carbonyl]-10,11-dihydro-5H-pyrrolo[2,1-c][1,4]benzodiazepine Using the conditions of Example 273 and isopropylamine gives the desired product as a white solid. MS(CI): 347(M+H).

EXAMPLE 350

10-[[6-(1-Indanylamino)-3-pyridinyl)carbonyl]-10,11-dihydro-5H-pyrrolo[2,1-c][1,4]benzodiazepine Using the conditions of Example 273 and 1-aminoindan gives the desired product as a beige solid. MS(CI): 421(M+H).

EXAMPLE 351

10-[[6-(2,4-Dimethoxyphenylamino)-3-pyridinyl]carbonyl]-10,11-dihydro-5H-pyrrolo[2,1-c][1,4]benzodiazepine Using the conditions of Example 273 with 2,4-dimethoxybenzylamine gives the desired product as a light yellow solid. MS(CI): 455(M+H).

EXAMPLE 352

10-[[6-(2-Bromophenylamino)-3-pyridinyl]carbonyl]-10,11-dihydro-5H-pyrrolo[2,1-c][1,4]benzodiazepine Using the conditions of Example 273 and 2-bromobenzylamine gives the desired product as an off-white solid. MS(CI): 474(M+H).

EXAMPLE 353

N-[5-(5H-Pyrrolo[2,1-c][1,4]benzodiazepin-10(11H)ylcarbonyl)-2-pyridinyl]-2-methylfurane-3-carboxamide Using the conditions of Example 1 with Reference Example 39 to give Reference Example 86 and stirring overnight gives the desired product as white crystals after column chromatography on silica gel by elution with 1:1 ethyl acetate:hexane and crystallization from ethyl acetate, m.p. 210°–212° C.

EXAMPLE 354

N-[5-(5H-Pyrrolo[2,1-c][1,4]benzodiazepin-10(11H)ylcarbonyl)-2-pyridinyl]-2-aminobenzamide A room temperature solution of 1.0 g of N-[5-(5H-pyrrolo[2,1-c]1[1,4]benzodiazepin-10(11H)ylcarbonyl)-2-pyridinyl]-2-nitrobenzamide in 100 ml of ethyl alcohol is hydrogenated over 200 mg of 10% Pd/C in a Parr apparatus under 40 psi of hydrogen for 2 hours. The reaction mixture is filtered through diatomaceous earth and the cake washed with additional ethyl alcohol. The combined filtrates are concentrated in vacuo and the residue purified by crystallization from 2:1 ethyl acetate:hexane to give the desired product as pale yellow crystals: M+Na 445:M$^+$423.

Binding Assay to Rat Hepatic $V_1$ Receptors

Rat liver plasma membranes expressing the vasopressin $V_1$ receptor subtypes are isolated by sucrose density gradient according to the method described by Lesko et al, (1973). These membranes are quickly suspended in 50.0 mM Tris.HCl buffer, pH 7.4, containing 0.2% bovine serum albumin (BSA) and 0.1 mM phenylmethylsulfonylfluoride (PMSF) and kept frozen at −70° C. until used in subsequent binding experiments. For binding experiments, the following is added to the wells of a ninety-six well format microtiter plate: 100 µl of 100.0 mM Tris.HCl buffer containing 10.0 mM $MgCl_2$, 0.2% heat inactivated BSA and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 µl of [phenylalanyl-3,4,5,-$^3$H]vasopressin (S.A. 45.1 Ci/mmole) at 0.8 nM, and the reaction initiated by the addition of 80 µl of tissue membranes containing 20 µg of tissue protein. The plates are kept undisturbed on the bench top at room temperature for 120 min. to reach equilibrium. Non-specific samples are assayed in the presence of 0.1 µM of the unlabeled antagonist phenylalanylvasopressin, added in 20.0 µl volume. For test compounds, these are solubilized in 50% dimethylsulfoxide (DMSO) and added in 20.0 µl volume to a final incubation volume of 200 µl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, Ohio).

Binding Assay to Rat Kidney Medullary $V_2$ Receptors

Medullary tissues from rat kidneys are dissected out, cut into small pieces and soaked in a 0.154 mM sodium chloride solution containing 1.0 mM EDTA with many changes of the liquid phase, until the solution is clear of blood. The tissue is homogenized in a 0.25M sucrose solution containing 1.0 mM EDTA and 0.1 mM PMSF using a Potter-Elvehjem homogenizer with a teflon pestle. The homogenate is filtered through several layers (4 layers) of cheese cloth. The filtrate is rehomogenized using a dounce homogenizer, with a tight fitting pestle. The final homogenate is centrifuged at 1500×g for 15 min. The nuclear pellet is discarded and the supernatant fluid recentrifuged at 40,000×g for 30 min. The resulting pellet formed contains a dark inner part with the exterior, slightly pink. The pink outer part is suspended in a small amount of 50.0 mM Tris.HCl buffer, pH 7.4. The protein content is determined by the Lowry's method (Lowry et al, J. Biol. Chem., 1953). The membrane suspension is stored at −70° C., in 50.0 mM Tris.HCl, containing 0.2% inactivated BSA and 0.1 mM PMSF in aliquots of 1.0 ml containing 10.0 mg protein per ml of suspension until use in subsequent binding experiments.

For binding experiments, the following is added in µl volume to wells of a 96 well format of a microtiter plate: 100.0 µl of 100.0 mM Tris.HCl buffer containing 0.2% heat inactivated BSA, 10.0 mM $MgCl_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 µl of [$^3$H]Arginine$^8$, vasopressin (S.A. 75.0 Ci/mmole) at 0.8 nM and the reaction initiated by the addition of 80.0 µl of tissue membranes (200.0 µg tissue protein). The plates are left undisturbed on the bench top for 120 min. to reach equilibrium. Non-specific binding is assessed in the presence of 1.0 µM of unlabeled ligand, added in 20 µl volume. For test compounds, these are solubilized in 50% dimethylsulfoxide (DMSO) and added in 20.0 µl volume to a final incubation volume of 200 µl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, Ohio). The results of this test on representative compounds of this invention are shown in Tables 1, 2 and 3.

Radioligand Binding Experiments With Human Platelet Membranes

Platelet Source: Hudson Valley Blood Services, Westchester Medical Center, Valhalla, N.Y.

Platelet Membrane Preparation:

Frozen platelet rich plasma (PRP), received from the Hudson Valley Blood Services, are thawed to room temperature. The tubes containing the PRP are centrifuged at 16,000×g for 10 min. at 4° C. and the supernatant fluid discarded. The platelets resuspended in an equal volume of 50.0 mM Tris.HCl, pH 7.5 containing 120 mM NaCl and 20.0 mM EDTA. The suspension is recentrifuged at 16,000×g for 10 min. This washing step is repeated one more time. The wash discarded and the lysed pellets homogenized in low ionic strength buffer of Tris.HCl, 5.0 mM, pH 7.5 containing 5.0 mM EDTA. The homogenate is centrifuged at 39,000×g for 10 min. The resulting pellet is resuspended in Tris.HCl buffer, 70.0 mM, pH 7.5 and recentrifuged at 39,000×g for 10 min. The final pellet is resuspended in 50.0 mM Tris.HCl buffer pH 7.4 containing 120 mM NaCl and 5.0 mM KCl to give 1.0–2.0 mg protein per ml of suspension.

Binding to vasopressin $V_1$ receptor subtype in Human Platelet Membranes:

In wells of 96 well format microtiter plate, add 100 µl of 50.0 mM Tris.HCl buffer containing 0.2% BSA and a mixture of protease inhibitors (aprotinin, leupeptin etc.). Then add 20 µl of [$^3$H]Ligand (Manning or Arg$^8$Vasopressin), to give final concentrations ranging from 0.01 to 10.0 nM. Initiate the binding by adding 80.0 µl of platelet suspension (approx. 100 µg protein). Mix all reagents by pipetting the mixture up and down a few times. Non specific binding is measured in the presence of 1.0 µM of unlabeled ligand (Manning or Arg$^8$Vasopressin). Let the mixture stand undisturbed at room temperature for ninety (90) min. Upon this time, rapidly filter off the incubate under vacuum suction over GF/B filters, using a Brandel® Harvester. Determine the radioactivity caught on the filter disks by the addition of liquid scintillant and counting in a liquid scintillator.

Binding to Membranes of Mouse Fibroblast Cell Line (LV-2) Transfected with the eDNA Expressing the Human $V_2$ Vasopressin Receptor Membrane Preparation Flasks of 175 ml capacity, containing attached cells grown to confluence, are cleared of culture medium by aspiration. The flasks containing the attached cells are rinsed with 2×5 ml of phosphate buffered saline (PBS) and the liquid aspirated off each time. Finally, 5 ml of an enzyme free dissociation Hank's based solution (Specialty Media, Inc., Lafayette, N.J.) is added and the flasks are left undisturbed for 2 min. The content of all flasks is poured into a centrifuge tube and the cells pelleted at 300×g for 15 min. The Hank's based solution is aspirated off and the cells homogenized with a polytron at setting #6 for 10 sec in 10.0 mM Tris.HCl buffer, pH 7.4 containing 0.25M sucrose and 1.0 mM EDTA. The homogenate is centrifuged at 1500×g for 10 min to remove ghost membranes. The supernatant fluid is centrifuged at 100,000×g for 60 min to pellet the receptor protein. Upon completion, the pellet is resuspended in a small volume of 50.0 mM Tris.HCl buffer, pH 7.4. The protein content is determined by the Lowry method and the receptor membranes are suspended in 50.0 mM Tris.HCl buffer containing 0.1 mM phenylmethylsulfonylfluoride (PMSF) and 0.2% bovine serum albumin (BSA) to give 2.5 mg receptor protein per ml of suspension.

Receptor Binding

For binding experiments, the following is added in µl volume to wells of a 96 well format of a microtiter plate: 100.0 µl of 100.0 mM Tris.HCl buffer containing 0.2% heat inactivated BSA, 10.0 mM $MgCl_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 µl of [$^3$H] Arginine$^8$, vasopressin (S.A. 75.0 Ci/mmole) at 0.8 nM and the reaction initiated by the addition of 80.0 µl of tissue membranes (200.0 µg tissue protein). The plates are left undisturbed on the bench top for 120 min to reach equilibrium. Non specific binding is assessed in the presence of 1.0 µM of unlabeled ligand, added in 20 µl volume. For test compounds, these are solubilized in 50% dimethylsulfoxide (DMSO) and added in 20.0 µl volume to a final incubation volume of 200 µl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, Ohio).

Oxytocin Receptor Binding (a) Membrane Preparation

Female Sprague-Dawley rats weighing approximately 200–250 g are injected intramuscularly (i.m.) with 0.3 mg/kg of body weight of diethylstilbestrol (DES). The rats are sacrificed 18 hours later under pentobarbital anesthesia. The uteri are dissected out, cleaned of fat and connective tissues and rinsed in 50 ml of normal saline. The tissue pooled from six rats is homogenized in 50 ml of 0.01 mM Tris.HCl, containing 0.5 mM dithiothreitol and 1.0 mM EDTA, adjusted to pH 7.4, using a polytron at setting 6 with three passes of 10 sec each. The homogenate is passed through two (2) layers of cheesecloth and the filtrate centrifuged at 1000×g for 10 min. The clear supernatant is removed and recentrifuged at 165,000×g for 30 min. The resulting pellet containing the oxytocin receptors is resuspended in 50.0 mM Tris.HCl containing 5.0 mM $MgCl_2$ at pH 7.4, to give a protein concentration of 2.5 mg/ml of tissue suspension. This preparation is used in subsequent binding assays with [$^3$H]Oxytocin.

(b) Radioligand Binding

Binding of 3,5-[$^3$H]Oxytocin ([$^3$H]OT) to its receptors is done in microtiter plates using [$^3$H]OT, at various concentrations, in an assay buffer of 50.0 mM Tris.HCl, pH 7.4 and containing 5.0 mM $MgCl_2$, and a mixture of protease inhibitors: BSA, 0.1 mg; aprotinin, 1.0 mg; 1,10-phenanthroline, 2.0 mg; trypsin, 10.0 mg; and PMSF, 0.3 mg per 100 ml of buffer solution. Non-specific binding is determined in the presence of 1.0 uM unlabeled OT. The binding reaction is terminated after 60 min., at 22° C., by rapid filtration through glass fiber filters using a Brandel® cell harvester (Biomedical Research and Development Laboratories, Inc., Gaithersburg, Md.). Competition experiments are conducted at equilibrium using 1.0 nM [$^3$H]OT and varying the concentration of the displacing agents. The concentrations of agent displacing 50% of [$^3$H]OT at its sites ($IC_{50}$) are calculated by a computer assisted LUNDON-2 program (LUNDON SOFTWARE INC., Ohio, U.S.A.).

The results of this assay on representative examples are shown in Table 4. When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

TABLE 1

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

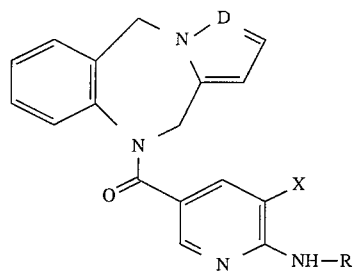

| Ex. No. | D | X | R | $V_1$ $IC_{50}$ (µM) | $V_2$ $IC_{50}$ (µM) |
|---|---|---|---|---|---|
| 1 | C | H | —CO—C$_6$H$_3$(CH$_3$)(F) | 0.033 *0.020 | 0.004 **0.005 |
| 5 | C | H | —CO—C$_6$H$_2$(OCH$_3$)$_3$ | *51% at 10 µM | **47% at 10 µM |
| 4 | C | H | —CO—C$_6$H$_3$(CH$_3$)(F) | *0.044 | 0.001 |
| 261 | C | H | —CH$_2$CH(CH$_3$)$_2$ | 65% at 1 µM | 32% at 1 µM |
| 208 | N | H | —CO—C$_6$H$_3$(CH$_3$)(F) | 0.087 | 0.011 |
| 273 | C | H | —CH$_2$—C$_6$H$_5$ | 0.190 | 0.082 |

TABLE 1-continued

Binding Assay to Rat Hepatic V₁ Receptors and Rat Kidney Medullary V₂ Receptors or *Binding to V₁ Receptor Subtype in Human Platelet and **Binding to Membranes of Mouse Fibroblast Cell Line (LV-2) Transfected with the cDNA Expressing the Human V₂ Receptor

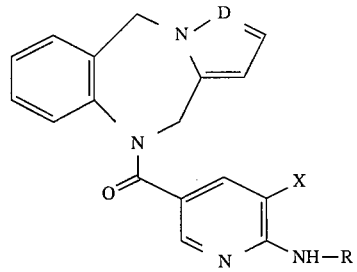

| Ex. No. | D | X | R | $V_1$ $IC_{50}$ (μM) | $V_2$ $IC_{50}$ (μM) |
|---|---|---|---|---|---|
| 262 | C | H | —CH₂CH₂C(CH₃)₂ | 64% at 1 μM | 50% at 1 μM |
| 263 | C | H | —CH₂-cyclohexyl | 0.200 | 0.360 |
| 12 | C | Br | —CO—(2-CH₃-phenyl) | 0.210 | 0.024 |
| 7 | C | H | —CO—(2,4-difluorophenyl) | 32% at 1 μM | 58% at 10 μM |
| 6 | C | H | —CO—(2-Cl-phenyl) | 0.011 | 0.0018 |
| 8 | C | H | —CO—(2-Br-phenyl) | 0.007 | 0.0016 |
| 301 | C | H | —(3-CH₃-phenyl) | 94% at 10 μM | 91% at 10 μM |
| 33 | C | H | —CO—(2-Cl-4-NO₂-phenyl) | 0.450 | 0.030 |

TABLE 1-continued

Binding Assay to Rat Hepatic V₁ Receptors and Rat Kidney Medullary V₂ Receptors or *Binding to V₁ Receptor Subtype in Human Platelet and **Binding to Membranes of Mouse Fibroblast Cell Line (LV-2) Transfected with the cDNA Expressing the Human V₂ Receptor

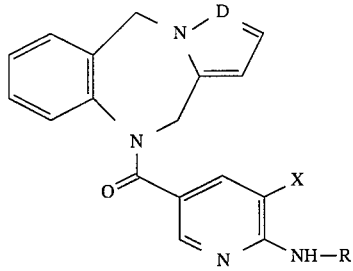

| Ex. No. | D | X | R | $V_1$ $IC_{50}$ (μM) | $V_2$ $IC_{50}$ (μM) |
|---|---|---|---|---|---|
| 9 | C | H | —CO—(2-Cl-4-F-phenyl) | 0.006 | 0.0011 **0.0009 |
| 261 | C | H | —CH₂CH(CH₃)₂ | 89% at 10 μM | 55% at 10 μM |
| 274 | C | H | —CH₂—(2-CH₃-phenyl) | 90% at 1 μM | 97% at 10 μM |
| 10 | C | H | —CO—(2-phenyl-phenyl) | 96% at 1 μM | 95% at 1 μM |
| 11 | C | H | —CO—(2-Cl-4-Br-phenyl) | 100% at 1 μM | 93% at 1 μM |
| 342 | C | H | —CO—(2-(2-N(CH₃)₂-phenyl)-phenyl) | | |
| 352 | C | H | —CH₂—(2-Br-phenyl) | 0.088 | 0.059 |

TABLE 1-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | D | X | R | $V_1$ $IC_{50}$ (µM) | $V_2$ $IC_{50}$ (µM) |
|---|---|---|---|---|---|
| 348 | C | H | —C(CH$_3$)$_3$ | 0.08 | 43% at 1 µM |
| 350 | C | H | 1-indanyl | 0.015 | 0.034 |
| 245 | N | H | 2-biphenylcarbonyl | 0.019 | 0.001 |
| 329 | C | H | 2-methylpyridine-3-carbonyl | 0.31 | 0.07 |
| 330 | C | H | 2-methylpyridine-3-carbonyl·HCl | 89% at 1 µM | 79% at 1 µM |
| 353 | C | H | 3-methylfuran-2-carbonyl | 93% at 1 µM | 86% at 1 µM |
| 43 | C | H | 2-nitrobenzoyl | 93% at 1 µM | |
| 351 | C | H | 2,4-dimethoxybenzyl | 73% at 1 µM | 56% at 1 µM |
| 354 | C | H | 2-aminobenzoyl | 29% at 1 µM | 86% at 1 µM |
| 14 | C | H | 2,4-dichlorobenzoyl | 100% at 1 µM | 99% at 1 µM |
| 18 | C | H | 2-fluoro-4-chlorobenzoyl | 98% at 1 µM | 94% at 1 µM |

TABLE 1A

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | X | R | $V_1$ $IC_{50}$ (μM) | $V_2$ $IC_{50}$ (μM) |
|---|---|---|---|---|
| 341 | H | -C(=O)-(2-pyridylphenyl) | 0.02 | 0.004 |
| 327 | H | -C(=O)-(2-methyl-3-pyridyl) | 0.35 | 0.028 |
| 347 | H | -C(=O)-C(CH₃)₂-O-(4-chlorophenyl) | 0.18 | 0.42 |
| 328 | Cl | -C(=O)-(2-methyl-3-pyridyl) | 3.3 | 0.019 |
| 324 | H | -C(=O)-(4'-CF₃-biphenyl-2-yl) | 0.42 | 0.12 |
| 333 | H | -C(=O)-(2-chloro-3-pyridyl) | 0.25 | 0.41 |
| 338 | H | -C(=O)-(2-N(CH₃)₂-3-pyridyl) | 0.037 | 0.0048 |
| 332 | H | -C(=O)-(2-N(CH₃)₂-3-pyridyl)·HCl | 0.031 | 0.0034 |
| 337 | H | N-methylpiperazinyl-(2-pyridyl-3-carbonyl) | 1.3 | 0.65 |
| 331 | H | N-methylpiperazinyl-(2-pyridyl-3-carbonyl)·HCl | 87% at 10 μM | 43% at 1 μM |

TABLE 1A-continued

Binding Assay to Rat Hepatic V₁ Receptors and Rat Kidney Medullary V₂ Receptors or *Binding to V₁ Receptor Subtype in Human Platelet and **Binding to Membranes of Mouse Fibroblast Cell Line (LV-2) Transfected with the cDNA Expressing the Human V₂ Receptor

| Ex. No. | X | R | $V_1$ $IC_{50}$ (μM) | $V_2$ $IC_{50}$ (μM) |
|---|---|---|---|---|
| 336 | H | -C(O)-(3-pyridyl)-2-piperidinyl | 99% at 1 μM | 69% at 1 μM |
| 334 | H | -C(O)-(3-pyridyl)-2-NHCH₃ | 15% at 1 μM | 79% at 1 μM |
| 339 | H | -C(O)-(3-pyridyl)-2-O-morpholinyl | 41% at 1 μM | 55% at 1 μM |
| 346 | H | -C(O)-(2-phenyl)-O-(4-chlorophenyl) | 44% at 10 μM | 76% at 10 μM |
| 326 | Cl | -C(O)-biphenyl-4'-CF₃ | 41% at 10 μM | 91% at 10 μM |
| 319 | Cl | -C(O)-biphenyl | 0.016 | 0.0015 |
| 320 | H | -C(O)-biphenyl | 0.0034 | 0.0026 |
| 321 | H | -C(O)-2-(CH₂-phenyl)phenyl | 0.018 | 0.0051 |
| 322 | Cl | -C(O)-2-(CH₂-phenyl)phenyl | 0.67 | 0.011 |

TABLE 1A-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

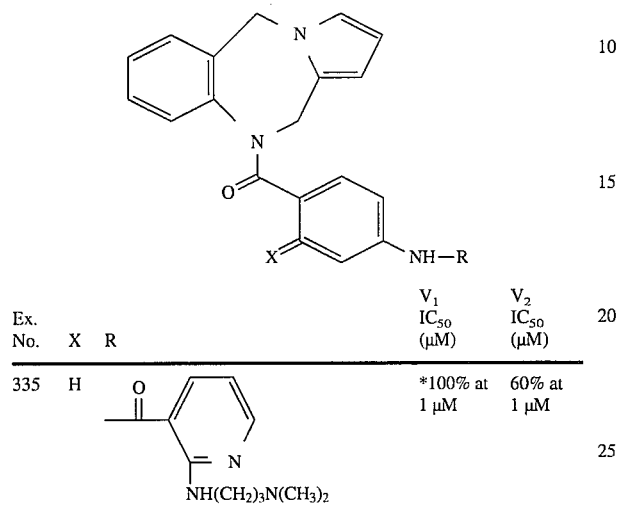

| Ex. No. | X | R | $V_1$ IC$_{50}$ (μM) | $V_2$ IC$_{50}$ (μM) |
|---|---|---|---|---|
| 335 | H | (structure: acetyl-pyridine with NH(CH₂)₃N(CH₃)₂) | *100% at 1 μM | 60% at 1 μM |

TABLE 2

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ IC$_{50}$ (μM) | $V_2$ IC$_{50}$ (μM) |
|---|---|---|---|
| 171 | (structure) | 630 | 31 |
| 288 | (structure) | 83% at 10 μM  49% at 1 μM | 54% at 10 μM |

TABLE 2-continued
Binding Assay to Rat Hepatic $V_1$ Receptors and Rat Kidney Medullary $V_2$ Receptors or
*Binding to $V_1$ Receptor Subtype in Human Platelet and **Binding to Membranes of
Mouse Fibroblast Cell Line (LV-2) Transfected with the cDNA Expressing the Human $V_2$ Receptor
| Ex. No. | Structure | $V_1$ $IC_{50}$ (μM) | $V_2$ $IC_{50}$ (μM) |
|---|---|---|---|
| 131 | 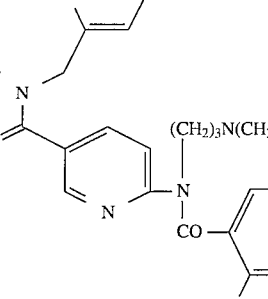 | 66% at 10 μM | 82% at 1 μM |
| 130 | 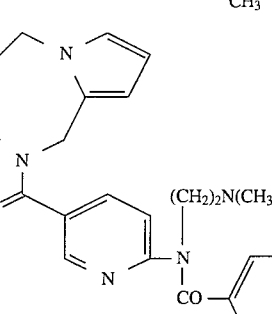 | 98% at 10 μM | 92% at 10 μM |
| 134 | 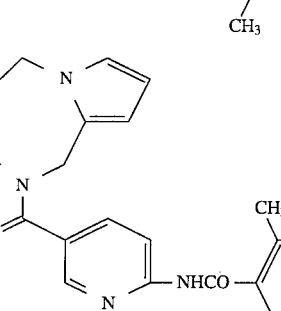 | 23% at 10 μM | 94% at 10 μM |

TABLE 3

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

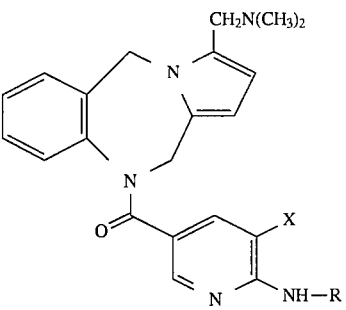

| Ex. No. | X | R | $V_1$ IC$_{50}$ (μM) | $V_2$ IC$_{50}$ (μM) |
|---|---|---|---|---|
| 133 | H | -CO-(OCH$_3$)(OCH$_3$)(OCH$_3$) | *11% at 10 μm | 21% at 10 μM |
| 120 | H | -CO-(CH$_3$)(F) phenyl | 99 | 33 |

TABLE 4

Oxytocin Binding Assay

| Ex. No. | Dose (μM) | % Inhibition | IC$_{50}$ (μM) |
|---|---|---|---|
| 1 | 10 | 92 | 0.20 |
| 5 | 10 | 93 | |
| 344 | 1 | 58 | 3.8 |
| 4 | 10 | 100 | 0.67 |
| 133 | 10 | 59 | |
| 261 | | | 0.15 |
| 120 | 1 | 8 | |
| 208 | 10 | 95 | 0.73 |
| 273 | 2.5 | 95 | 0.056 |
| 262 | 10 | 76 | 1.6 |
| 263 | 10 | 98 | 0.38 |
| 171 | 10 | 73 | 1.1 |
| 12 | 10 | 98 | 0.8 |
| 7 | 10 | 66 | |
| 6 | 1 | 90 | 0.14 |
| 8 | 1 | 89 | 0.15 |
| 301 | 10 | 89 | 0.86 |
| 288 | 10 | 94 | 1.36 |
| 33 | 10 | 95 | 0.51 |
| 9 | 2.5 | 96 | 0.17 |
| 131 | 10 | 60 | |
| 130 | 10 | 57 | |
| 134 | 1 | 63 | |
| 341 | 1 | 74 | |
| 327 | 1 | 56 | |
| 347 | 10 | 86 | |
| 328 | 10 | 85 | 0.57 |
| 324 | 1 | 45 | |
| 333 | 10 | 98 | 0.88 |

TABLE 4-continued

Oxytocin Binding Assay

| Ex. No. | Dose (μM) | % Inhibition | IC$_{50}$ (μM) |
|---|---|---|---|
| 338 | 10 | 98 | 0.72 |
| 332 | 10 | 98 | 0.83 |
| 337 | 1 | 16 | |
| 331 | 1 | 13 | |
| 336 | 10 | 94 | 1.63 |
| 334 | 1 | 5 | |
| 339 | 10 | 48 | 8.56 |
| 346 | 1 | 0 | |
| 326 | 1 | 0 | |
| 352 | 1.25 | 96 | 0.105 |
| 348 | 10 | 95 | 0.71 |
| 350 | 10 | 95 | 0.205 |
| 240 | 10 | 98 | 0.61 |
| 329 | 10 | 91 | 0.19 |
| 330 | 10 | 93 | 0.99 |
| 353 | 10 | 83 | 2.05 |
| 43 | 10 | 99 | 0.92 |
| 351 | 1 | 0 | |
| 354 | 1 | 7 | |
| 14 | 10 | 96 | 0.58 |
| 18 | 5 | 97 | 0.31 |

The compounds of the present invention can be used in the form of salts derived from pharmaceutically or physiologically acceptable acids or bases. These salts include, but are not limited to, the following: salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases. The compounds can also be used in the form of esters, carbamates and other conventional "pro-drug" forms, which, when administered in such form, convert to the active moiety in vivo.

When the compounds are employed for the above utilities, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfacrants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hardfilled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The new tricyclic non-peptide vasopressin antagonists of this invention are useful in treating conditions where decreased vasopressin levels are desired, such as in congestive heart failure, in disease conditions with excess renal water reabsorption and in conditions with increased vascular resistance and coronary vasoconstriction.

In particular, the vasopressin antagonists of this invention are therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, thrombosis-bleeding and abnormal states of water retention.

In particular, the oxytocin antagonists of this invention are useful in the prevention of preterm labor and premature birth which is a significant cause of infant health problems and infant mortality.

What is claimed is:

1. A compound selected from those of the formula:

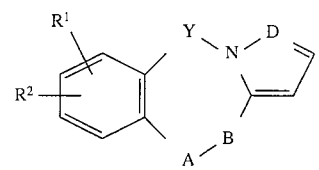

wherein Y is a moiety —(CH$_2$)—;

A–B is a moiety:

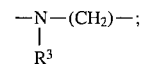

the moiety:

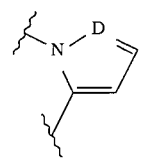

is a five membered aromatic (unsaturated) nitrogen containing heterocyclic ring optionally substituted by halogen, (C$_1$–C$_3$)lower alkyl, or —(CH$_2$)$_q$—N(R$_b$)$_2$ wherein:

D is carbon;

q is 1 or 2;

R$_b$ is independently selected from hydrogen, —CH$_3$, and —C$_2$H$_5$;

R$^3$ is a moiety of the formula:

wherein Ar is the moiety:

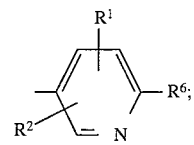

R$^1$ and R$^2$ are independently selected from hydrogen, (C$_1$–C$_3$)lower alkyl, (C$_1$–C$_3$)lower alkoxy or halogen;

R$^6$ is selected from:

a) moiety of the formula:

wherein R$_a$ is hydrogen and Ar' is a moiety of the formula:

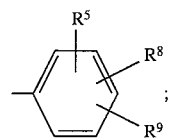

R$^5$ is selected from the group of hydrogen, lower alkyl(C$_1$–C$_3$) lower alkoxy or halogen;

R$^8$ and R$^9$ are selected from the group of hydrogen, lower alkyl(C$_1$–C$_3$), —S-lower alkyl(C$_1$–C$_3$), halogen, —NH-lower alkyl(C$_1$–C$_3$), —N-[lower alkyl(C$_1$–C$_3$)]$_2$, —OCF$_3$, —OH, —CN, —S-CF$_3$, —NO$_2$, —NH$_2$, O-lower alkyl($C_1$–$C_3$), $CF_3$, or

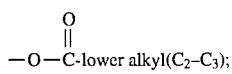

b) a moiety of the formula:

wherein $R_b$ is hydrogen and J is a moiety:

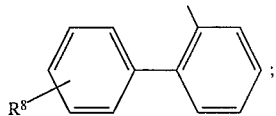

and the pharmaceutically acceptable salts, esters and prodrug forms thereof.

2. The compound according to claim 1, N-[5-(5H-pyrrolo [2,1-c][1,4]benzodiazepin-10(11H)-ylcarbonyl)-2-pyridinyl]-5-fluoro-2-methylbenzamide.

3. A pharmaceutical composition useful for treating disease in a mammal characterized by excess renal reabsorption of water, the pharmaceutical composition comprising an effective amount of a compound of claim 1, or a pharmaceutically acceptable salt, ester or prodrug form thereof, and a suitable pharmaceutical carrier.

4. The pharmaceutical composition of claim 2 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

5. A method for treating disease in a mammal characterized by excess renal reabsorption of water, the method comprising administering to a mammal in need thereof an effective amount of a compound of claim 1, or a pharmaceutically acceptable salt, ester or prodrug form thereof, and a suitable pharmaceutical carrier.

6. The method of claim 5 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

\* \* \* \* \*

UNITED STATES PATENT AND TRADEMARK OFFICE
CERTIFICATE OF CORRECTION

PATENT NO. : 5,610,156

DATED : March 11, 1997

INVENTOR(S) : Jay D. Albright, Aranapakam M. Venkatesan

It is certified that error appears in the above-indentified patent and that said Letters Patent is hereby corrected as shown below:

Item [57]

In the Abstract please delete Formula I

"
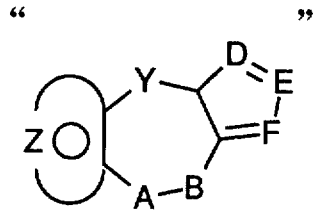
"

and insert therefore

"
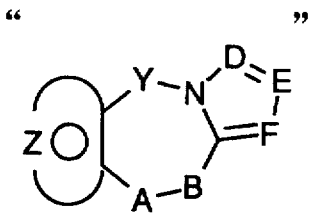
"

Signed and Sealed this

Fifteenth Day of July, 1997

Attest:

Bruce Lehman

BRUCE LEHMAN

*Attesting Officer*  *Commissioner of Patents and Trademarks*